(12) United States Patent
Jeon et al.

(10) Patent No.: US 11,469,381 B2
(45) Date of Patent: Oct. 11, 2022

(54) CONDENSED CYCLIC COMPOUND AND ORGANIC LIGHT-EMITTING DEVICE INCLUDING THE SAME

(71) Applicants: Samsung Electronics Co., Ltd., Suwon-si (KR); Samsung SDI Co., Ltd., Yongin-si (KR)

(72) Inventors: Soonok Jeon, Suwon-si (KR); Eunsuk Kwon, Suwon-si (KR); Sangmo Kim, Hwaseong-si (KR); Jongsoo Kim, Seoul (KR); Joonghyuk Kim, Seoul (KR); Jhunmo Son, Yongin-si (KR); Yeonsook Chung, Seoul (KR); Yongsik Jung, Yongin-si (KR)

(73) Assignees: SAMSUNG ELECTRONICS CO., LTD., Gyeonggi-Do (KR); SAMSUNG SDI CO., LTD., Gyeonggi-Do (KR)

( * ) Notice: Subject to any disclaimer, the term of this patent is extended or adjusted under 35 U.S.C. 154(b) by 303 days.

(21) Appl. No.: 16/176,145

(22) Filed: Oct. 31, 2018

(65) Prior Publication Data

US 2019/0312209 A1 Oct. 10, 2019

(30) Foreign Application Priority Data

Apr. 9, 2018 (KR) ........................ 10-2018-0041243

(51) Int. Cl.
*H01L 51/50* (2006.01)
*H01L 51/00* (2006.01)
*C07D 471/04* (2006.01)
(Continued)

(52) U.S. Cl.
CPC ........ *H01L 51/0072* (2013.01); *C07D 471/04* (2013.01); *C09K 11/06* (2013.01); *C09K 2211/1018* (2013.01); *H01L 51/001* (2013.01);

*H01L 51/5004* (2013.01); *H01L 51/5012* (2013.01); *H01L 51/5056* (2013.01); *H01L 51/5072* (2013.01); *H01L 51/5088* (2013.01);
(Continued)

(58) Field of Classification Search
None
See application file for complete search history.

(56) References Cited

U.S. PATENT DOCUMENTS 8,597,801 B2 12/2013 Kwak et al.
9,209,410 B2 12/2015 Iwakuma et al.
(Continued)

FOREIGN PATENT DOCUMENTS

KR 10-2010-0031736 A 3/2010
KR 10-2010-0032888 A 3/2010
(Continued)

OTHER PUBLICATIONS

Let et al., Thermally stable carboline derivatives as a host material for blue phosphorescent organic light-emitting diodes, (2013), Organic Electronics 14; 2687-2691 (Year: 2013).*

(Continued)

*Primary Examiner* — Gregory D Clark
(74) *Attorney, Agent, or Firm* — Cantor Colburn LLP

(57) ABSTRACT

A condensed cyclic compound represented by Formula 1:

$$Ar_1-L_1-L_2-Ar_2 \quad \text{Formula 1}$$

wherein, in Formula 1, $Ar_1$, $Ar_2$, $L_1$, and $L_2$ are the same as described in the specification.

9 Claims, 1 Drawing Sheet

(51) Int. Cl.
    *C09K 11/06*     (2006.01)
    *H01L 51/56*     (2006.01)

(52) U.S. Cl.
    CPC ........ *H01L 51/56* (2013.01); *H01L 2251/552* (2013.01); *H01L 2251/558* (2013.01)

(56) References Cited

U.S. PATENT DOCUMENTS

| | | | |
|---|---|---|---|
| 2004/0170863 A1* | 9/2004 | Kim | C07D 241/42 313/506 |
| 2009/0236974 A1* | 9/2009 | Tamaru | H05B 33/14 313/504 |
| 2013/0112952 A1* | 5/2013 | Adamovich | C09B 57/00 257/40 |
| 2015/0243903 A1 | 5/2015 | Aoki | |
| 2016/0013423 A1 | 1/2016 | Huh et al. | |
| 2016/0079545 A1* | 3/2016 | Fukuzaki | H01L 51/0094 257/40 |
| 2019/0067616 A1 | 2/2019 | Jeon et al. | |

FOREIGN PATENT DOCUMENTS

| | | | | |
|---|---|---|---|---|
| KR | 10-2011-0088457 A | 8/2011 | | |
| KR | 10-2011-0132721 A | 12/2011 | | |
| KR | 10-2012-0092908 A | 8/2012 | | |
| KR | 10-2012-0125788 A | 11/2012 | | |
| KR | 2011129767 | * | 4/2013 | ............ H01L 51/50 |
| KR | 10-1453128 B1 | 10/2014 | | |
| KR | 10-2015-0062241 A | 6/2015 | | |
| KR | 10-1528767 B1 | 6/2015 | | |
| KR | 10-2016-0006629 A | 1/2016 | | |
| KR | 10-2016-0061522 A | 6/2016 | | |
| WO | 2015-175678 A1 | 11/2015 | | |

OTHER PUBLICATIONS

Lee et al., Effect of nitrogen position of carboline on the device performances of blue phosphorescent organic light-emitting diodes; Synthetic Metals 209 (2015) 24-28 (Year: 2015).*

* cited by examiner

10

| 19 |
|---|
| 15 |
| 11 |

CONDENSED CYCLIC COMPOUND AND ORGANIC LIGHT-EMITTING DEVICE INCLUDING THE SAME

CROSS-REFERENCE TO RELATED APPLICATION

This application claims priority to Korean Patent Application No. 10-2018-0041243, filed on Apr. 9, 2018, in the Korean Intellectual Property Office, and all the benefits accruing therefrom under 35 U.S.C. § 119, the content of which is incorporated herein in its entirety by reference.

BACKGROUND

1. Field

The present disclosure relates to a condensed cyclic compound and an organic light-emitting device including the condensed cyclic compound.

2. Description of the Related Art

Organic light-emitting devices (OLEDs) are self-emission devices that have relatively wide viewing angles, relatively high contrast ratios, relatively short response times, and increased luminance, driving voltage, and response speed characteristics. OLEDs may produce full-color images.

OLEDs typically include an anode, a cathode, and an organic layer disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers, such as holes and electrons, recombine in the emission layer to produce excitons. These excitons transit from an excited state to a ground state to thereby generate light.

Various types of organic light emitting devices are known. However, there still remains a need in OLEDs having low driving voltage, high efficiency, high brightness, and long lifespan.

SUMMARY

Provided are a condensed cyclic compound and an organic light-emitting device including the condensed cyclic compound.

Additional aspects will be set forth in part in the description which follows and, in part, will be apparent from the description, or may be learned by practice of the presented embodiments.

According to an aspect of an embodiment, a condensed cyclic compound is represented by Formula 1:

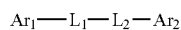

Formula 1

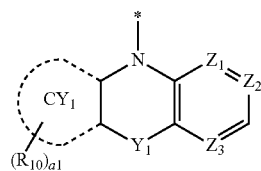

Formula 2

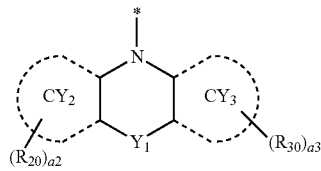

Formula 3

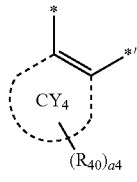

Formula 4

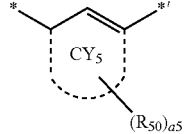

Formula 5 wherein in Formulae 1 to 5, $Ar_1$ may be a group represented by Formula 2, $Ar_2$ may be a group represented by Formula 3, $CY_1$ to $CY_3$ may each independently be a $C_5$-$C_{30}$ carbocyclic group or a $C_1$-$C_{30}$ heterocyclic group, $Z_1$ may be N or $C(R_1)$, $Z_2$ may be N or $C(R_2)$, $Z_3$ may be N or $C(R_3)$, at least one selected from $Z_1$ to $Z_3$ may be N, $Y_1$ may be a single bond, $C(R_4)(R_5)$, $N(R_4)$, O, or S, $Y_2$ may be a single bond, $C(R_6)(R_7)$, $N(R_6)$, O, or S, $L_1$ and $L_2$ may each independently be selected from a group represented by Formula 4 and a group represented by Formula 5, $CY_4$ and $CY_5$ may each independently be selected from a $C_5$-$C_{30}$ carbocyclic group, $R_1$ to $R_7$, $R_{10}$, $R_{20}$, and $R_{30}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_6$)($Q_7$), $R_{40}$ and $R_{50}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_6$)($Q_7$), a1 to a5 may each independently be an integer from 0 to 10,

* and *' each indicate a binding site to an adjacent atom, and at least one substituent of the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_{60}$ alkoxy group, each substituted with at least one selected from deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group and a monovalent non-aromatic condensed heteropolycyclic group, each substituted with at least one selected from deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$), and —B($Q_{26}$)($Q_{27}$); and —Si($Q_{31}$)($Q_{32}$)($Q_{33}$), —N($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

According to an aspect of another embodiment, an organic light-emitting device includes:

a first electrode;

a second electrode; and an organic layer disposed between the first electrode and the second electrode, wherein the organic layer includes an emission layer and at least one condensed cyclic compound represented by Formula 1.

The condensed cyclic compound may be included in the emission layer, wherein the emission layer may further include a dopant, and wherein the condensed cyclic compound may be a host.

BRIEF DESCRIPTION OF THE DRAWINGS

These and/or other aspects will become apparent and more readily appreciated from the following description of the embodiments, taken in conjunction with FIGURE which is a schematic cross-sectional view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the FIGURES, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the FIGURES, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

A condensed cyclic compound may be represented by Formula 1:

Formula 1

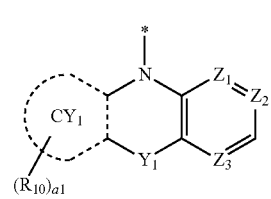

Formula 2

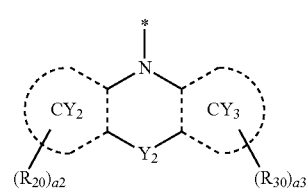

Formula 3

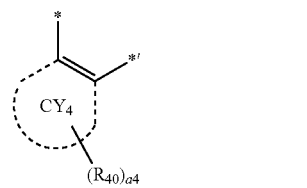

Formula 4

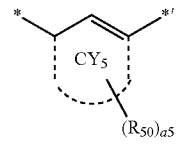

Formula 5 wherein, in Formula 1, $Ar_1$ may be a group represented by Formula 2, and $Ar_2$ may be a group represented by Formula 3.

In Formulae 2 and 3, $CY_1$ to $CY_3$ may each independently be a $C_5$-$C_{30}$ carbocyclic group or a $C_1$-$C_{30}$ heterocyclic group.

In some embodiments, $CY_1$ to $CY_3$ may each independently be selected from a benzene group, a fluorene group, a carbazole group, a dibenzofuran group, and a dibenzothiophene group.

In some embodiments, $CY_1$ may be a benzene group, but embodiments are not limited thereto.

In some embodiments, $CY_2$ may be a benzene group, and $CY_3$ may be selected from a benzene group, a fluorene group, a carbazole group, a dibenzofuran group, and a dibenzothiophene group.

In some embodiments, $CY_2$ and $CY_3$ may each be a benzene group.

In some embodiments, $Ar_1$ may be a group represented by one of Formulae 2-1 to 2-7, and $Ar_2$ may be a group represented by one of Formulae 3-1 to 3-14:

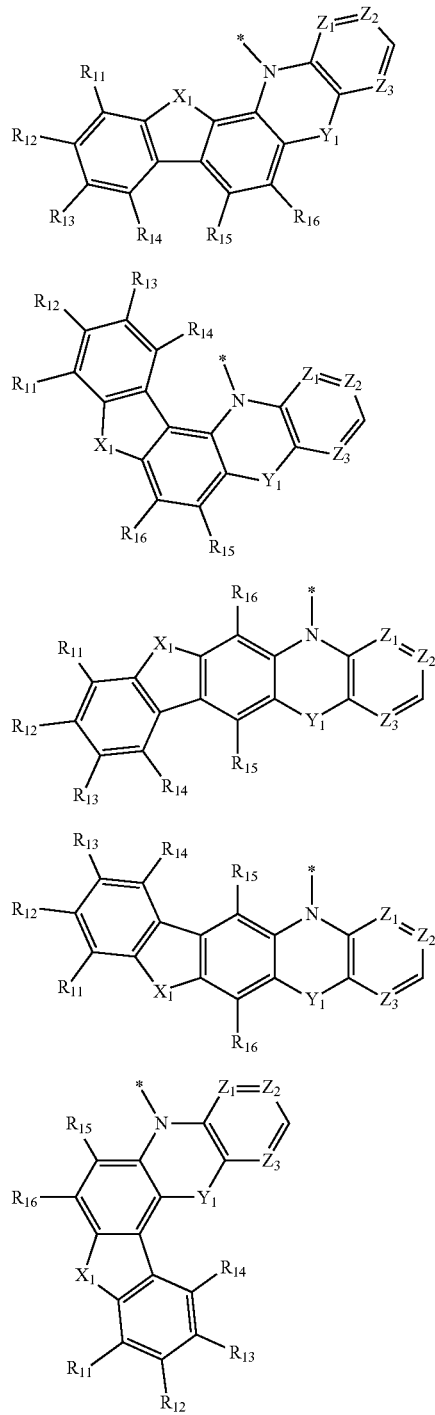

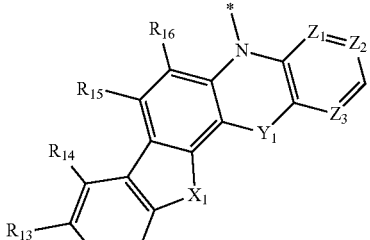

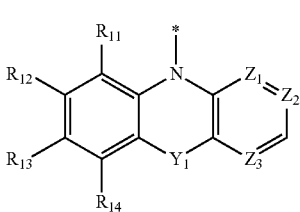

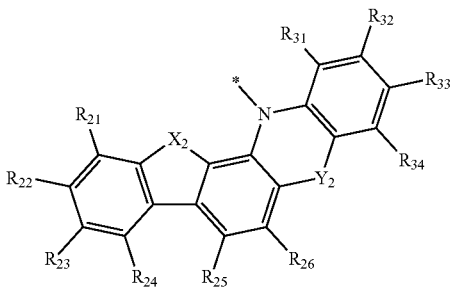

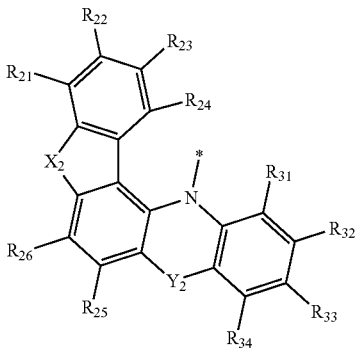

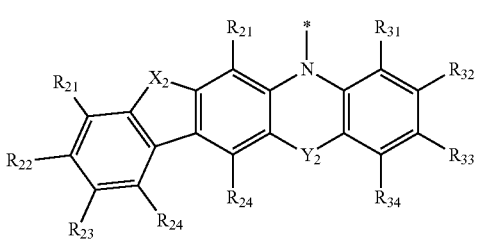

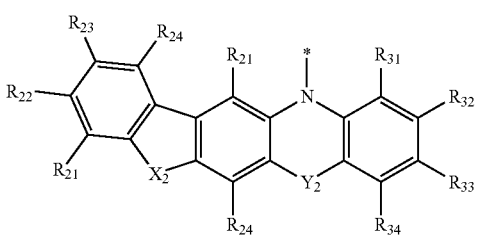

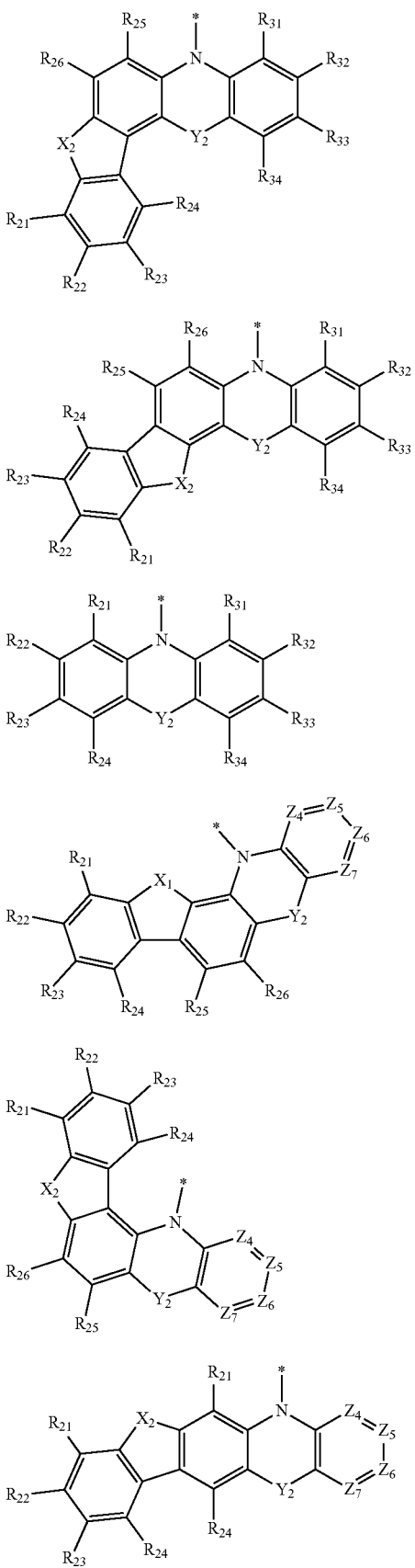
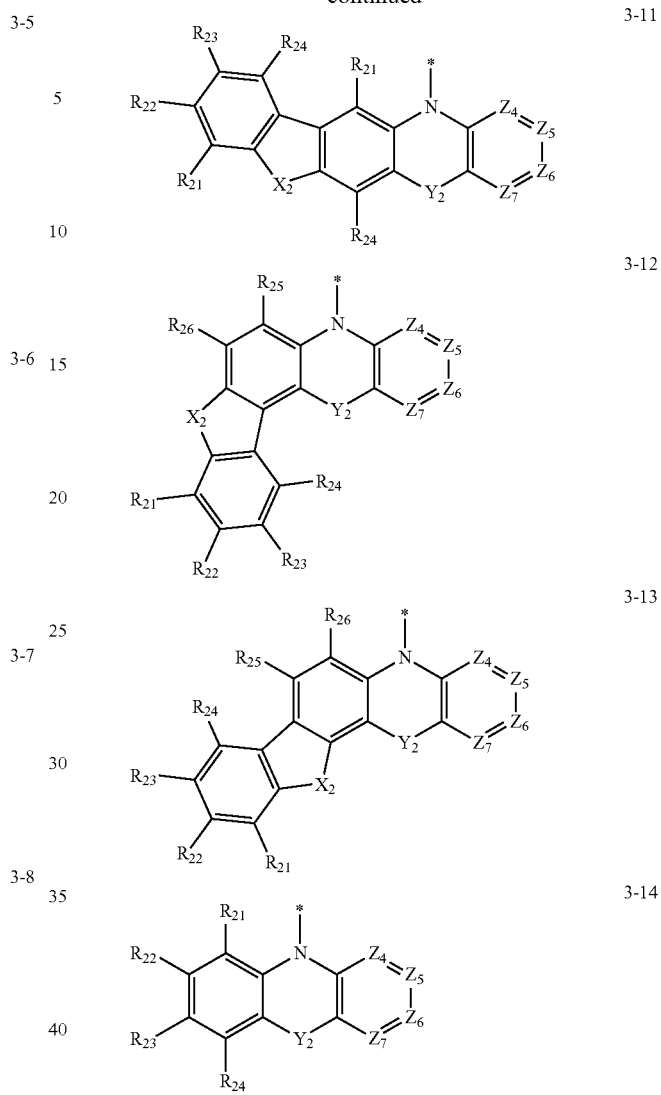

wherein, in Formulae 2-1 to 2-7 and 3-1 to 3-14,
$X_1$ may be $C(R_{17})(R_{18})$, $N(R_{19})$, O, or S,
$X_2$ may be $C(R_{27})(R_{28})$, $N(R_{29})$, O, or S,
$Z_1$ to $Z_3$, $Y_1$, and $Y_2$ may respectively be understood by referring to the descriptions for those provided herein,
$Z_4$ may be N or $C(R_{31})$, $Z_5$ may be N or $C(R_{32})$, $Z_6$ may be N or $C(R_{33})$, $Z_7$ may be N or $C(R_{34})$, at least one selected from $Z_4$ to $Z_7$ may be N, and
$R_1$ to $R_7$, $R_{11}$ to $R_{19}$, $R_{21}$ to $R_{29}$, and $R_{31}$ to $R_{34}$ may each independently be selected from:
hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;
a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group, and a naphthyl group;

a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, an imidazopyridinyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzoxazinyl group, and a pyridobenzothiazinyl group;

a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, an imidazopyridinyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzoxazinyl group, and a pyridobenzothiazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a biphenyl group, a terphenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, —Si($Q_{31}$)($Q_{32}$)($Q_{33}$), —N($Q_{34}$)($Q_{35}$), and —B($Q_{36}$)($Q_{37}$); and —Si($Q_1$)($Q_2$)($Q_3$), —N($Q_4$)($Q_5$), and —B($Q_6$)($Q_7$), wherein $Q_1$ to $Q_7$ and $Q_{31}$ to $Q_{37}$ may each independently be selected from hydrogen, a $C_1$-$C_{20}$ alkyl group, a $C_1$-$C_{20}$ alkoxy group, a phenyl group, a biphenyl group, a terphenyl group, a naphthyl group, a fluorenyl group, a carbazolyl group, a dibenzofuranyl group, and a dibenzothiophenyl group, and

* indicates a binding site to an adjacent atom.

In some embodiments, in Formulae 2-1 to 2-7 and 3-1 to 3-14, $R_1$ to $R_7$, $R_{11}$ to $R_{19}$, $R_{21}$ to $R_{29}$, and $R_{31}$ to $R_{34}$ may each independently be selected from:

hydrogen, deuterium, —F, —Cl, —Br, —I, a cyano group, a $C_1$-$C_{20}$ alkyl group, and a alkoxy group;

a $C_1$-$C_{20}$ alkyl group and a $C_1$-$C_{20}$ alkoxy group, each substituted with at least one selected from deuterium, —F, —Cl, —Br, —I, a cyano group, a phenyl group, a biphenyl group, a terphenyl group, and a naphthyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group, each substituted with at least one selected from deuterium, a cyano group, a $C_1$-$C_{20}$ alkyl group, a $C_1$-$C_{20}$ alkoxy group, a phenyl group, a biphenyl group, a terphenyl group, a naphthyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ may each independently be selected from hydrogen, a $C_1$-$C_{20}$ alkyl group, a $C_1$-$C_{20}$ alkoxy group, a phenyl group, a biphenyl group, a terphenyl group, and a naphthyl group.

In some embodiments, in Formulae 2-1 to 2-7 and 3-1 to 14, $X_1$ may be O or S.

In some embodiments, in Formulae 2-1 to 2-7 and 3-1 to 3-14, at least one selected from $Z_4$, $Z_5$, and $Z_7$ may be N.

In some embodiments, in Formulae 2-1 to 2-7 and 3-1 to 3-14, $Z_4$ may be N or C($R_{31}$), $Z_5$ may be N or C($R_{32}$), $Z_6$ may be C($R_{33}$), $Z_7$ may be N or C($R_{34}$), and at least one selected from $Z_4$, $Z_5$, and $Z_7$ may be N.

In some embodiments, $Ar_1$ may be represented by Formula 2-7, and $Ar_2$ may be represented by Formula 3-7, but embodiments are not limited thereto.

In Formula 2, $Z_1$ may be N or C($R_1$), $Z_2$ may be N or C($R_2$), $Z_3$ may be N or C($R_3$), at least one selected from $Z_1$ to $Z_3$ may be N.

In some embodiments, at least one selected from $Z_1$ to $Z_3$ may be N.

In Formulae 2 and 3, $Y_1$ may be a single bond, $C(R_4)(R_5)$, $N(R_4)$, O, or S, and $Y_2$ may be a single bond, $C(R_6)(R_7)$, $N(R_6)$, O, or S.

In some embodiments, $Y_1$ may be a single bond.

In some embodiments, $Y_2$ may be a single bond.

In Formula 1, $L_1$ and $L_2$ may each independently be selected from a group represented by Formula 4 and a group represented by Formula 5.

In some embodiments, in Formula 1, $L_1$ and $L_2$ may be identical to each other.

In Formulae 4 and 5, $CY_4$ and $CY_5$ may each independently be selected from a $C_5$-$C_{30}$ carbocyclic group.

In some embodiments, $CY_4$ and $CY_5$ may each independently be selected from a benzene group, a naphthalene group, and a fluorene group.

In Formulae 2 to 5, $R_1$ to $R_7$, $R_{10}$, $R_{20}$, and $R_{30}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si$(Q_1)(Q_2)(Q_3)$, —N$(Q_4)(Q_5)$, and —B$(Q_6)(Q_7)$, and $R_{40}$ and $R_{50}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si$(Q_1)(Q_2)(Q_3)$, —N$(Q_4)(Q_5)$, and —B$(Q_6)(Q_7)$.

In some embodiments, at least one selected from $R_{10}$, $R_{20}$, $R_{30}$, $R_{40}$, and $R_{50}$ may be a cyano group.

In Formulae 2 to 5, a1 to a5 may each independently be an integer from 0 to 10.

In some embodiments, the condensed cyclic compound represented by Formula 1 may be represented by one of Formulae 1-1 to 1-4:

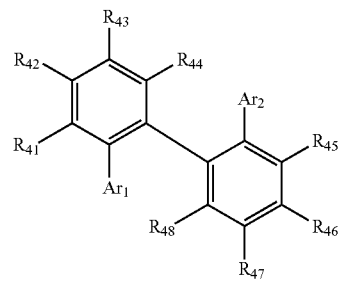

1-1

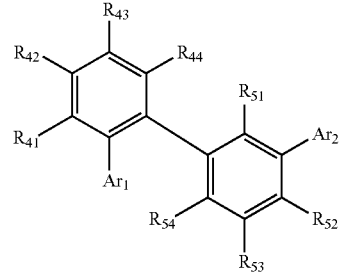

1-2

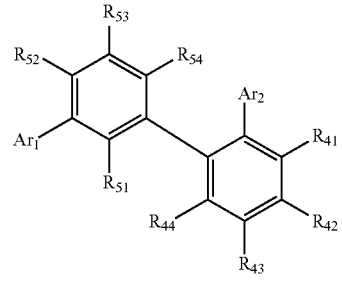

1-3

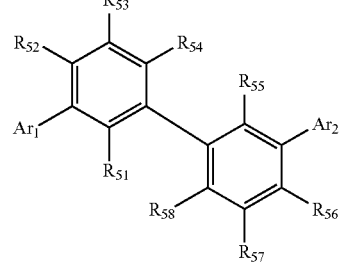

1-4 wherein, in Formulae 1-1 to 1-4, $Ar_1$ and $Ar_2$ may respectively be understood by referring to the descriptions for those provided herein, $R_{41}$ to $R_{48}$ may each be understood by referring to the descriptions for $R_{40}$ provided herein, and $R_{51}$ to $R_{58}$ may each be understood by referring to the descriptions for $R_{50}$ provided herein.

In some embodiments, the condensed cyclic compound represented by Formula 1 may be represented by Formula 1-4.

In some embodiments, in Formulae 1-1 to 1-4, $R_{41}$ to $R_{48}$ and $R_{51}$ to $R_{58}$ may each independently be selected from:

hydrogen, deuterium, —F, —Cl, —Br, —I, a cyano group, a $C_1$-$C_{20}$ alkyl group, and a alkoxy group;

a $C_1$-$C_{20}$ alkyl group and a $C_1$-$C_{20}$ alkoxy group, each substituted with at least one selected from deuterium, a phenyl group, a biphenyl group, a terphenyl group, and a naphthyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group, each substituted with at least one selected from deuterium, a $C_1$-$C_{20}$ alkyl group, a $C_1$-$C_{20}$ alkoxy group, a phenyl group, a biphenyl group, a terphenyl group, a naphthyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ may each independently be selected from hydrogen, a $C_1$-$C_{20}$ alkyl group, a $C_1$-$C_{20}$ alkoxy group, a phenyl group, a biphenyl group, a terphenyl group, and a naphthyl group.

In some embodiments, in Formulae 1-1 to 1-4, $Ar_1$ may be selected from a group represented by one of Formulae 2-1 to 2-7, and $Ar_2$ may be a group represented by one of Formulae 3-1 to 3-14:

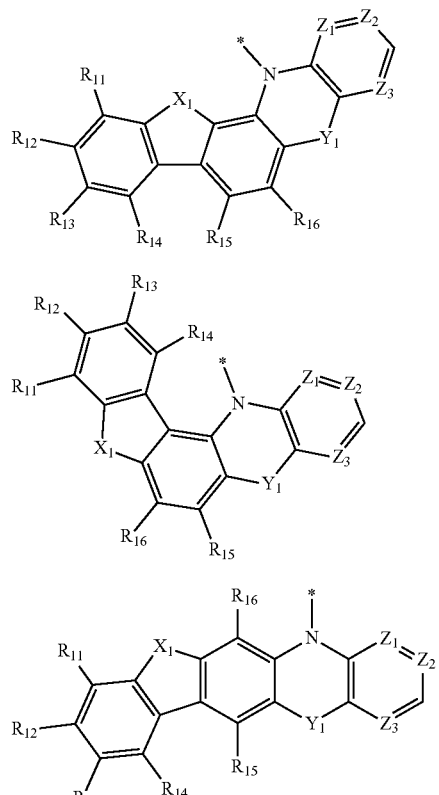

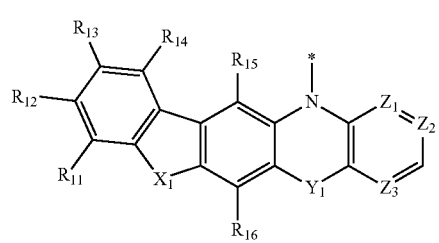

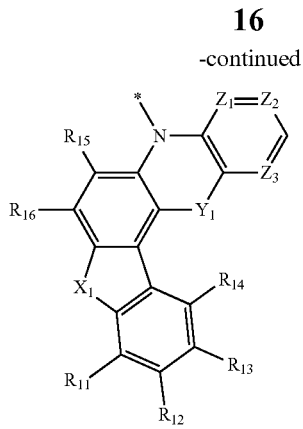

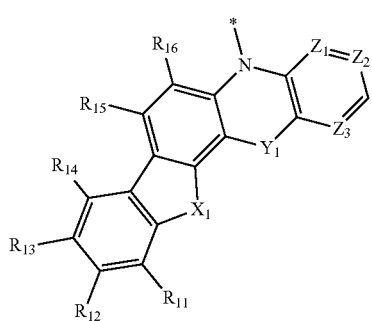

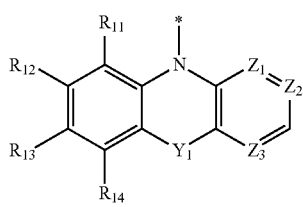

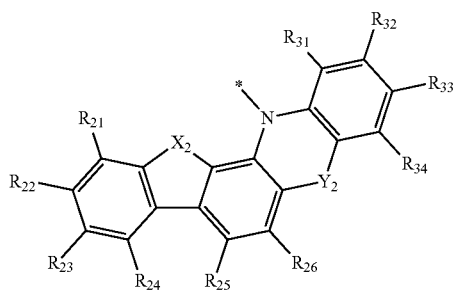

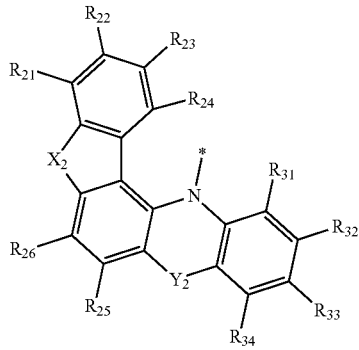

-continued
3-3
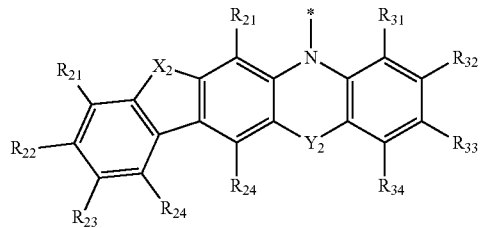
3-4
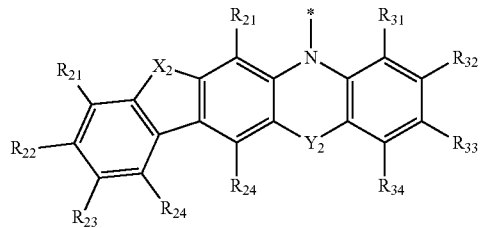
3-5
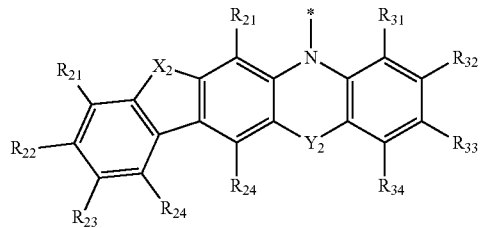
3-6
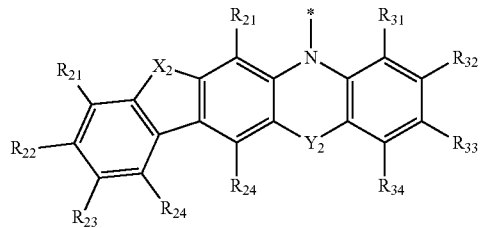
3-7
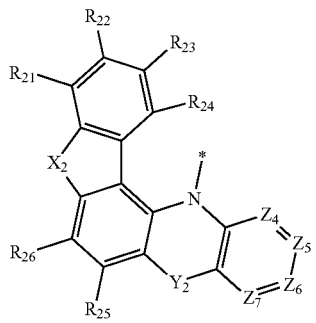
3-8
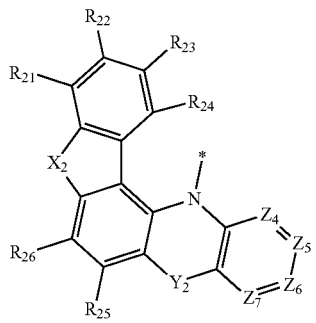
3-9
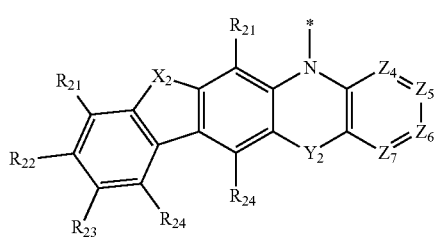
3-10
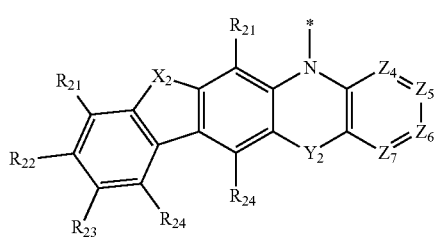
3-11
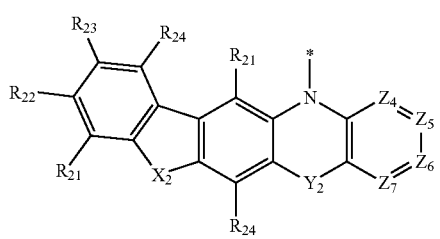
3-12
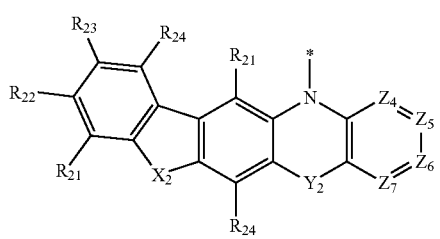
3-13
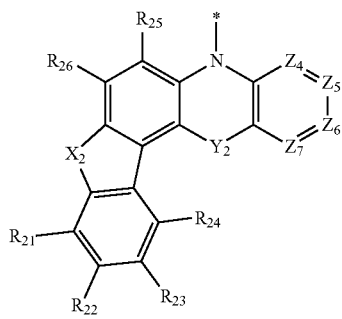
3-14
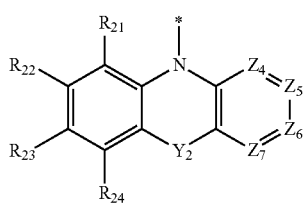
wherein, in Formulae 2-1 to 2-7 and 3-1 to 3-14, $X_1$ may be $C(R_{17})(R_{18})$, $N(R_{19})$, O, or S, $X_2$ may be $C(R_{27})(R_{28})$, $N(R_{29})$, O, or S, $Z_1$ to $Z_3$, $Y_1$, and $Y_2$ may respectively be understood by referring to the descriptions for those provided herein, $Z_4$ may be N or $C(R_{31})$, $Z_5$ may be N or $C(R_{32})$, $Z_6$ may be N or $C(R_{33})$, $Z_7$ may be N or $C(R_{34})$, at least one selected from $Z_4$ to $Z_7$ may be N, and $R_1$ to $R_7$, $R_{11}$ to $R_{19}$, $R_{21}$ to $R_{29}$, and $R_{31}$ to $R_{34}$ may each independently be selected from:

hydrogen, deuterium, a cyano group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, a cyano group, a phenyl group, a biphenyl group, a terphenyl group, and a naphthyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group, each substituted with at least one selected from deuterium, a cyano group, a $C_1$-$C_{20}$ alkyl group, a $C_1$-$C_{20}$ alkoxy group, a phenyl group, a biphenyl group, a terphenyl group, a naphthyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ may each independently be selected from hydrogen, a $C_1$-$C_{20}$ alkyl group, a $C_1$-$C_{20}$ alkoxy group, a phenyl group, a biphenyl group, a terphenyl group, and a naphthyl group.

In some embodiments, at least one selected from $R_{11}$ to $R_{19}$, $R_{21}$ to $R_{29}$, $R_{31}$ to $R_{34}$, $R_{41}$ to $R_{48}$, and $R_{51}$ to $R_{58}$ may be a cyano group.

At least one substituent of the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_{60}$ alkoxy group, each substituted with at least one selected from deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group and a monovalent non-aromatic condensed heteropolycyclic group, each substituted with at least one selected from deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$), and —B($Q_{26}$)($Q_{27}$); and —Si($Q_{31}$)($Q_{32}$)($Q_{33}$), —N($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In some embodiments, the condensed cyclic compound represented by Formula 1 may be selected from Compounds 1 to 222, but embodiments are not limited thereto:

1
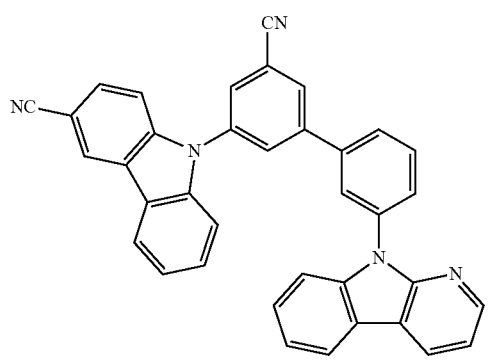
2
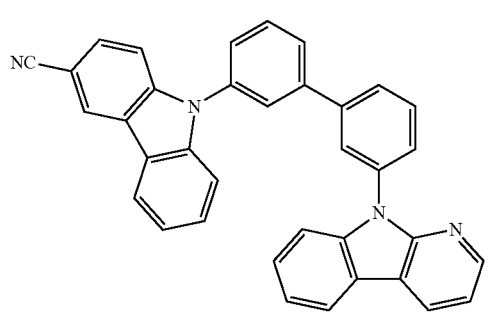
3
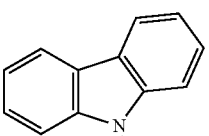
4
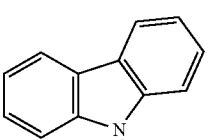
5
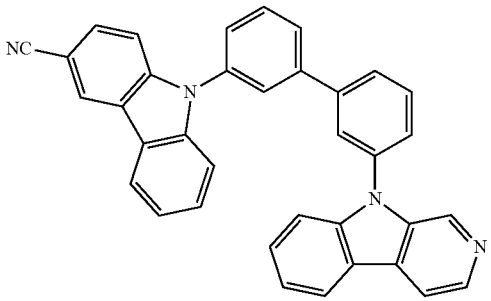
6
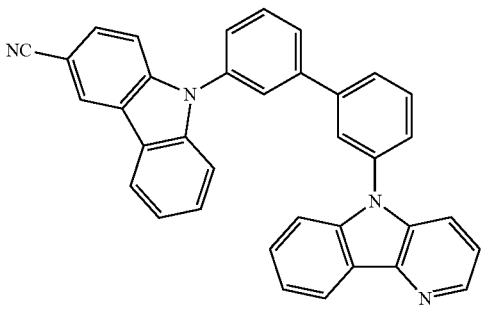
7
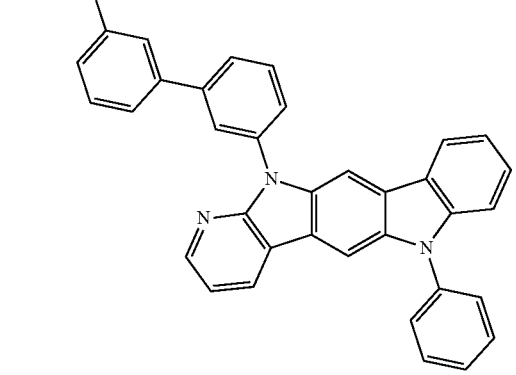
8
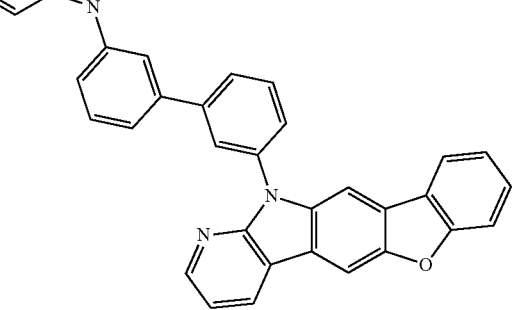

9
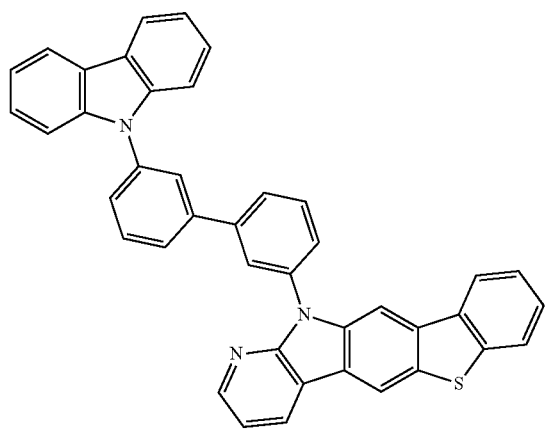
10
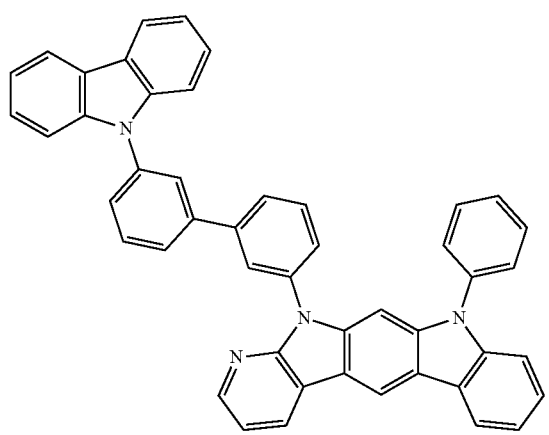
11
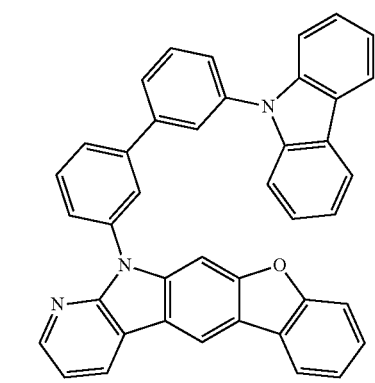
12
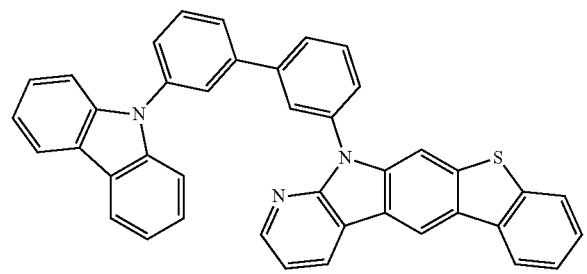
13
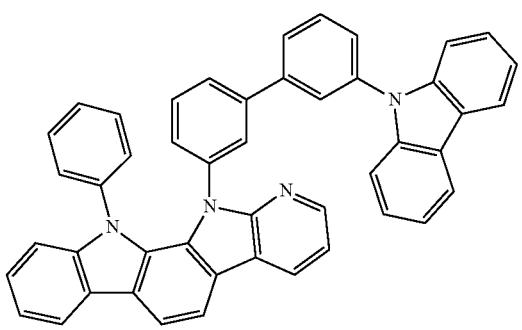
14
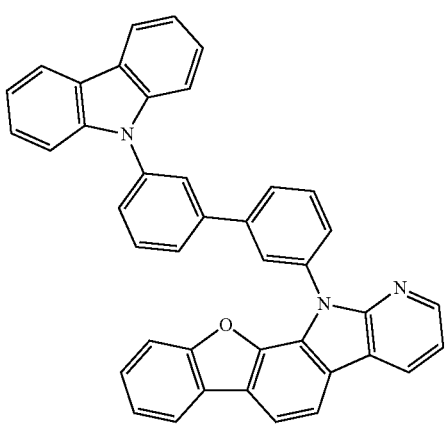
15
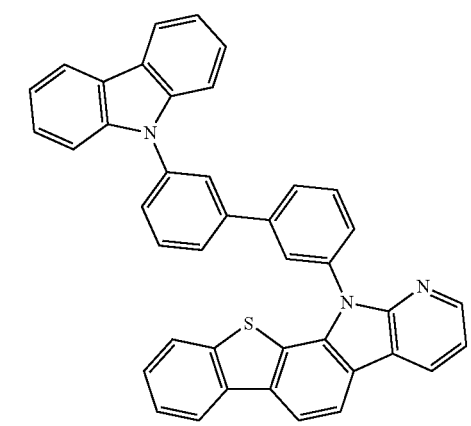

16
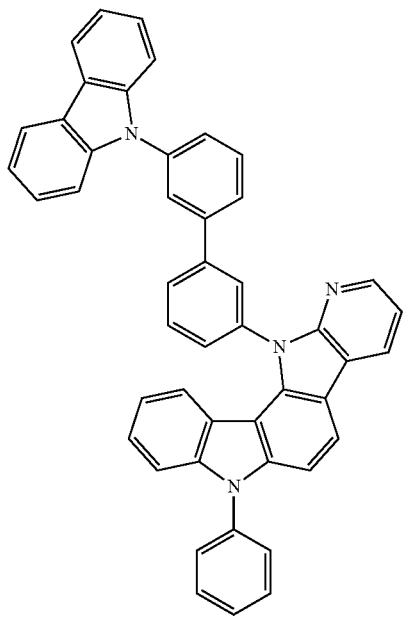
17
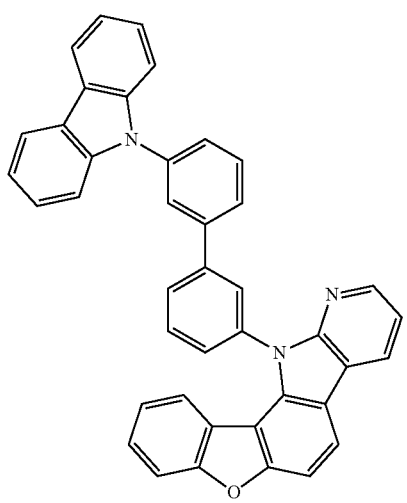
18
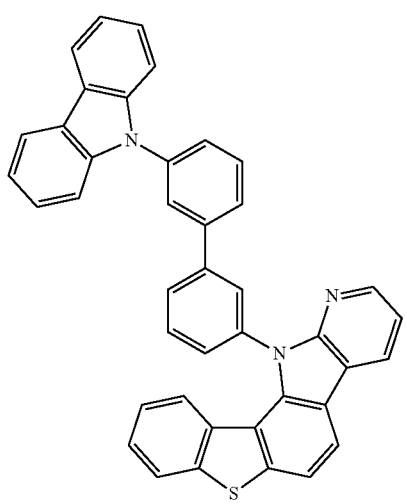
19
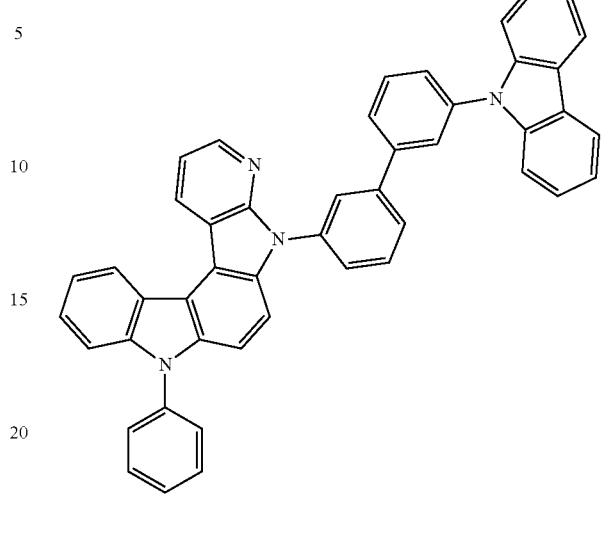
20
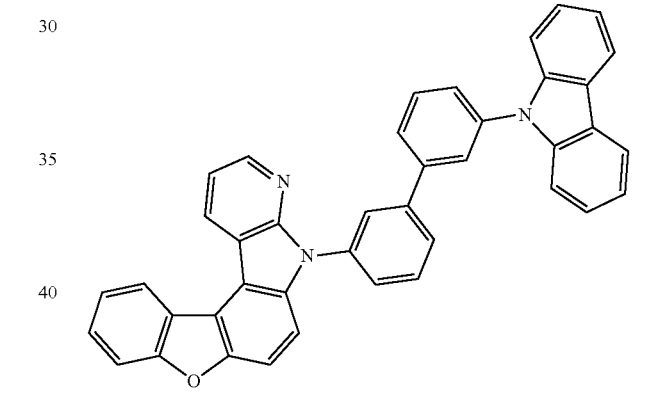
21
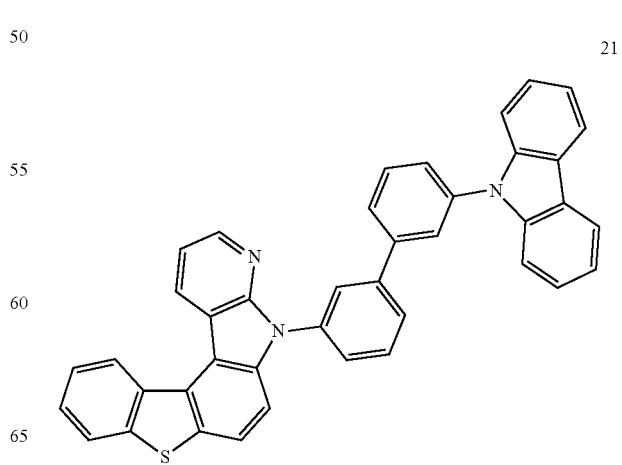

22
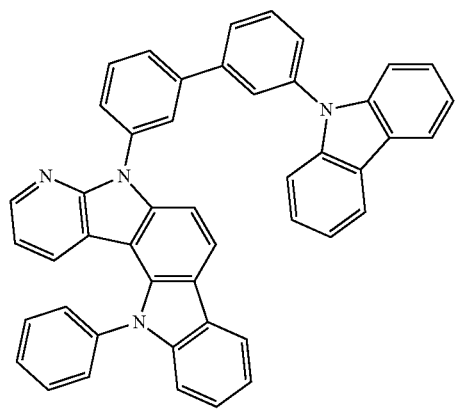
23
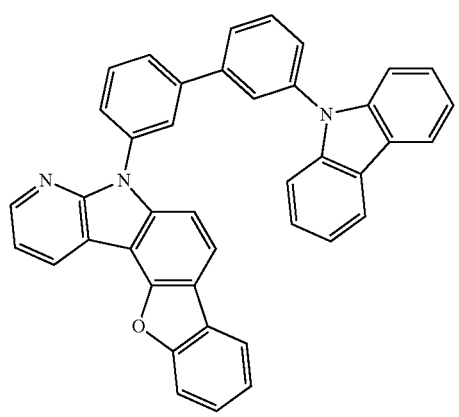
24
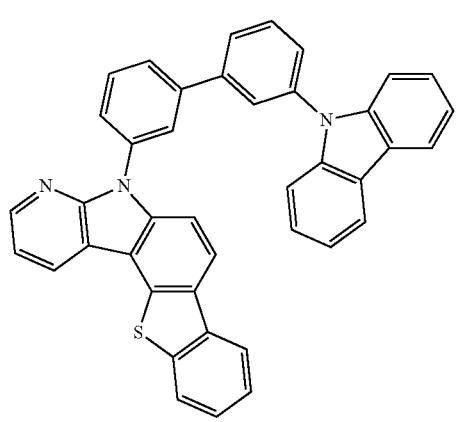
25
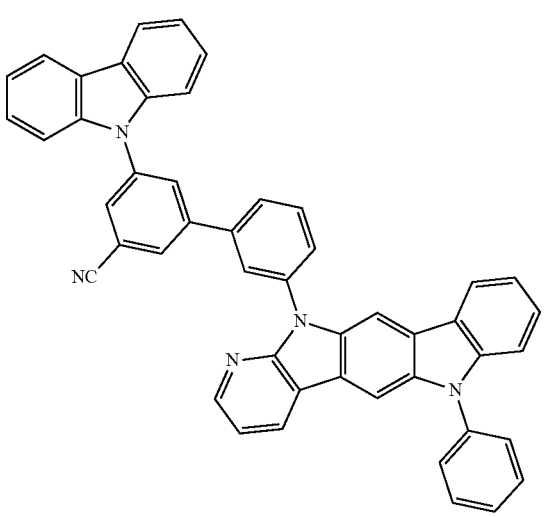
26
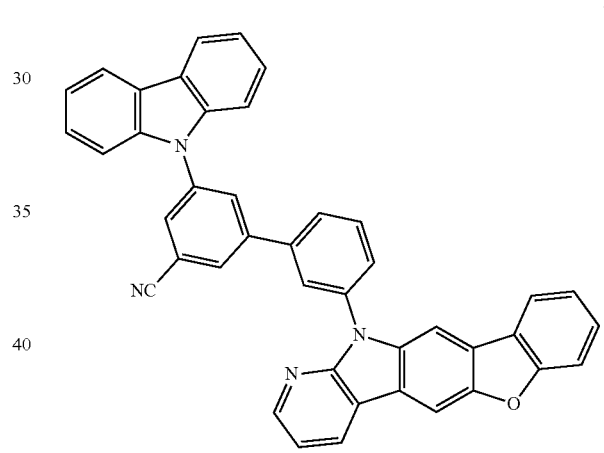
27
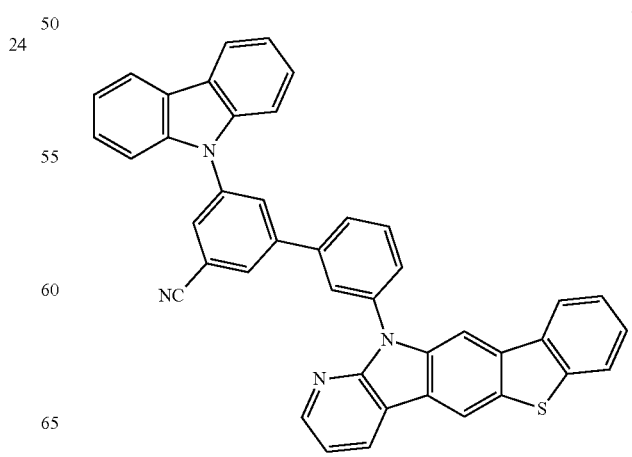

28
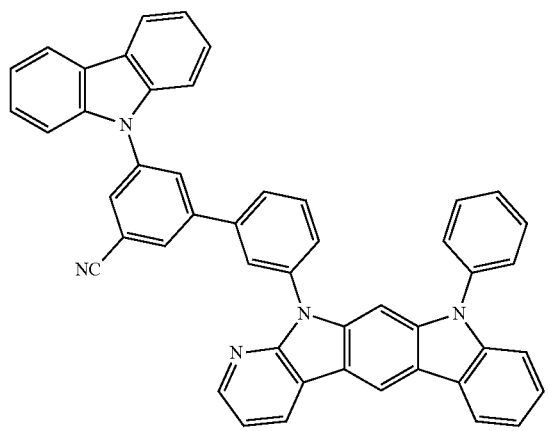
29
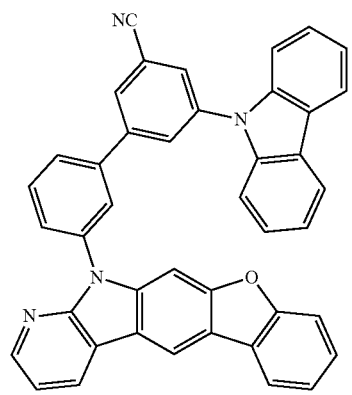
30
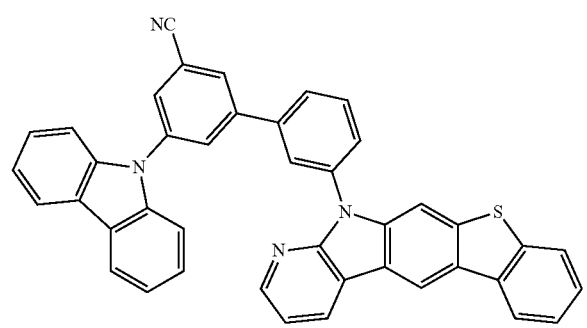
31
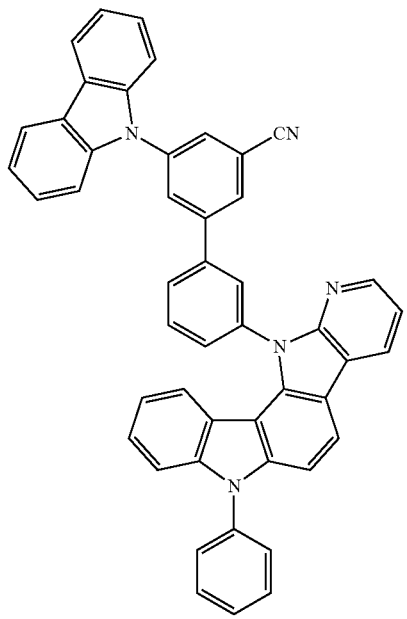
32
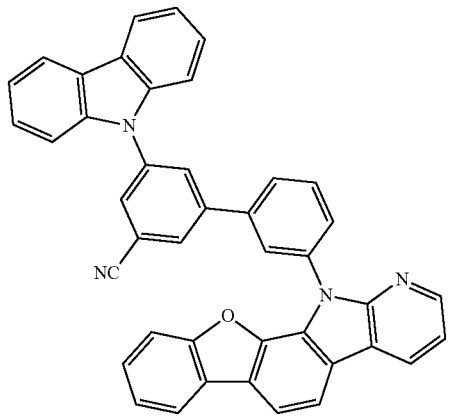
33
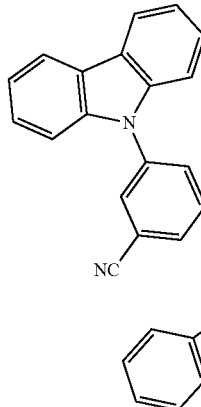
34

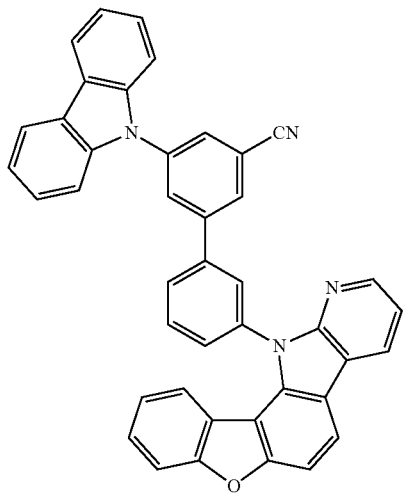
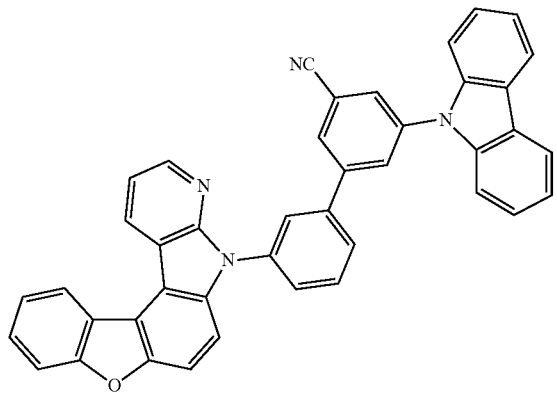
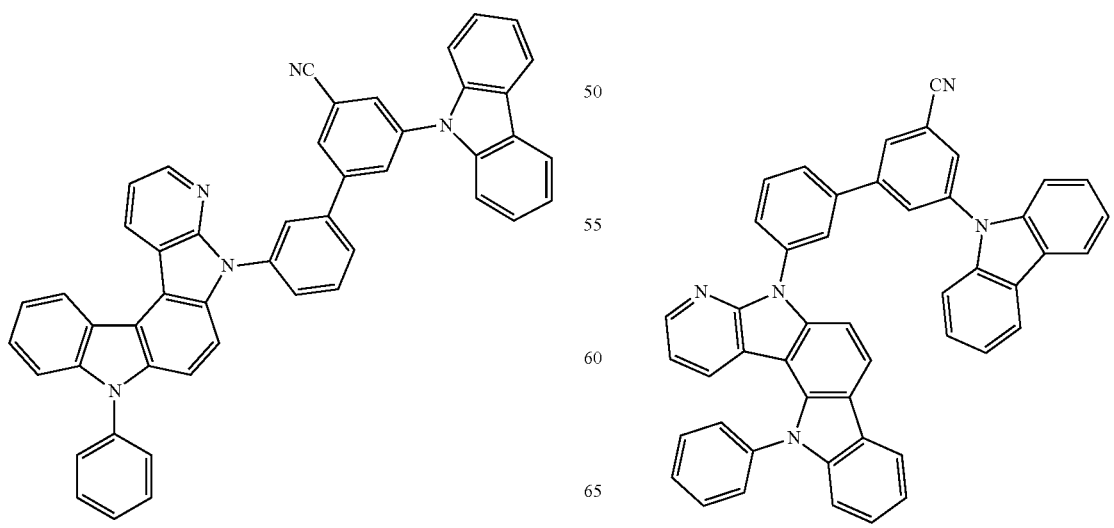

41
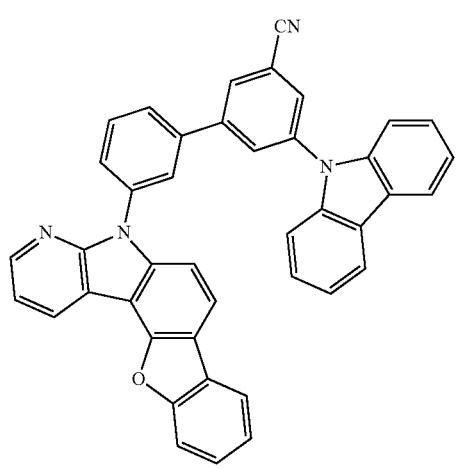
42
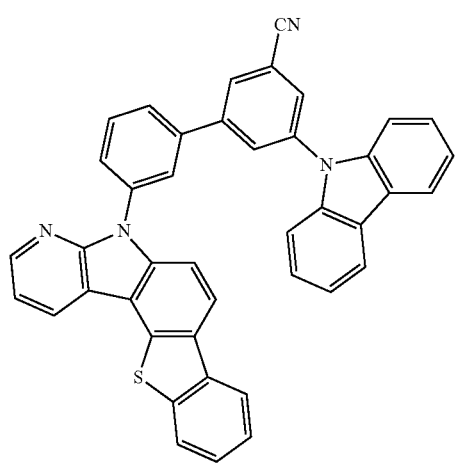
43
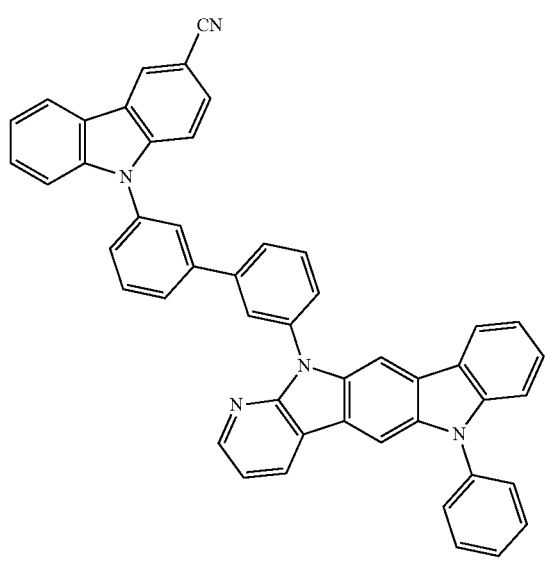
44
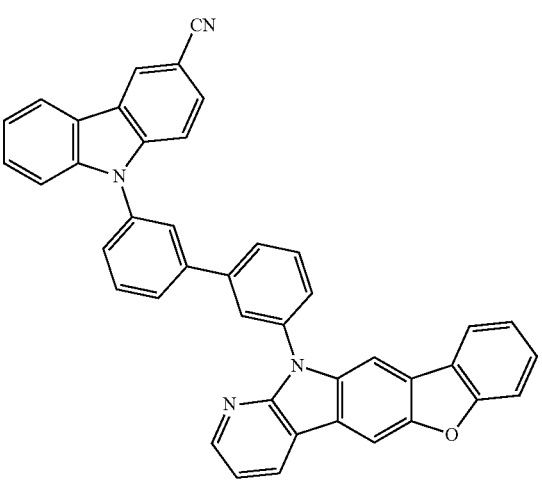
45
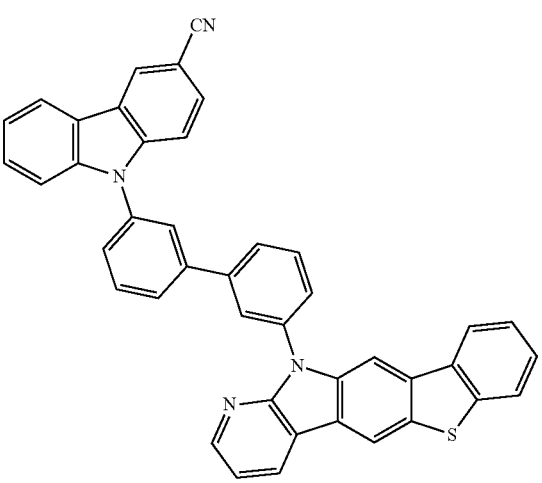
46
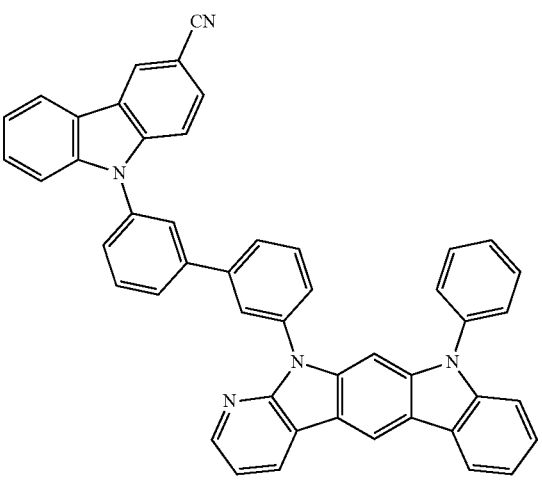

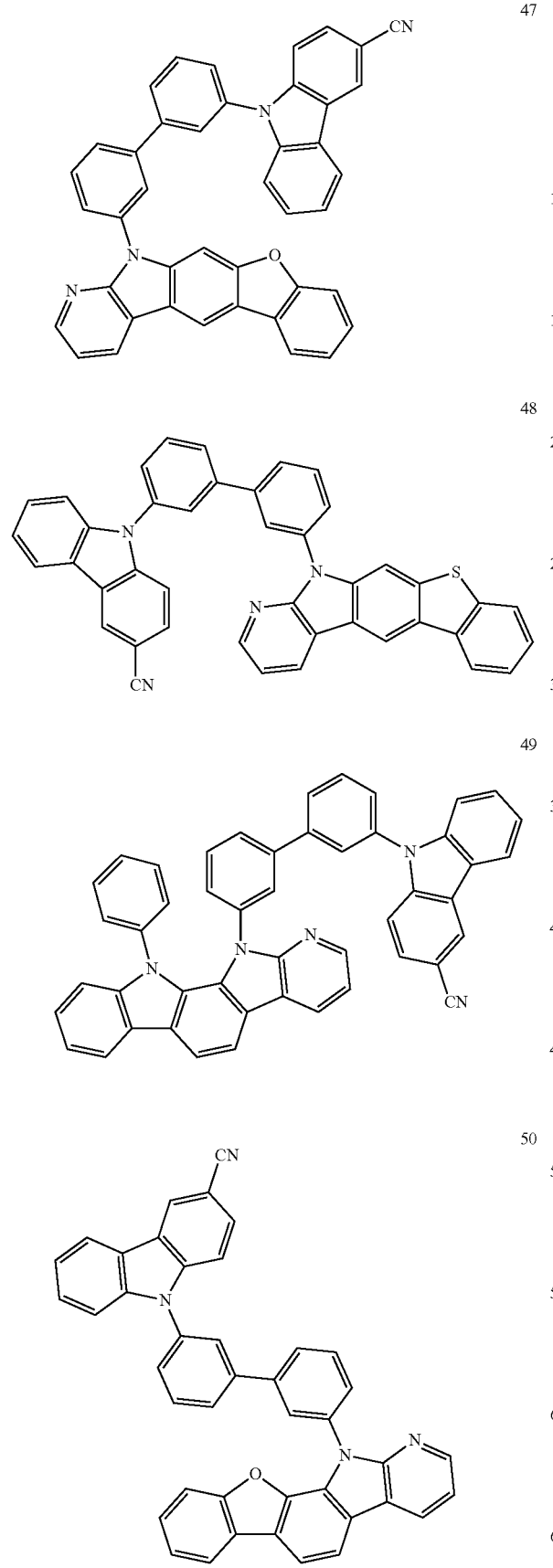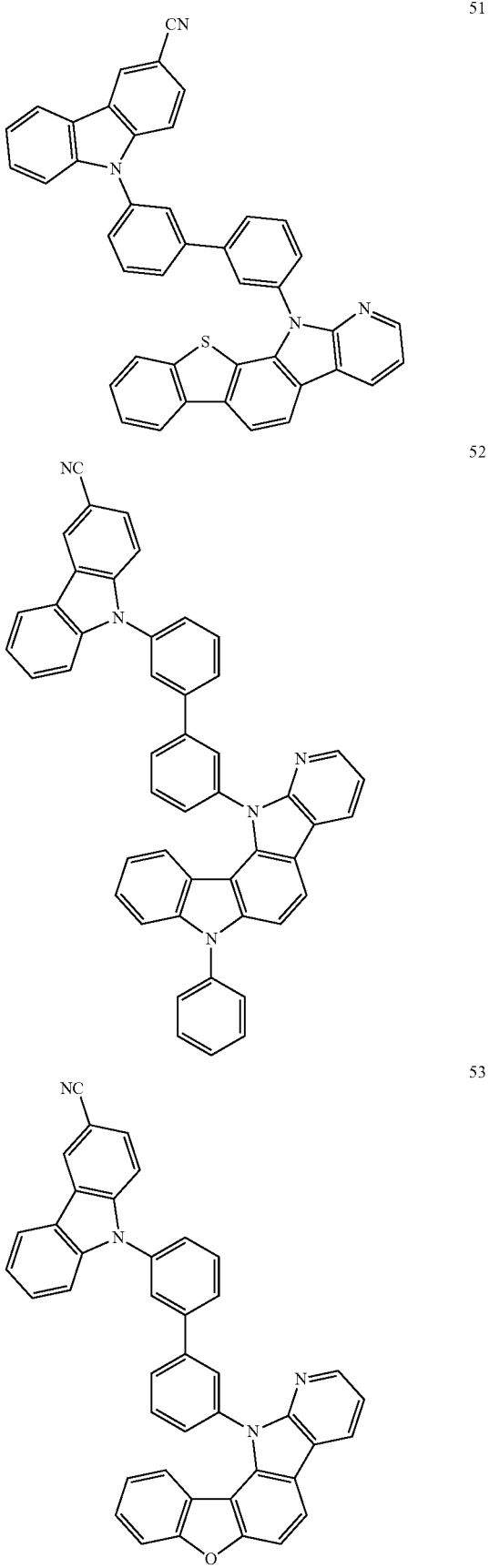

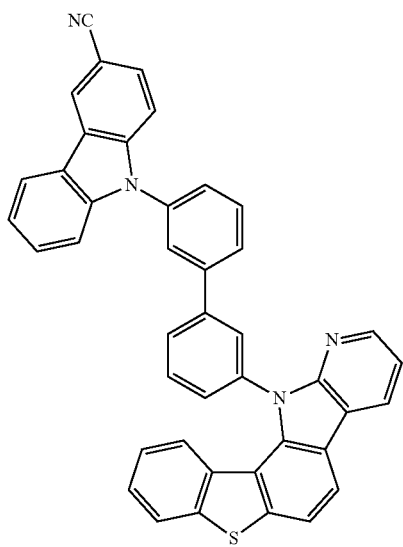
54
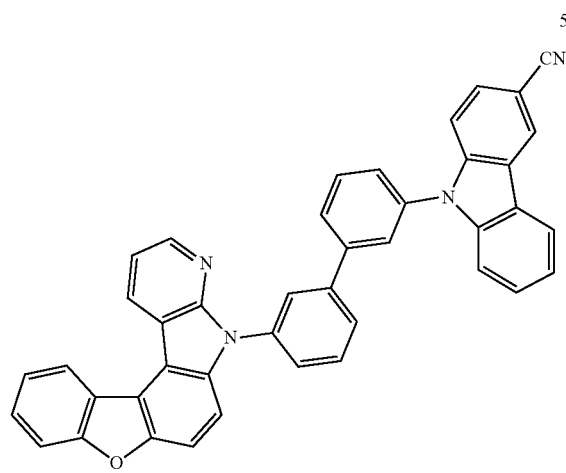
55
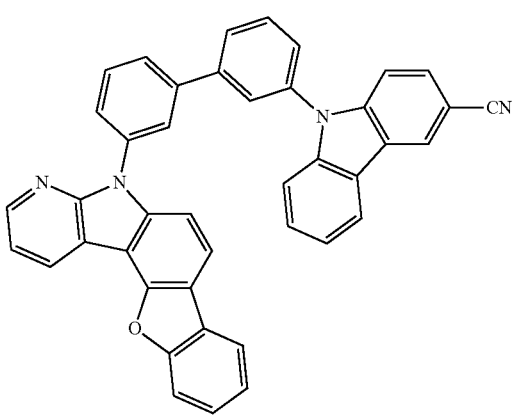
56
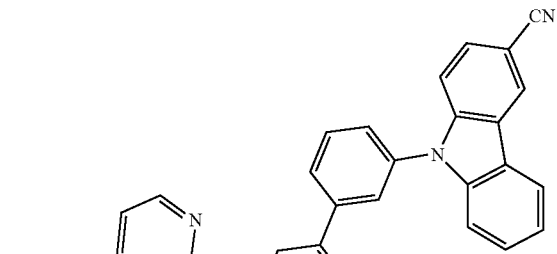
57
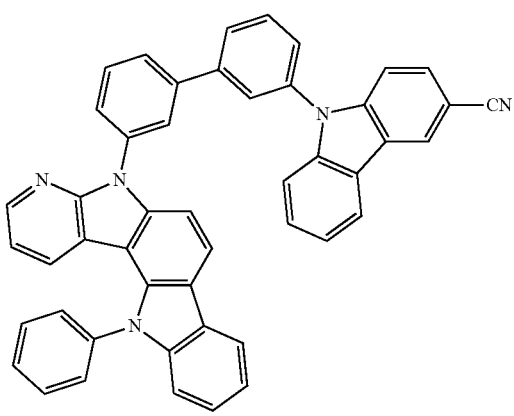
58
59

60
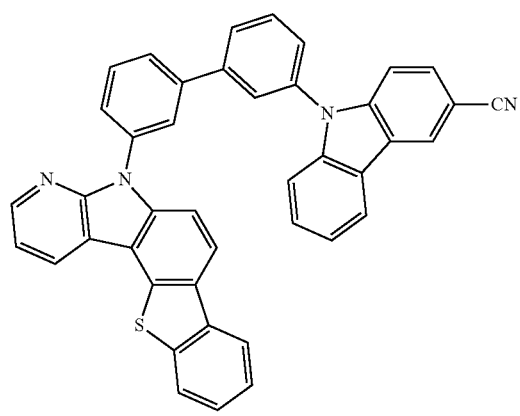
63
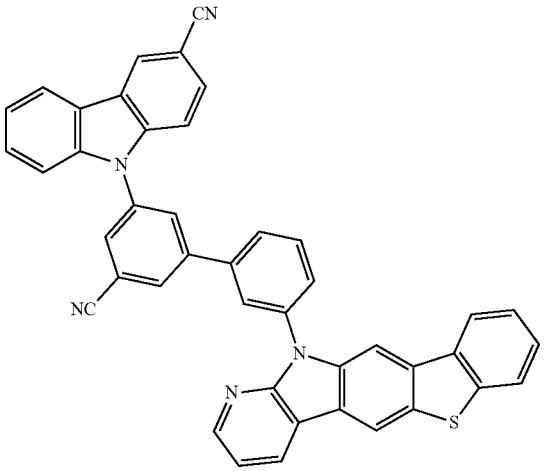
61
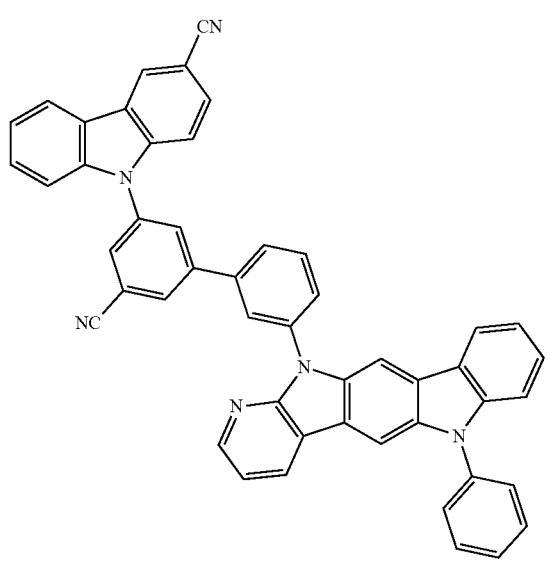
64
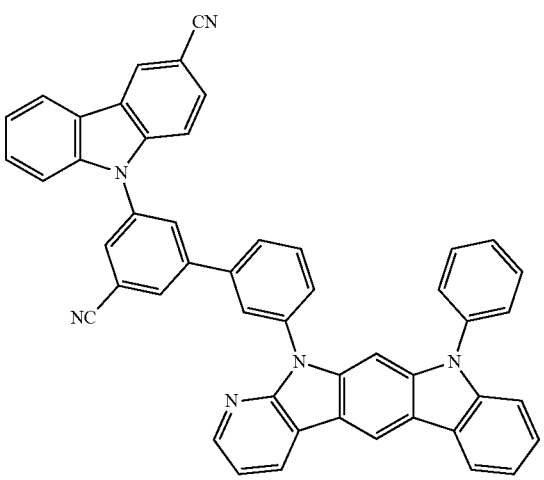
62
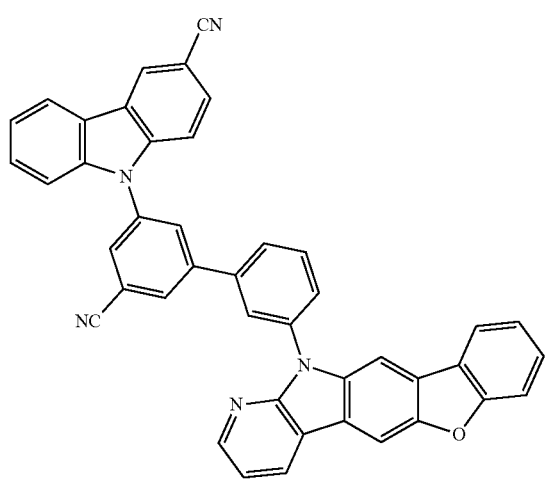
65
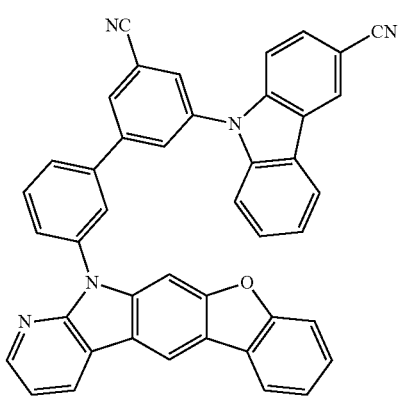

66
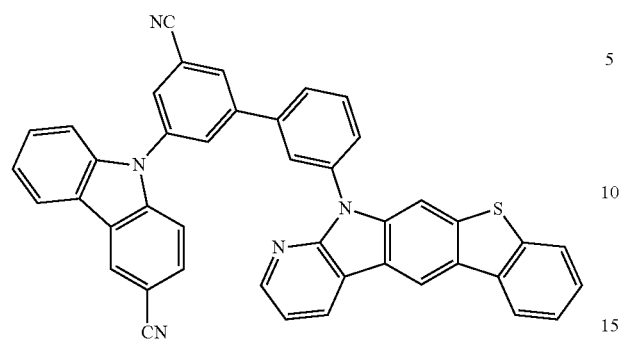
67
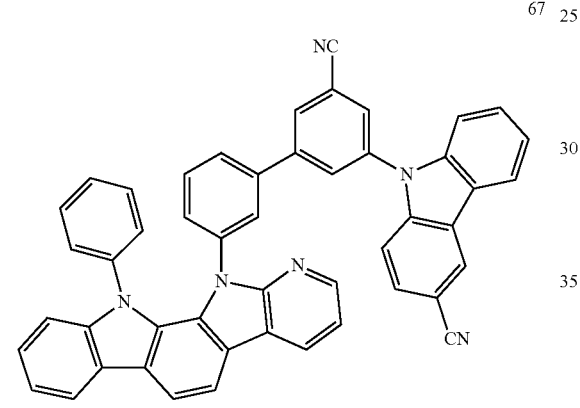
68
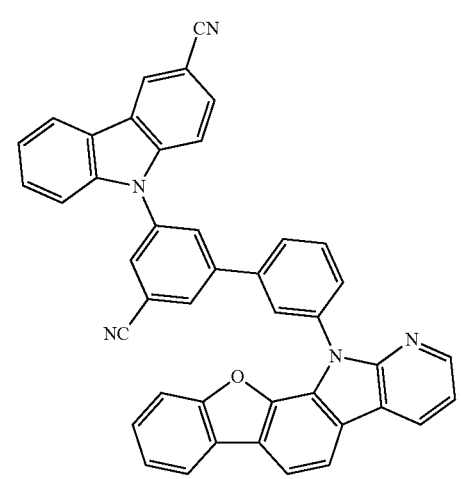
69
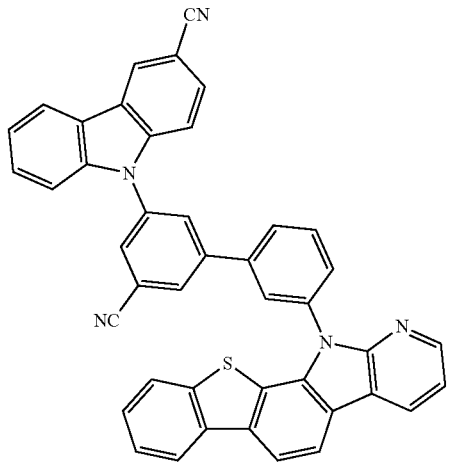
70
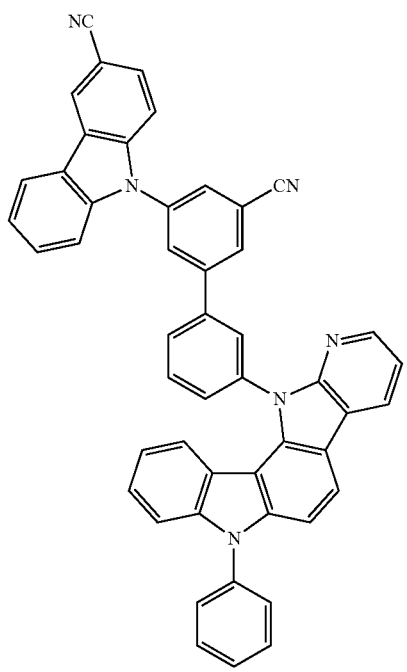
71
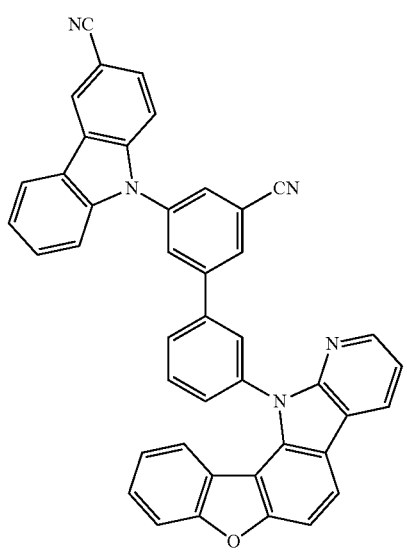

72
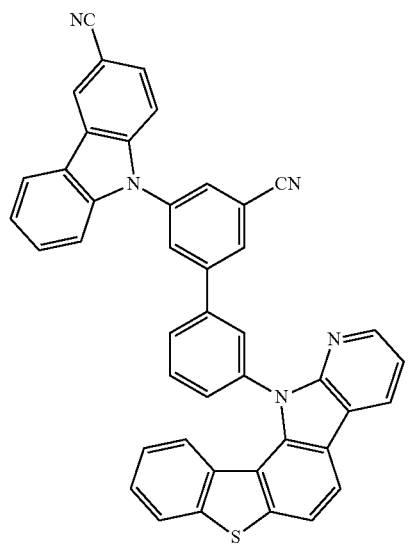
75
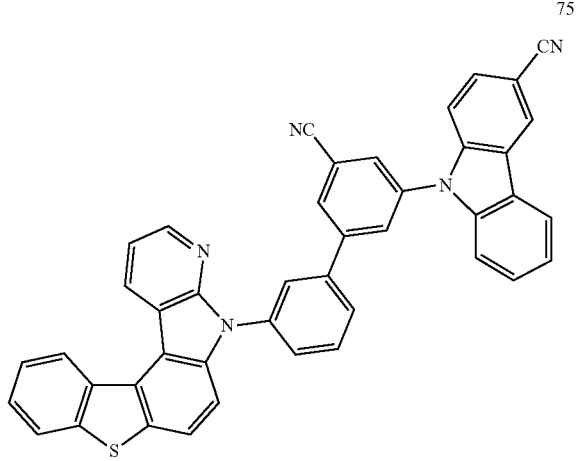
73
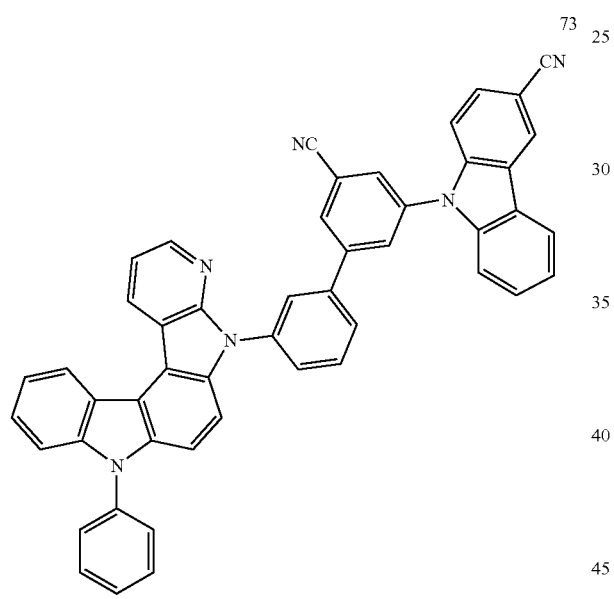
76
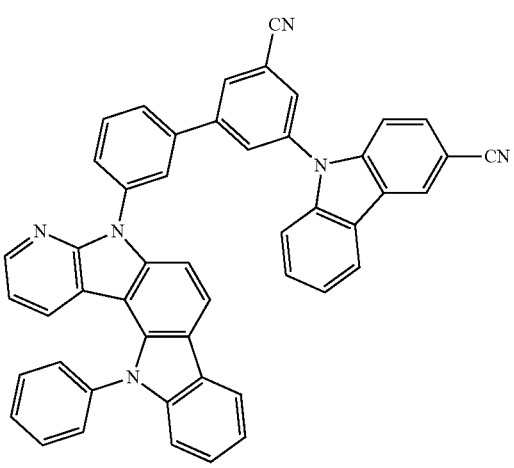
74
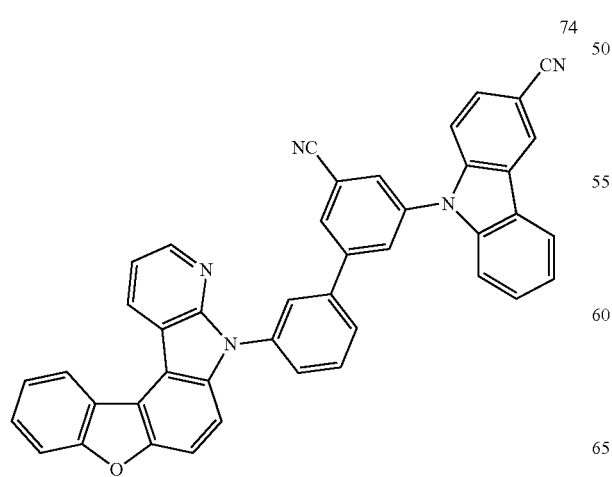
77
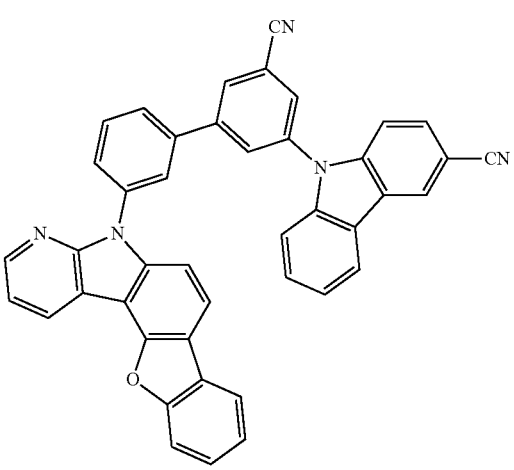

78
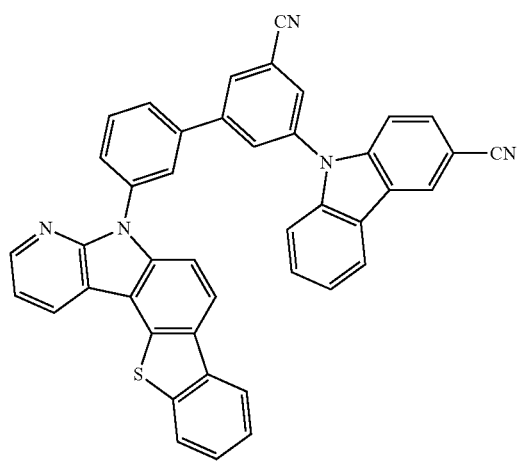
79
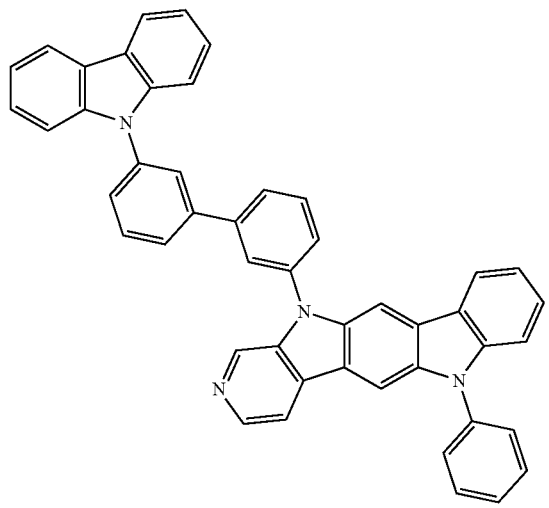
80
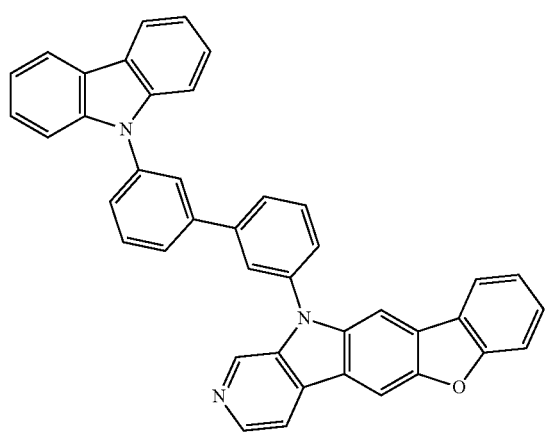
81
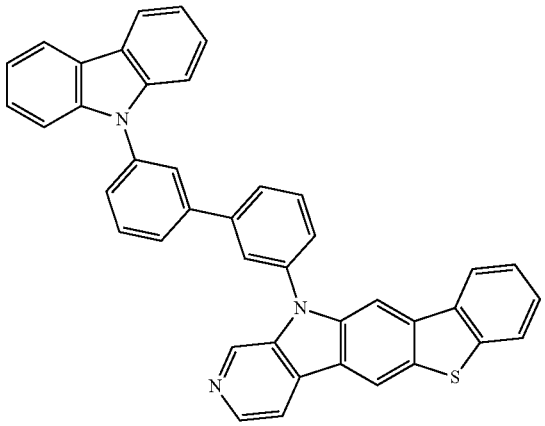
82
83
84
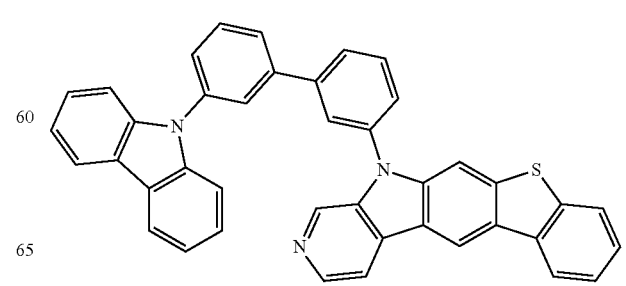

85
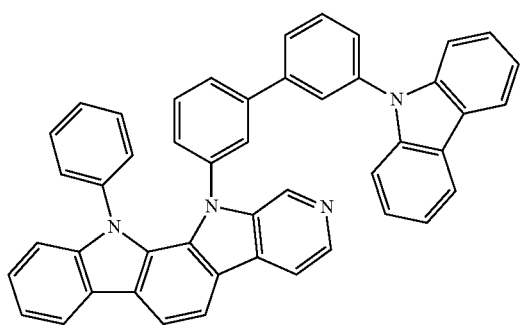
86
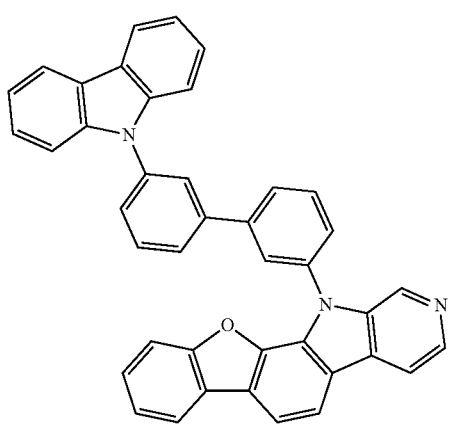
87
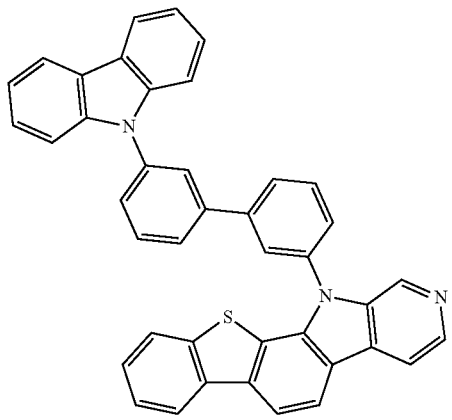
88
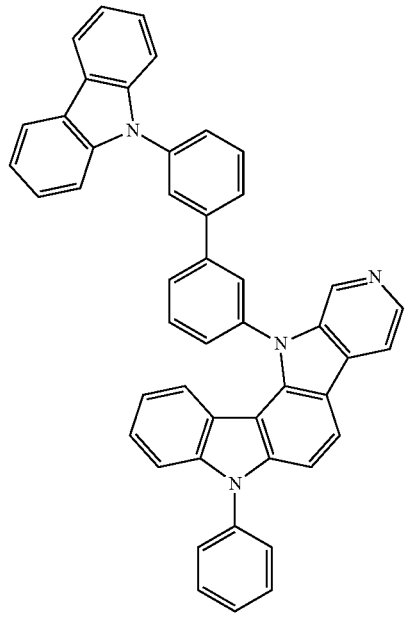
89
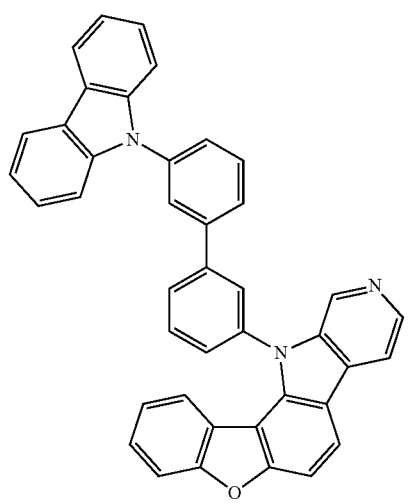
90
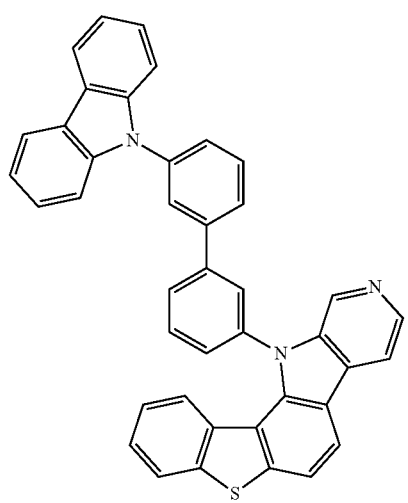

-continued
91
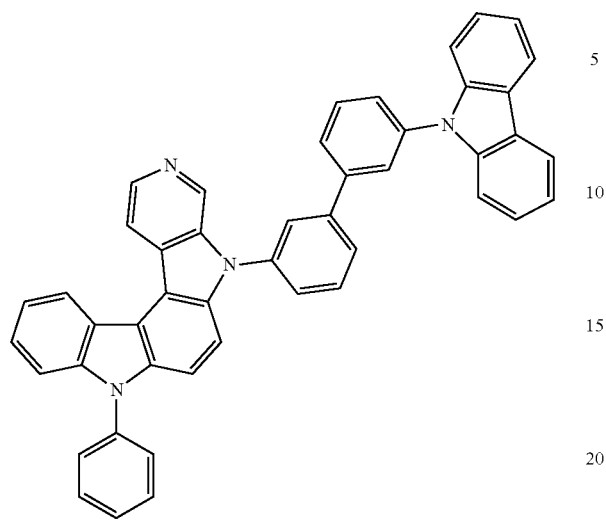
92
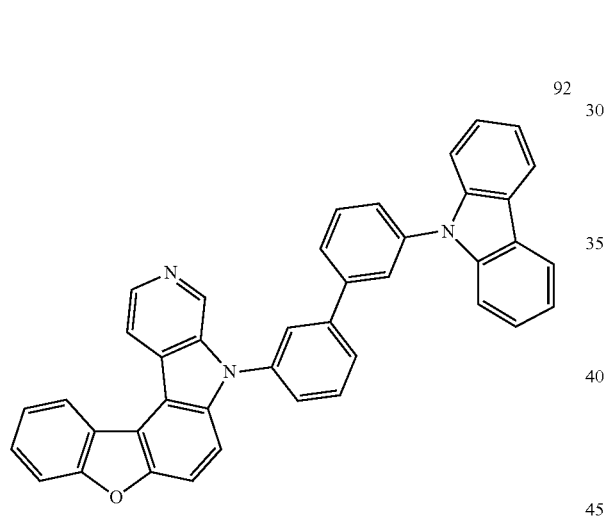
93
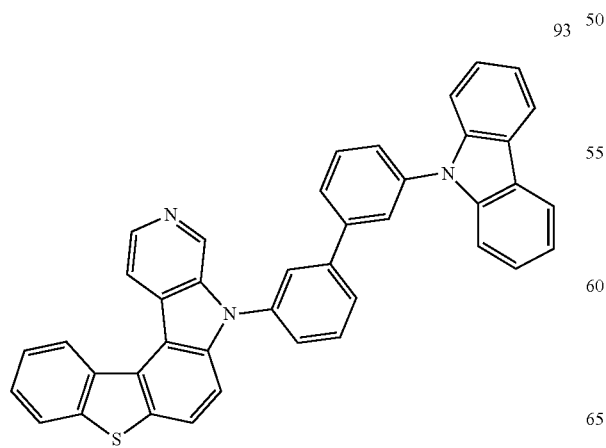
-continued
94
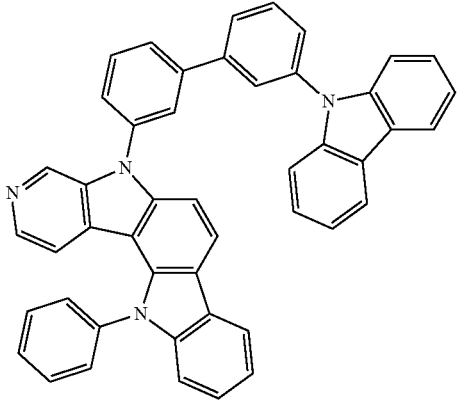
95
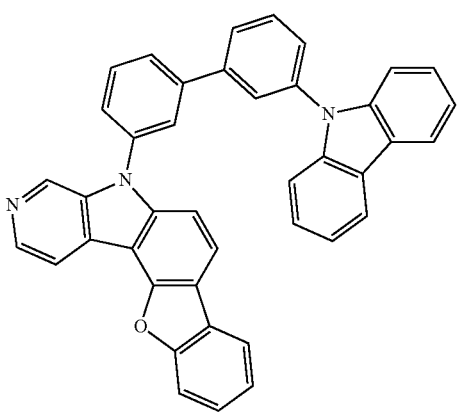
96
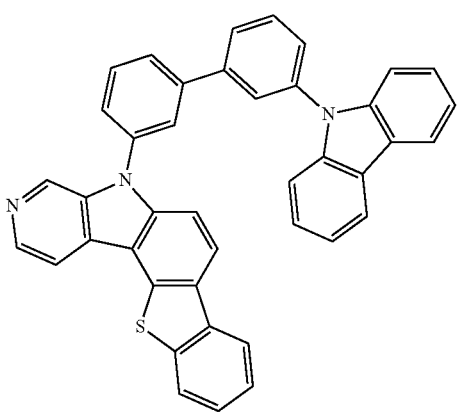

-continued
97
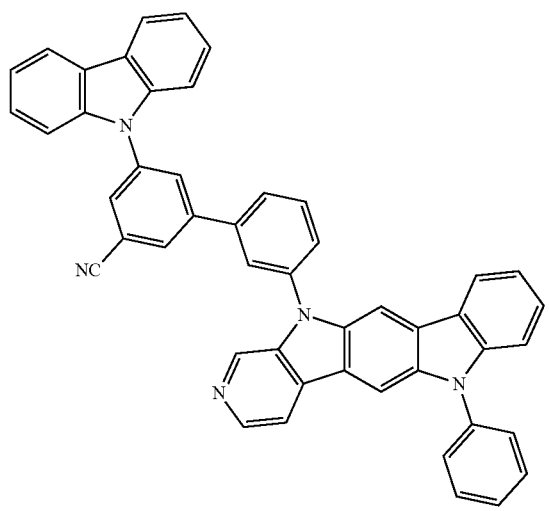
98
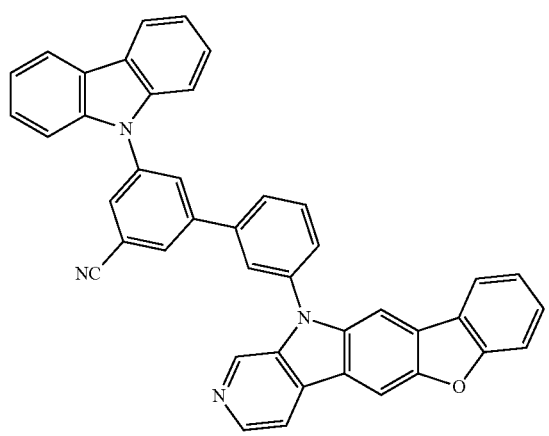
99
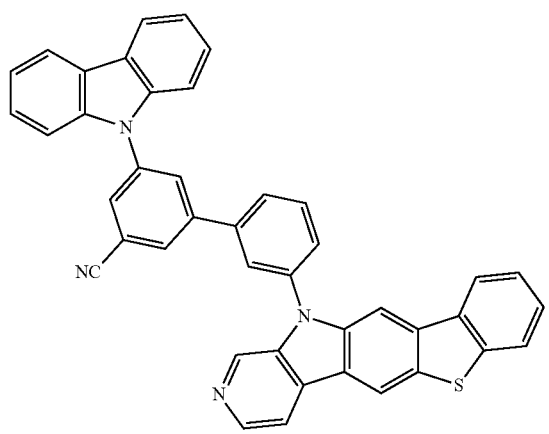
-continued
100
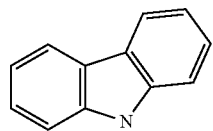
101
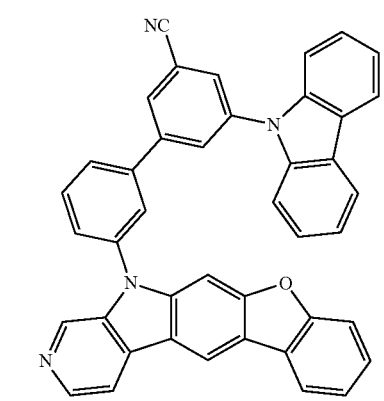
102
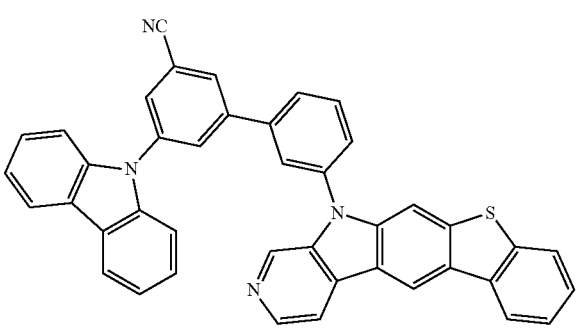
103
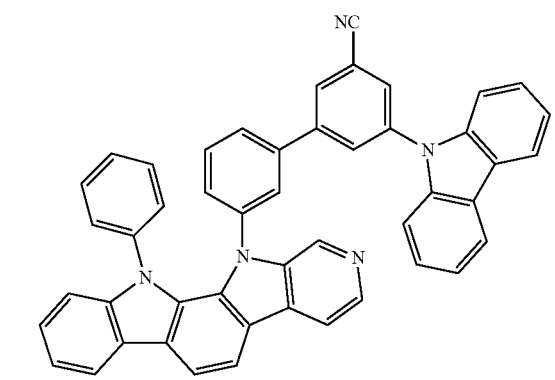

104
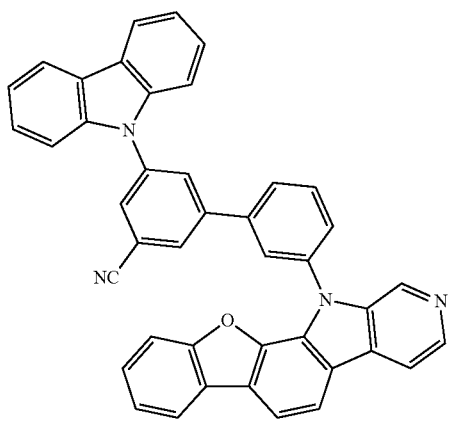
105
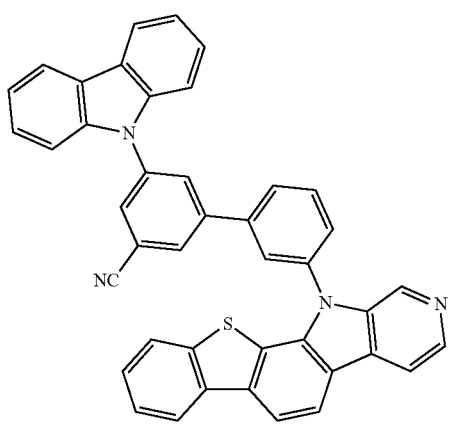
106
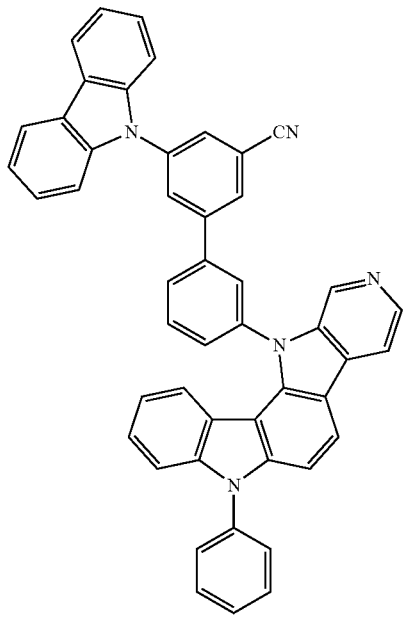
107
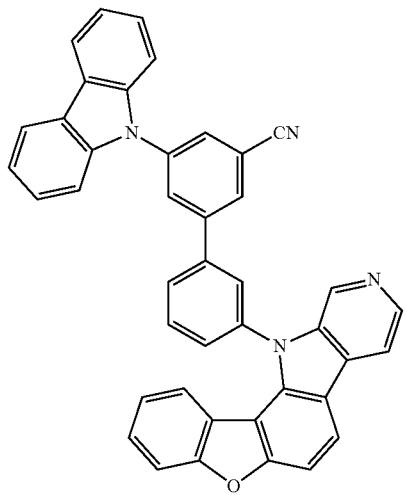
108
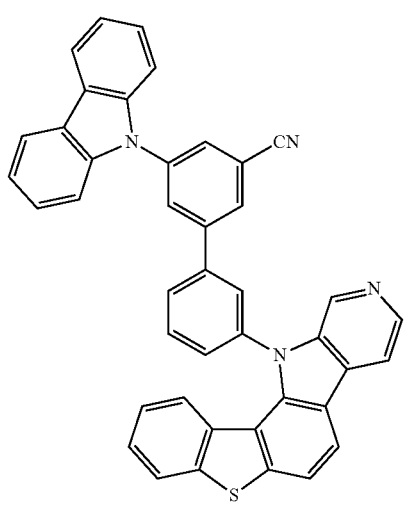
109
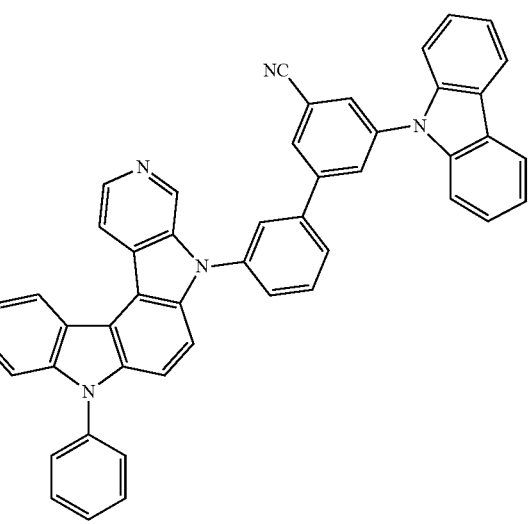

110
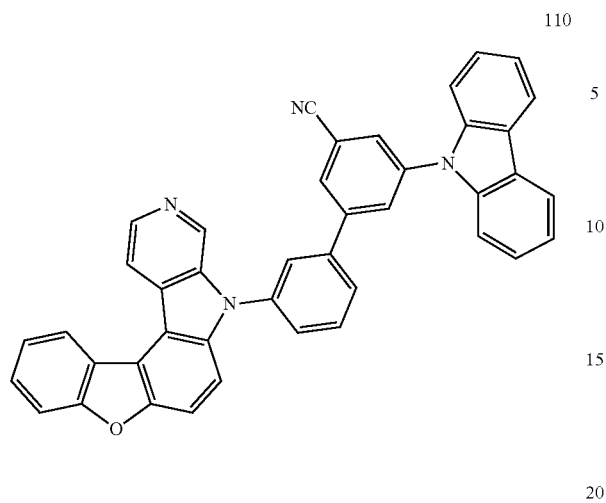
111
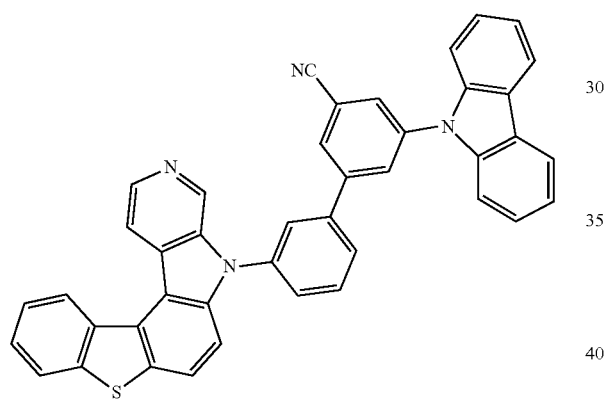
112
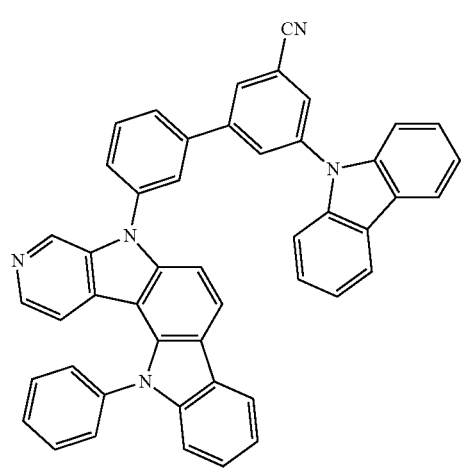
113
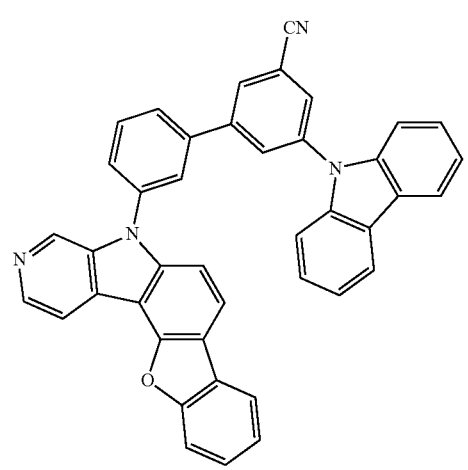
114
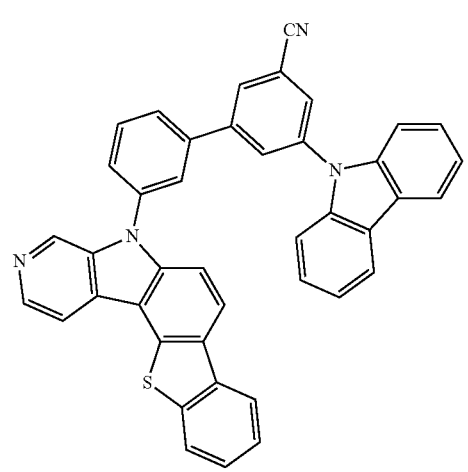
115
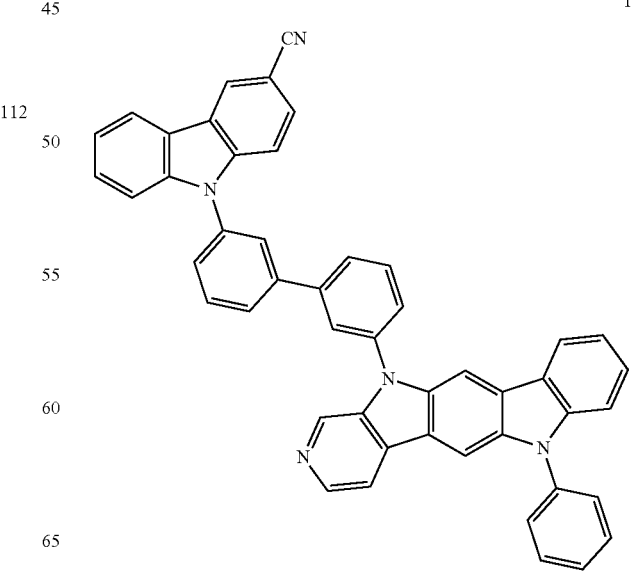

116
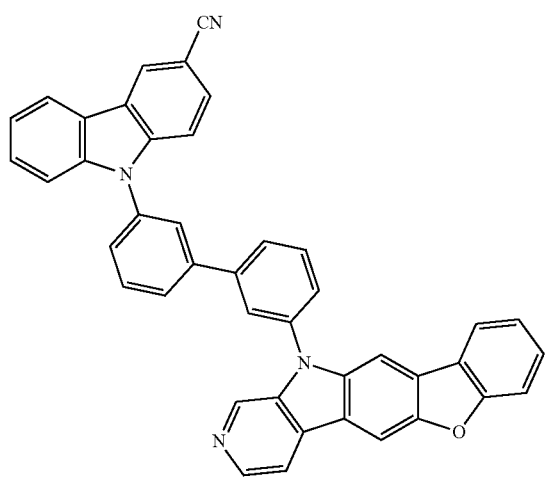
117
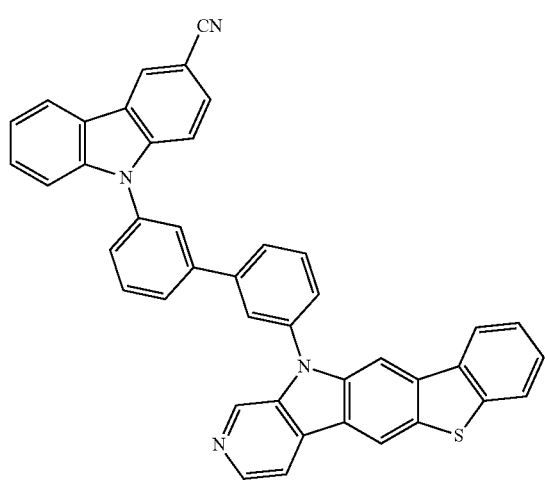
118
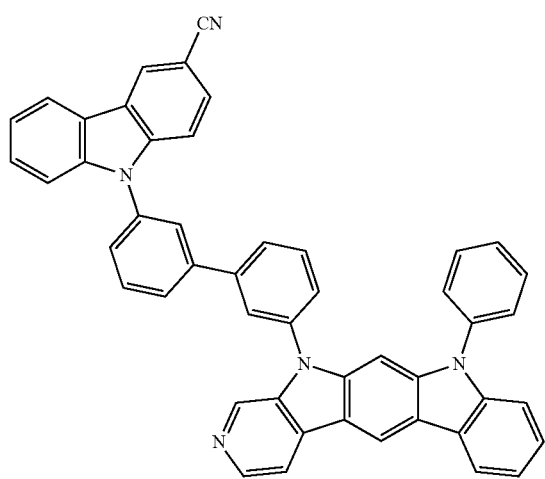
119
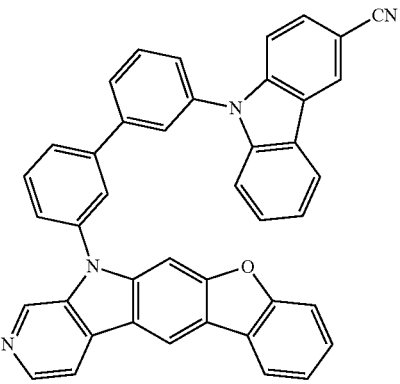
120
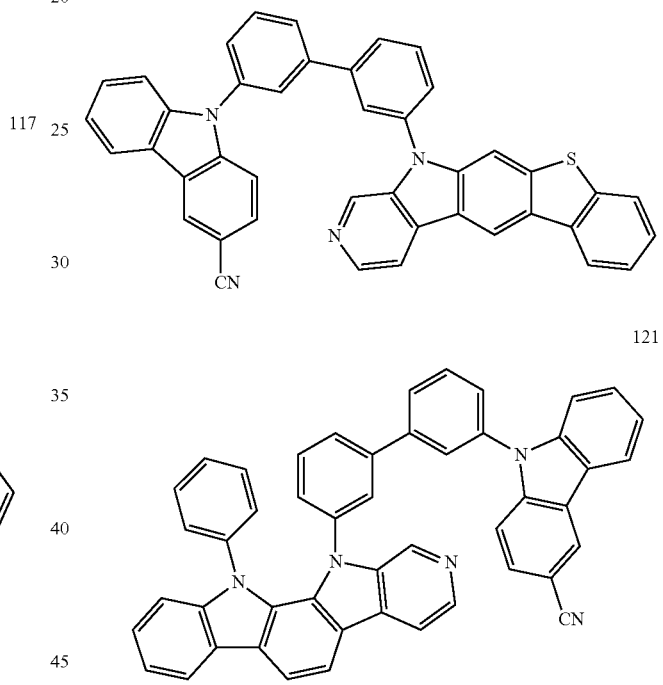
121
122
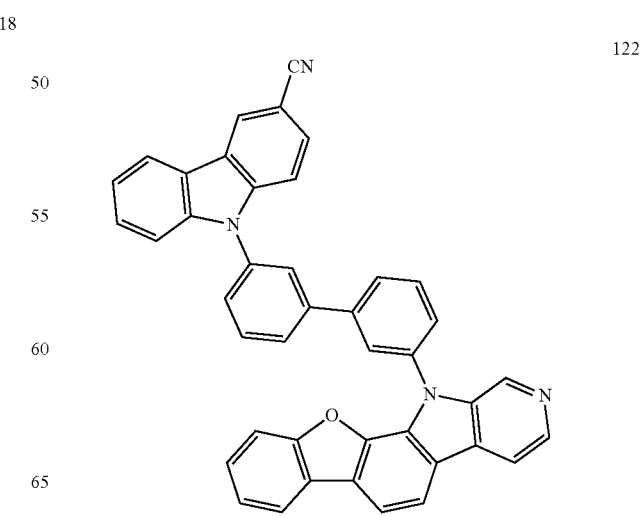

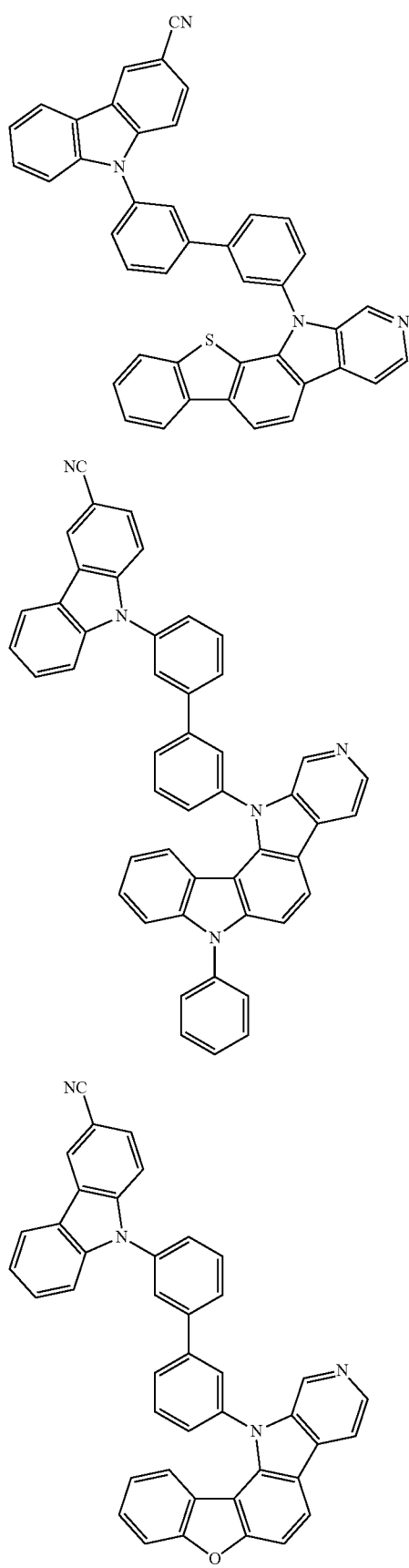
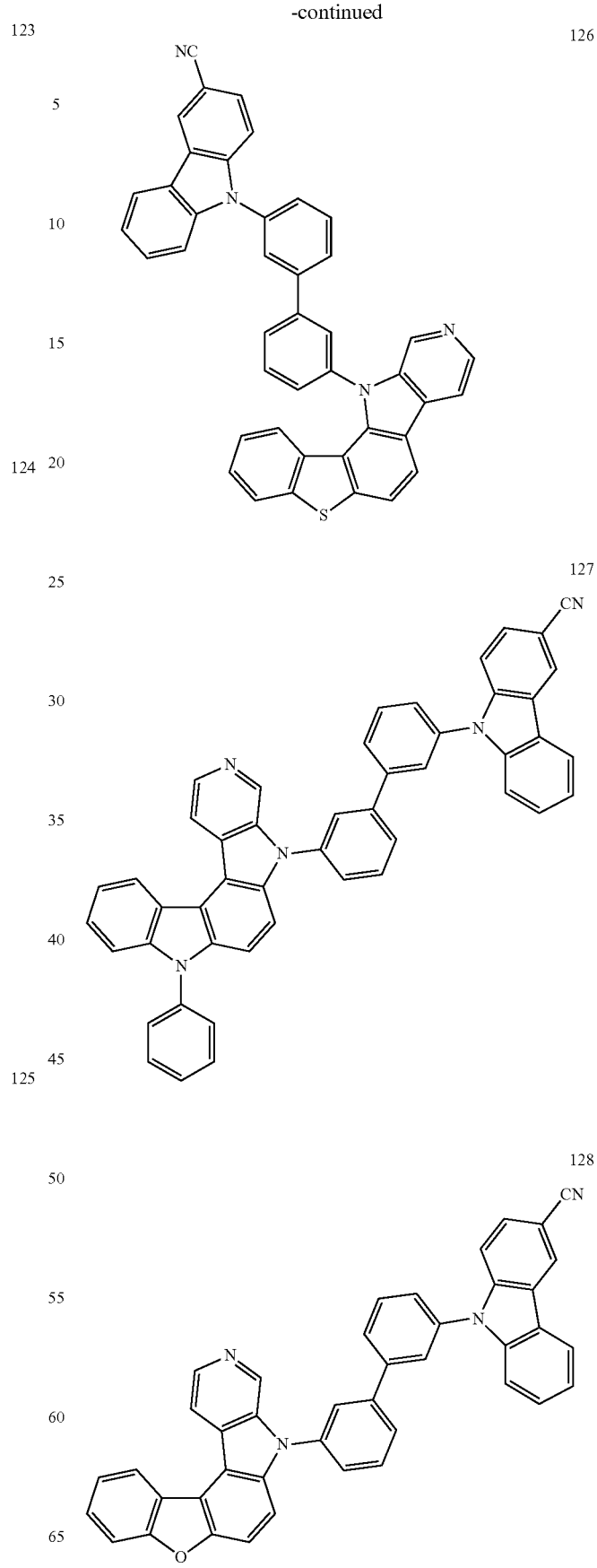

129
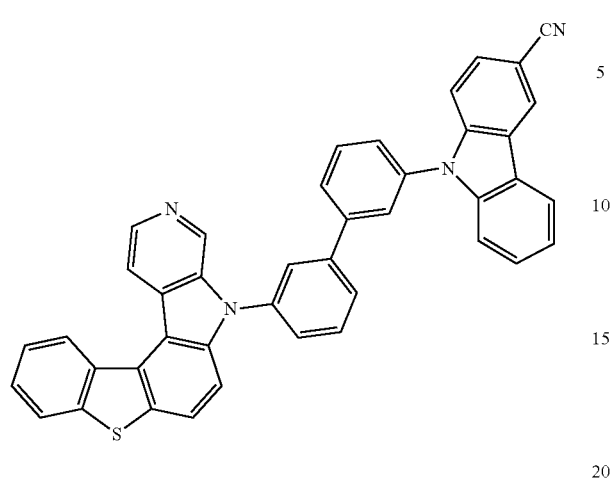
130
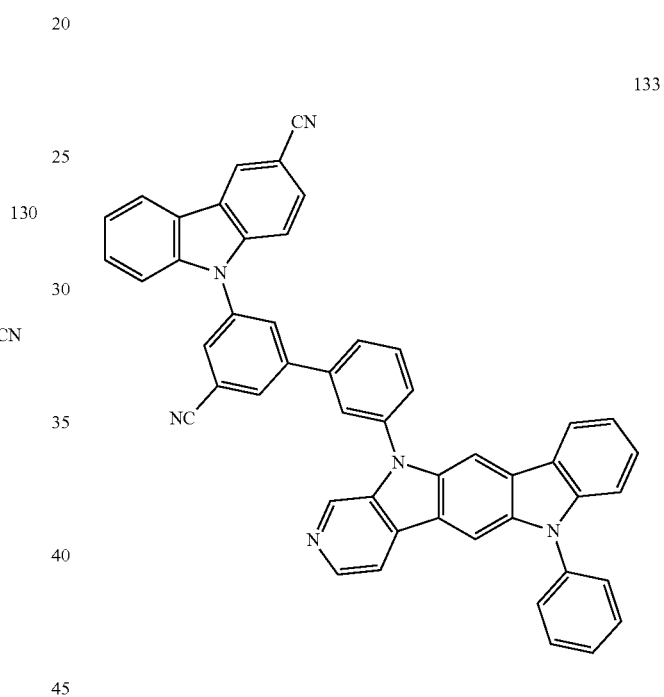
131
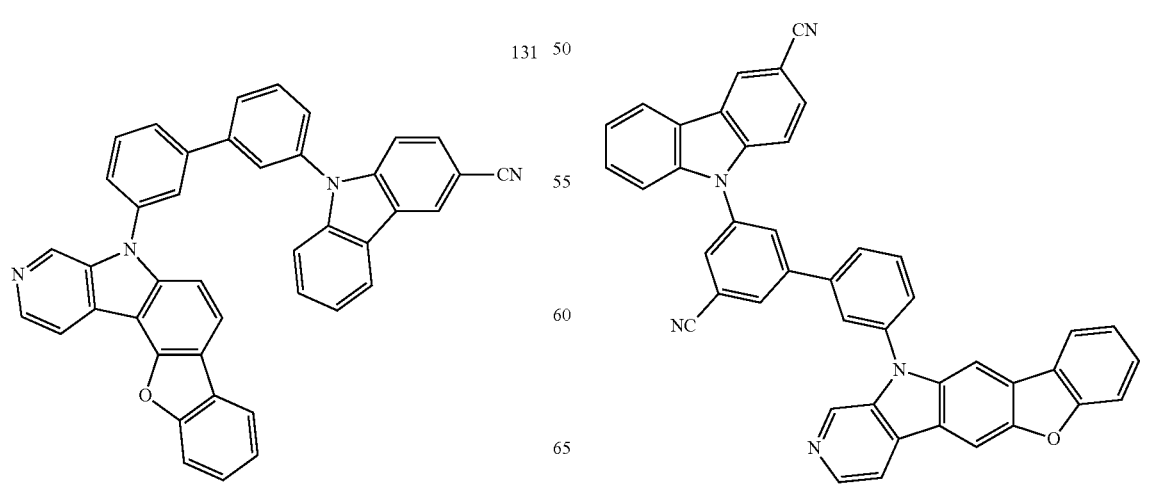
132
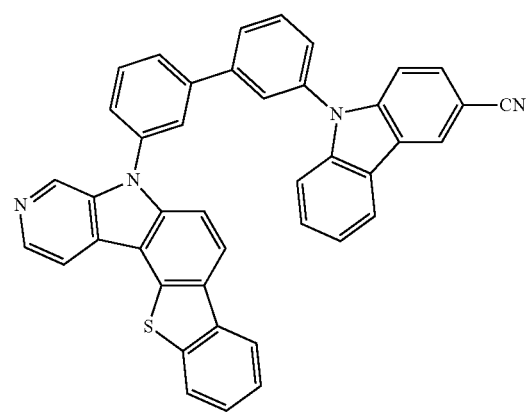
133
134

-continued
135
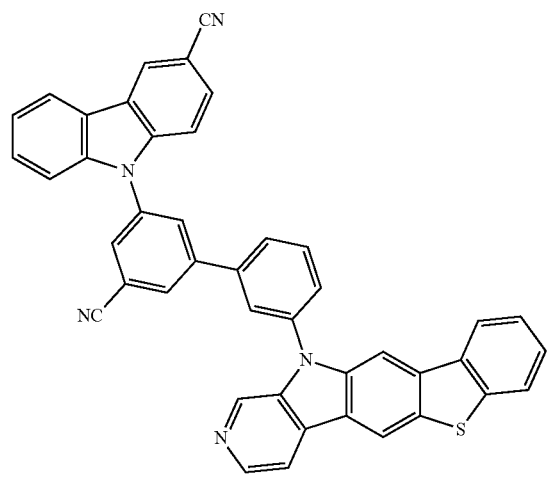
136
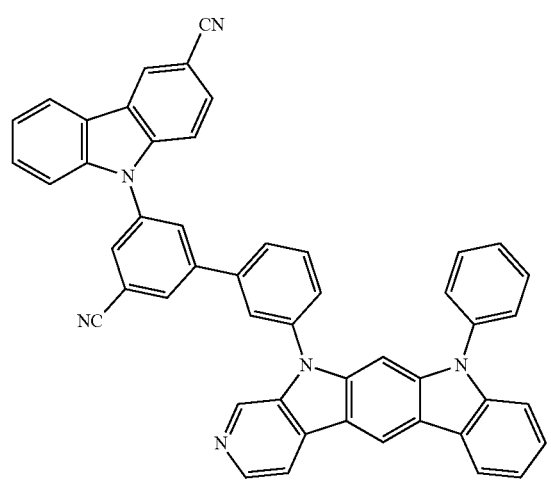
137
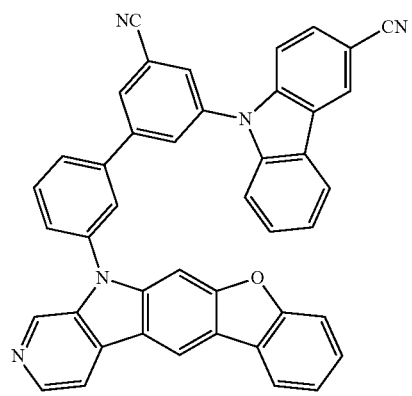
-continued
138
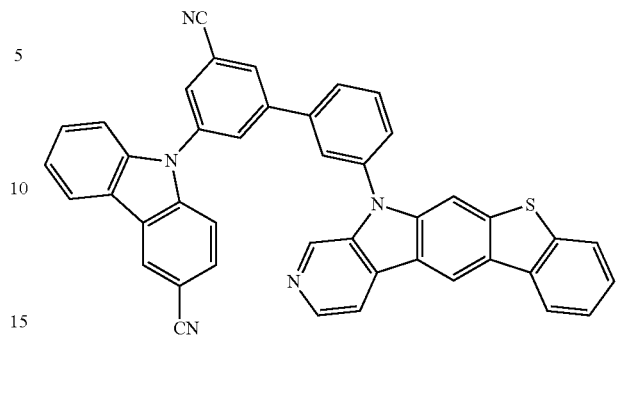
139
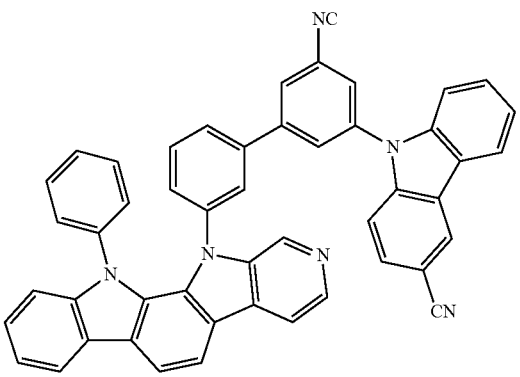
140
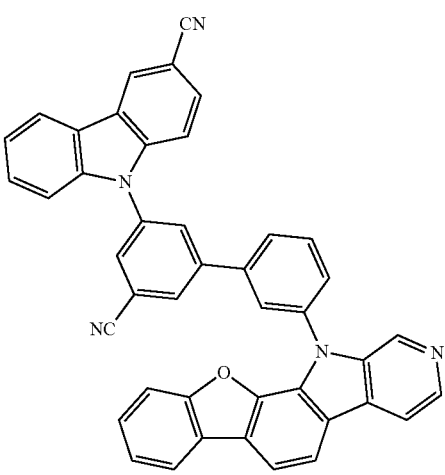

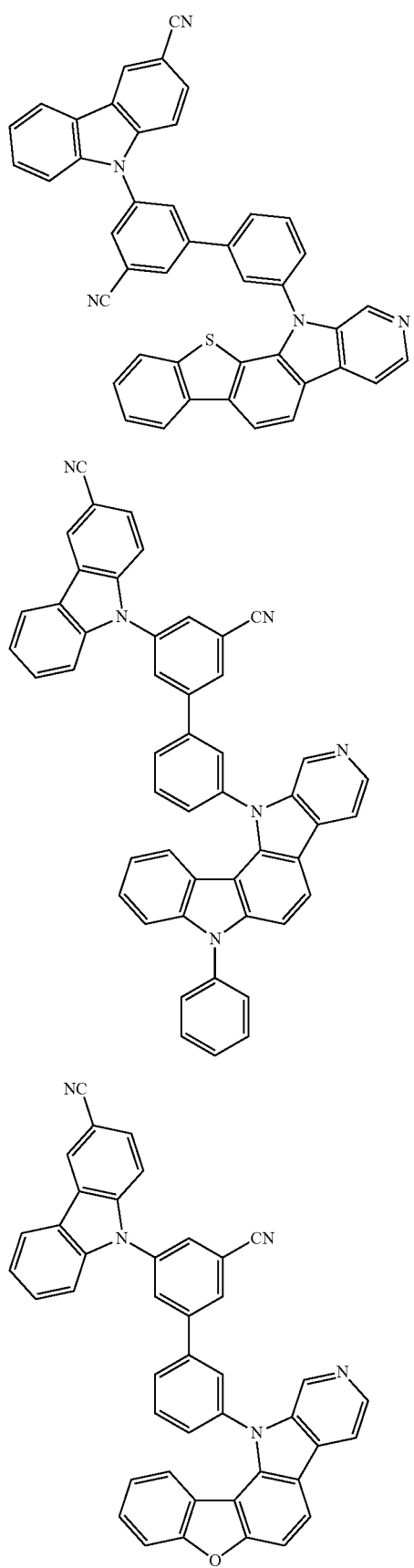
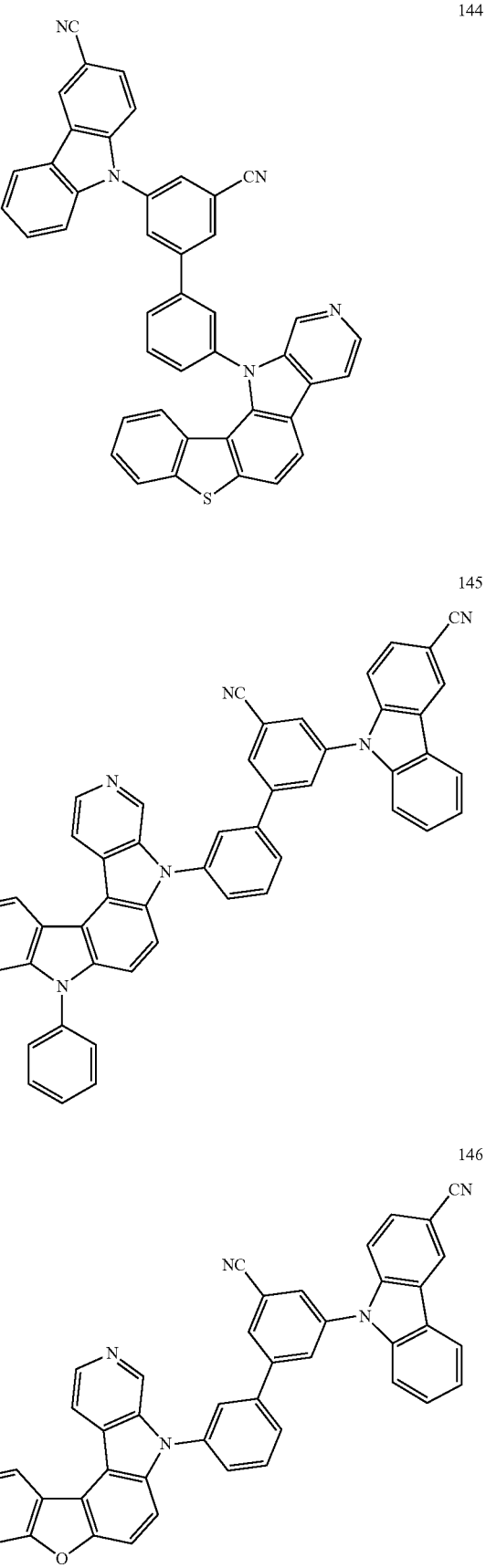

147
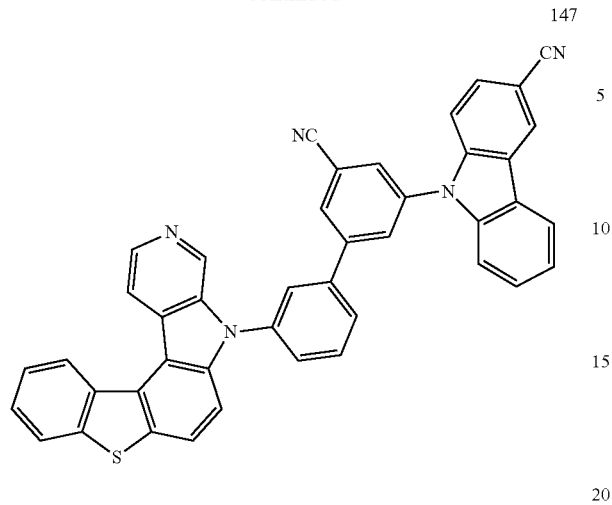
150
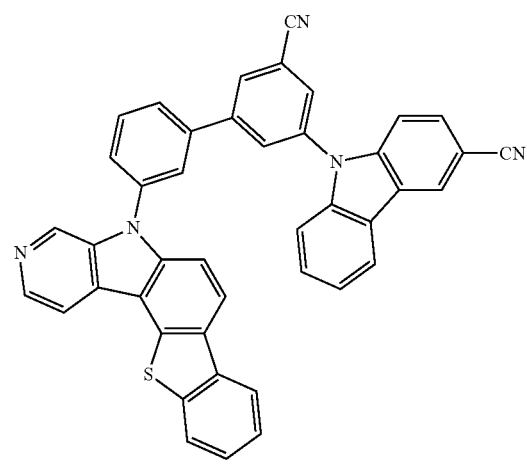
148
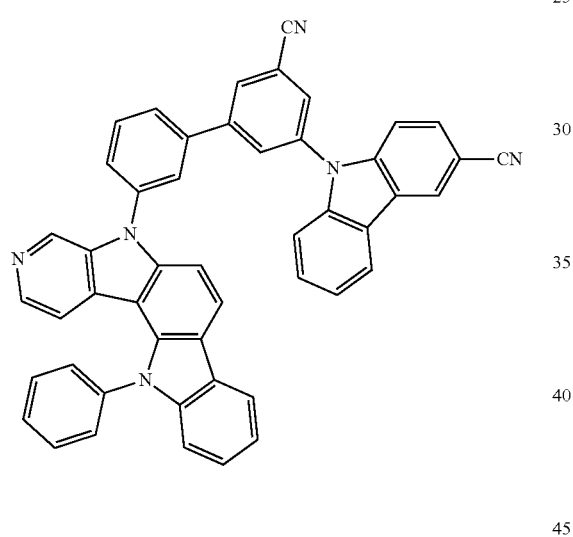
151
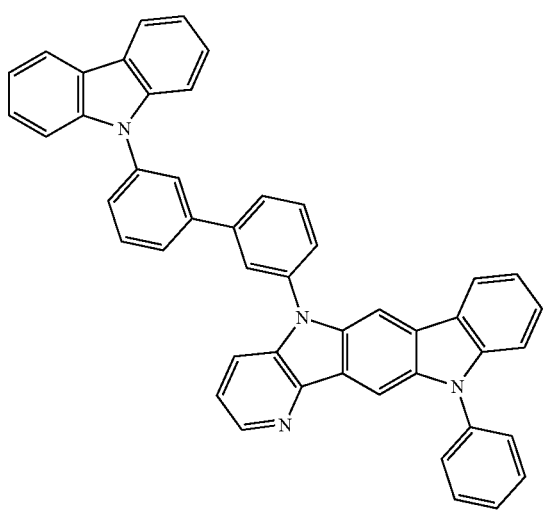
149
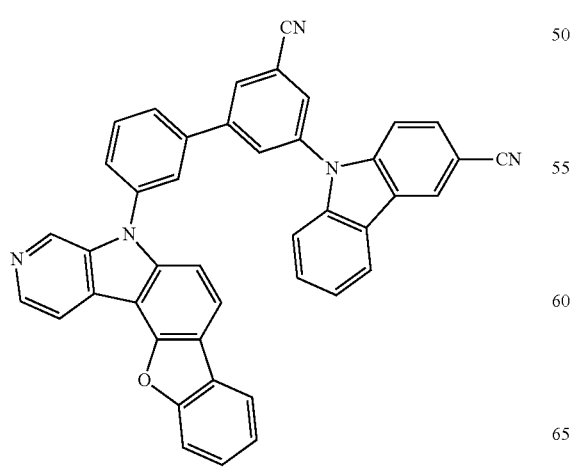
152
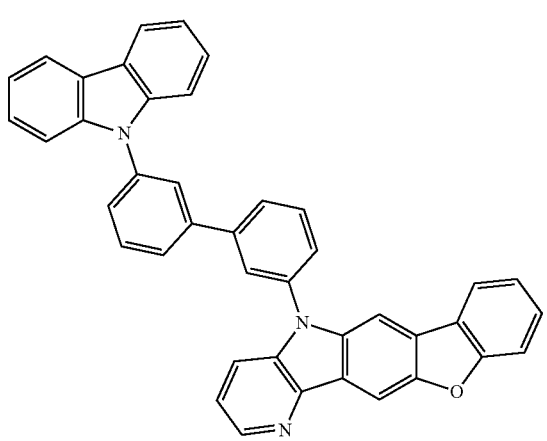

153
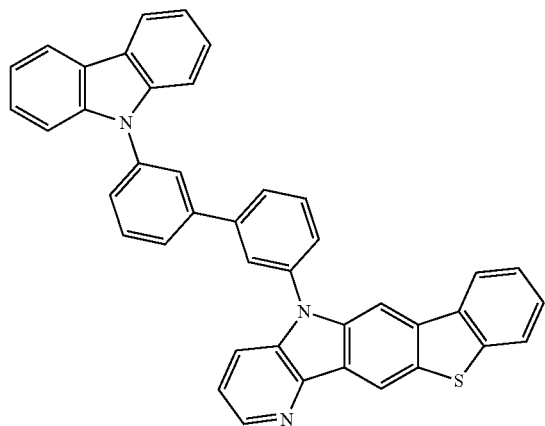
154
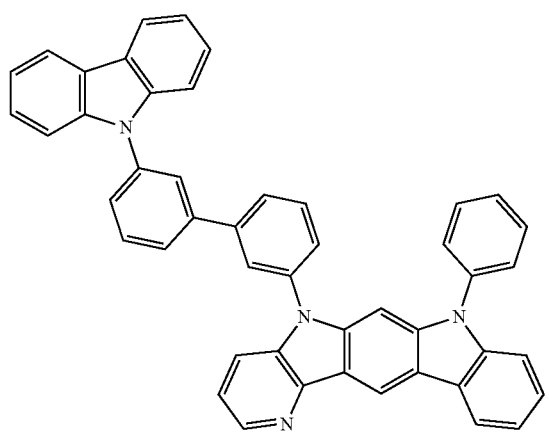
155
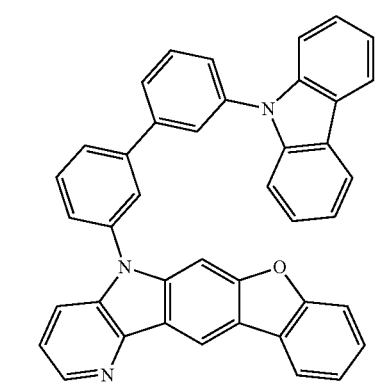
156
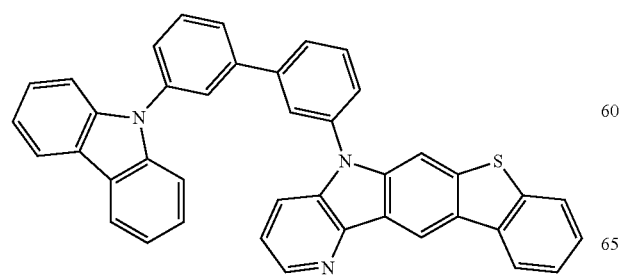
157
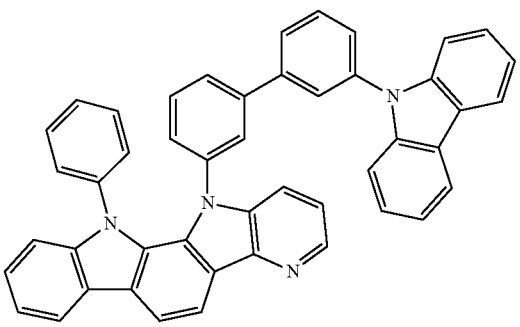
158
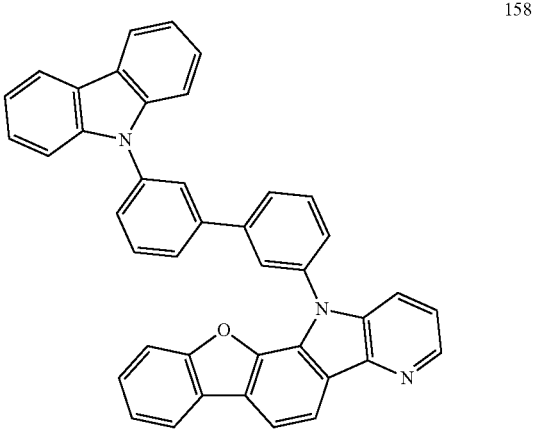
159
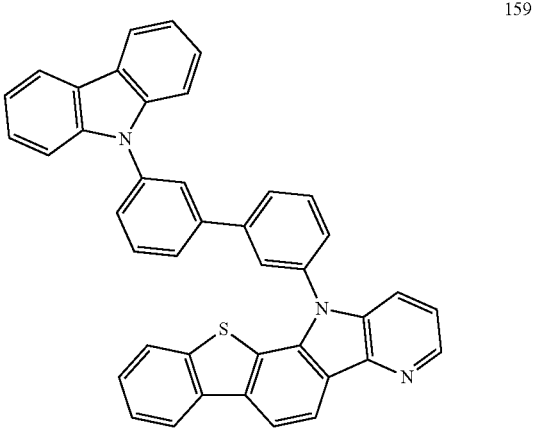

160
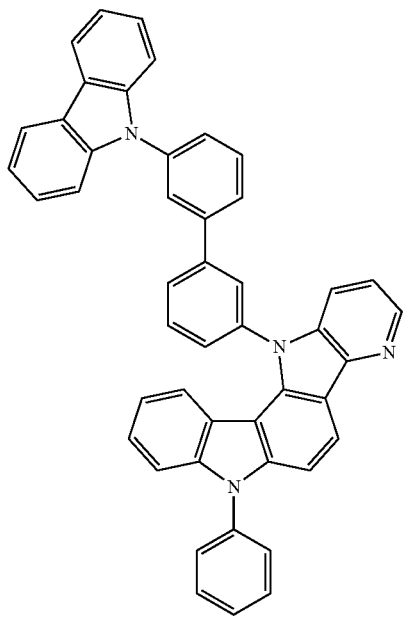
161
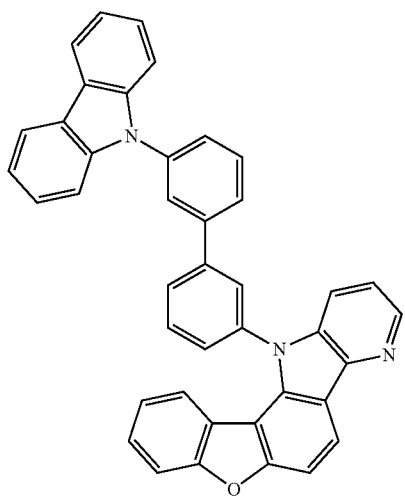
162
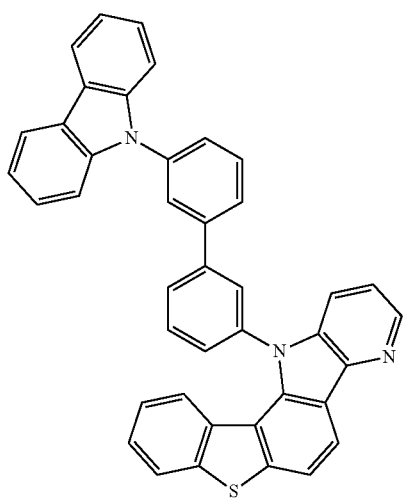
163
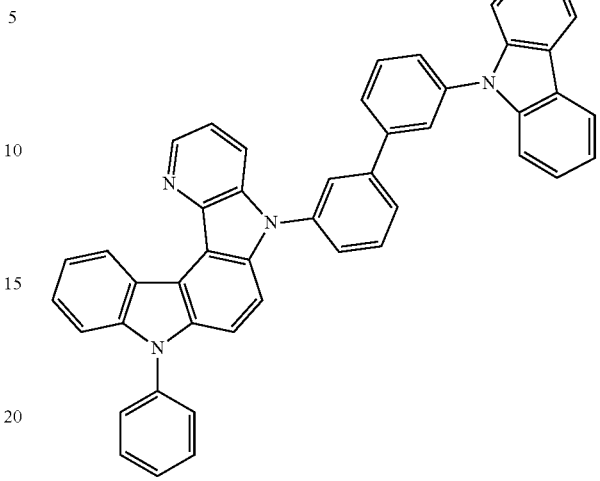
164
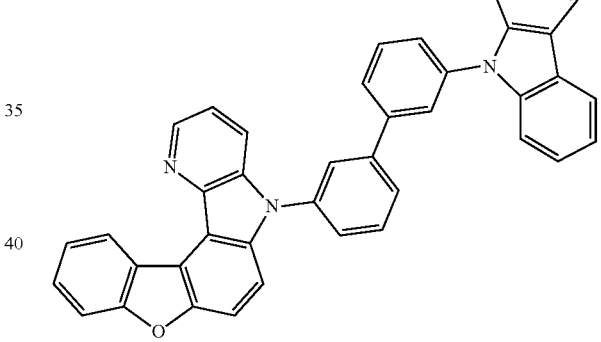
165
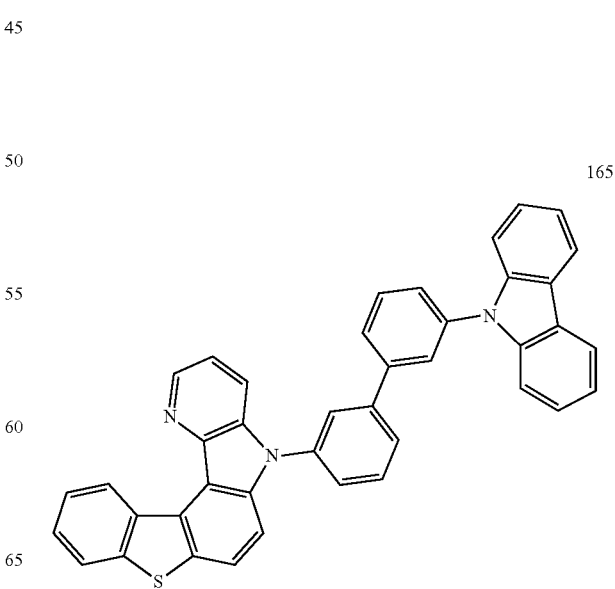

166 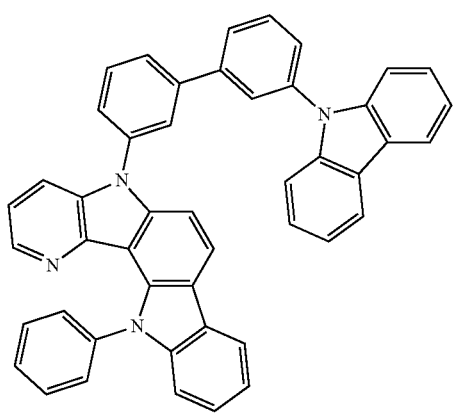
169 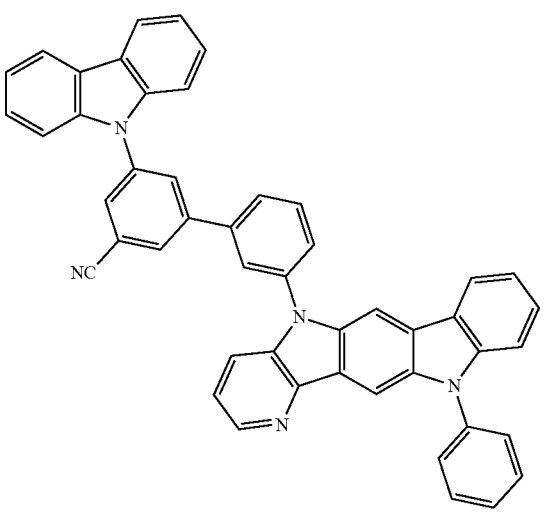
167 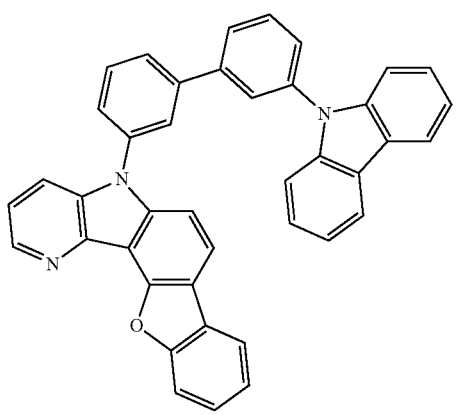
170 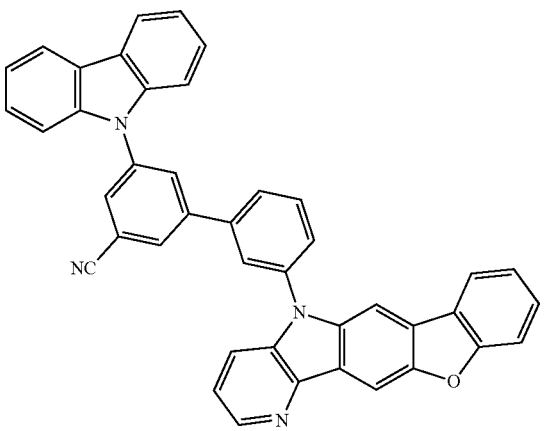
168 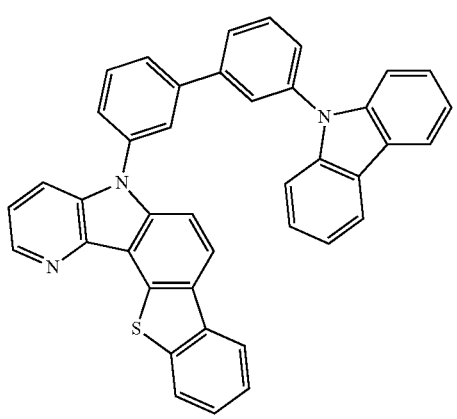
171 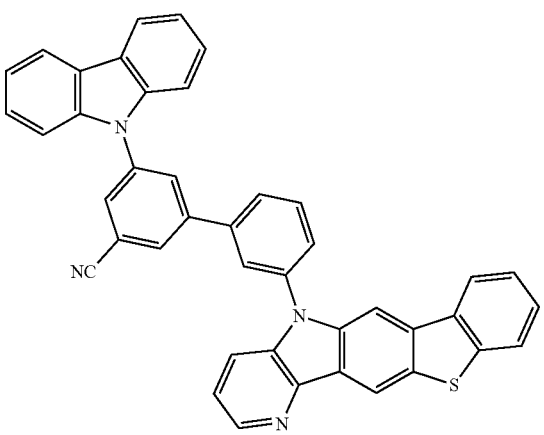

75
-continued
172
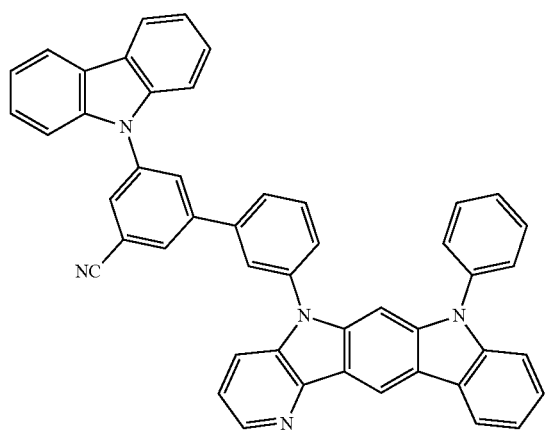
173
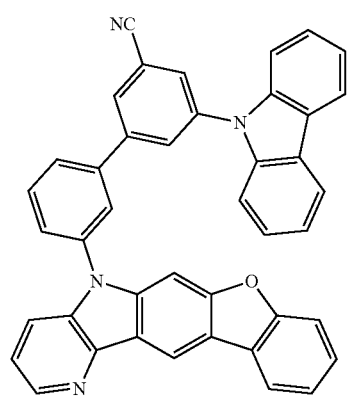
174
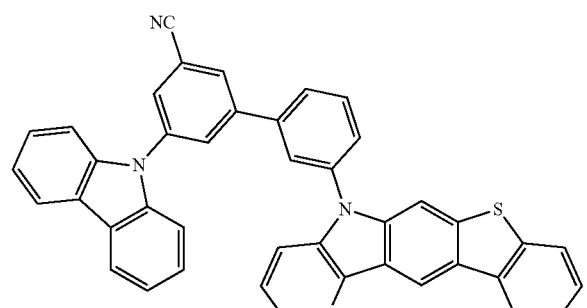
175
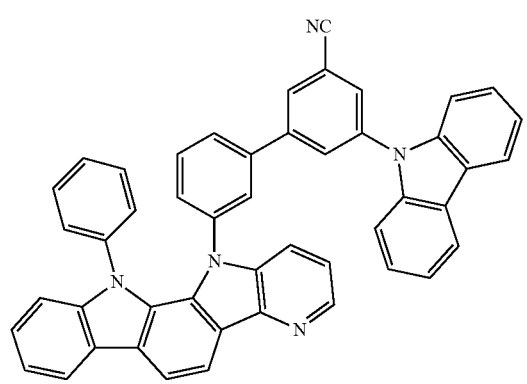
76
-continued
176
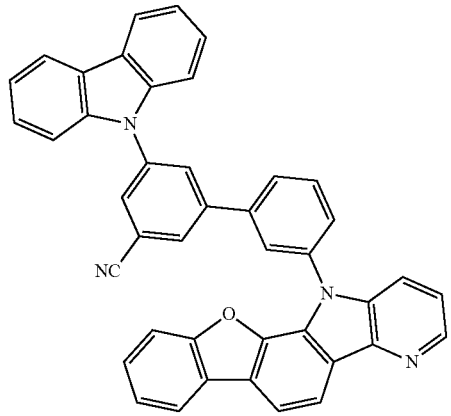
177
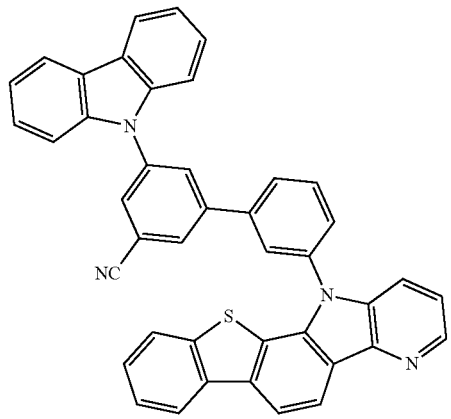
178
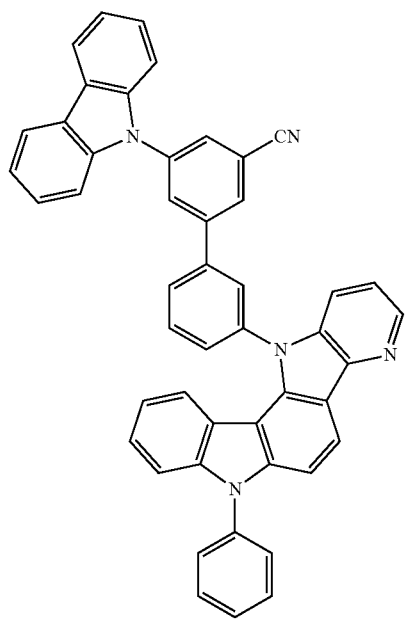

179
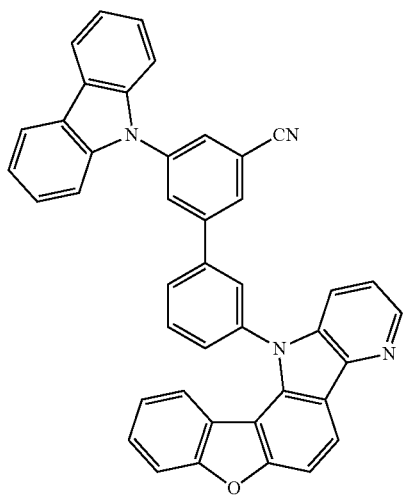
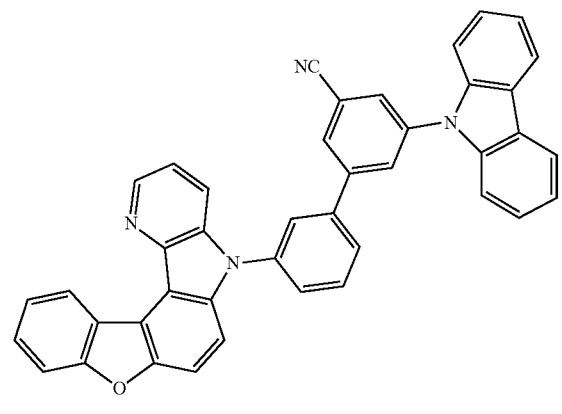
182
180
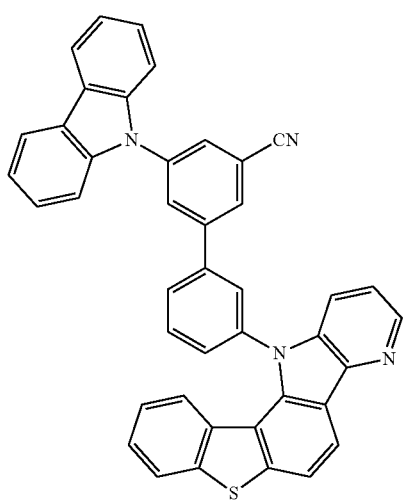
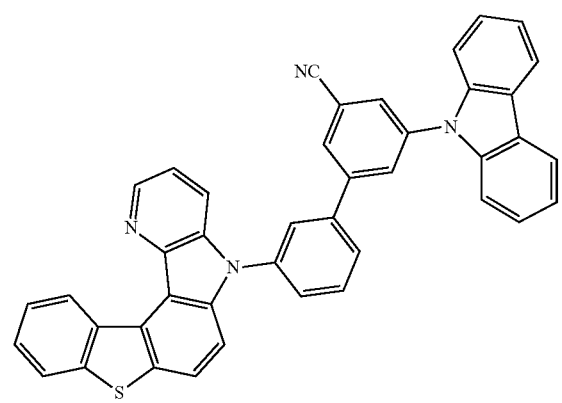
183
181
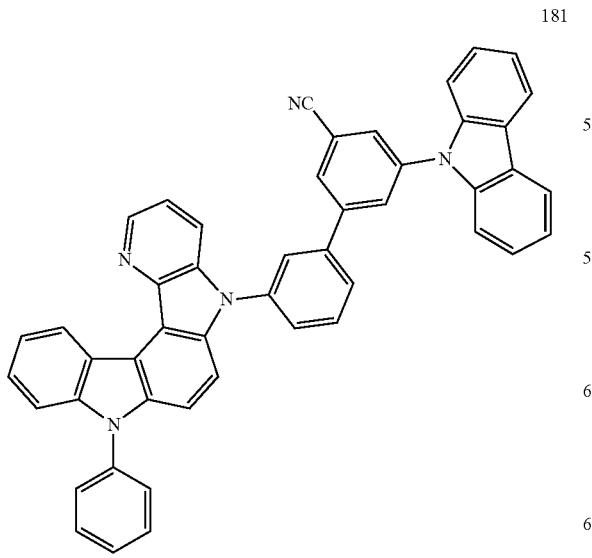
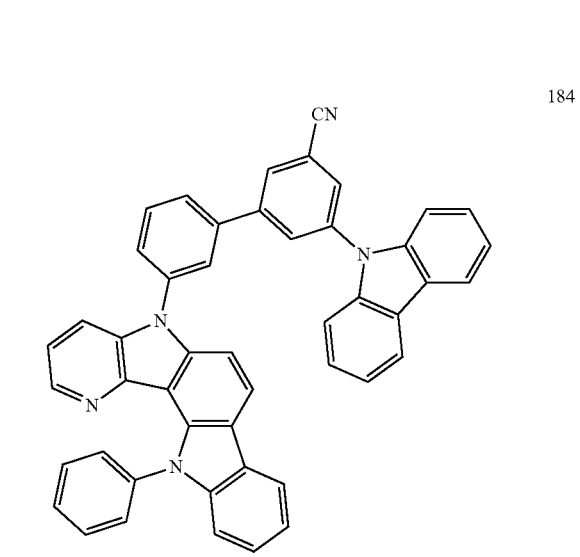
184

185
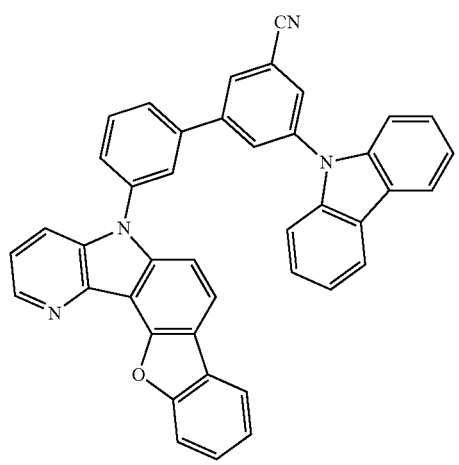
186
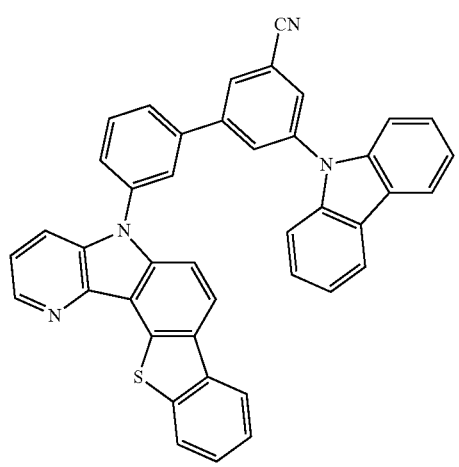
187
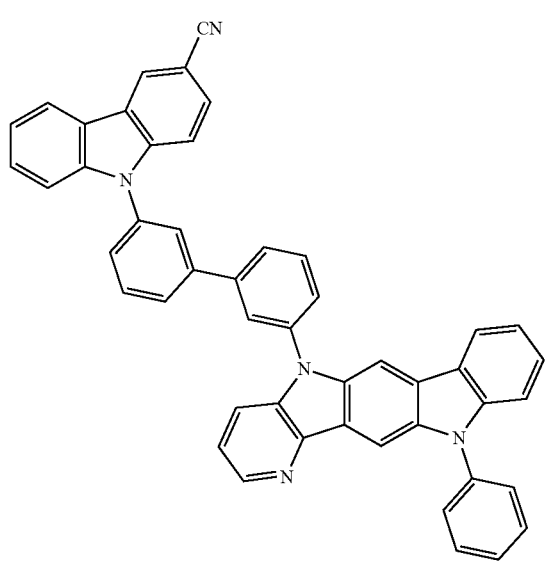
188
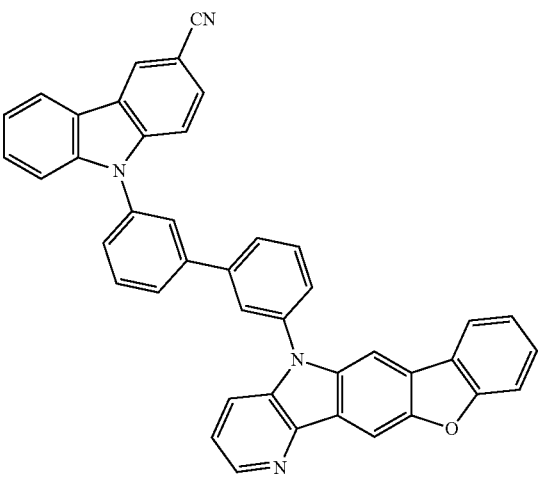
189
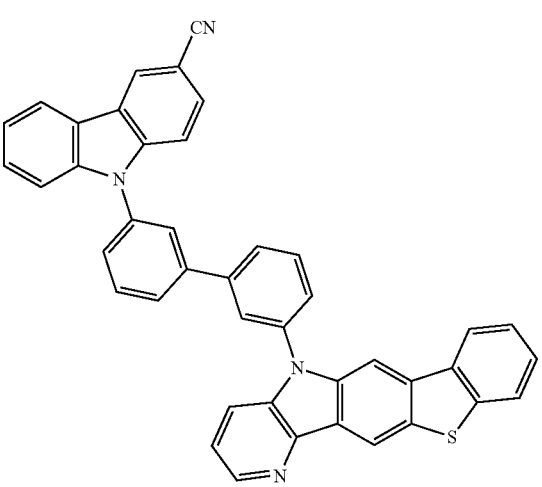
190
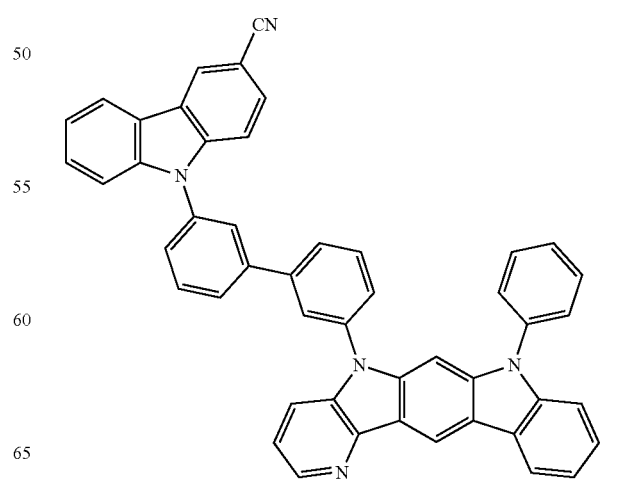

81
-continued
191
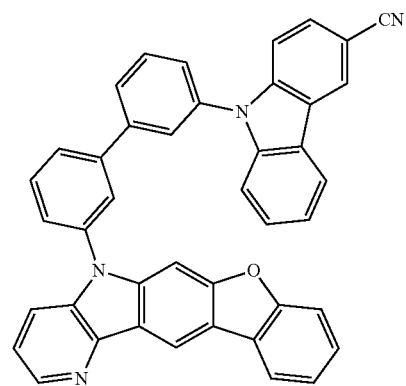
192
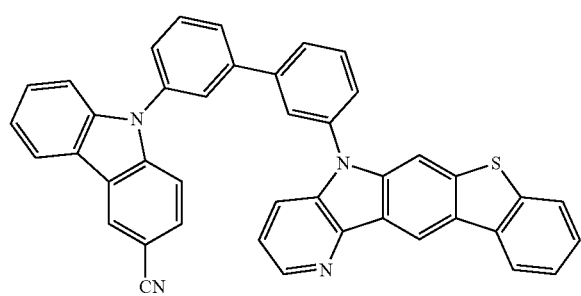
193
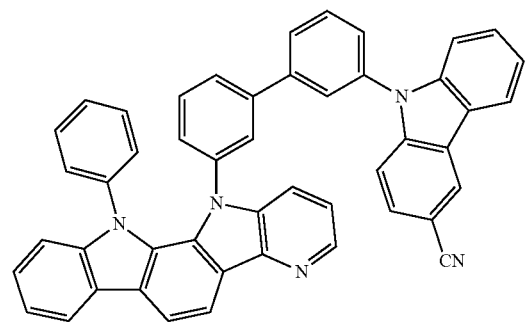
194
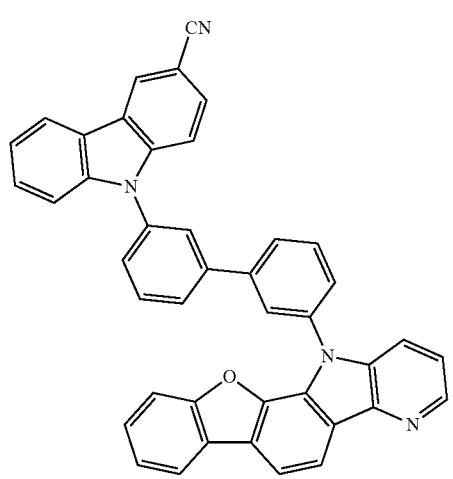
82
-continued
195
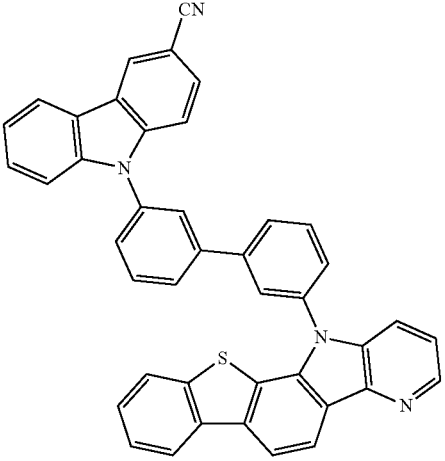
196
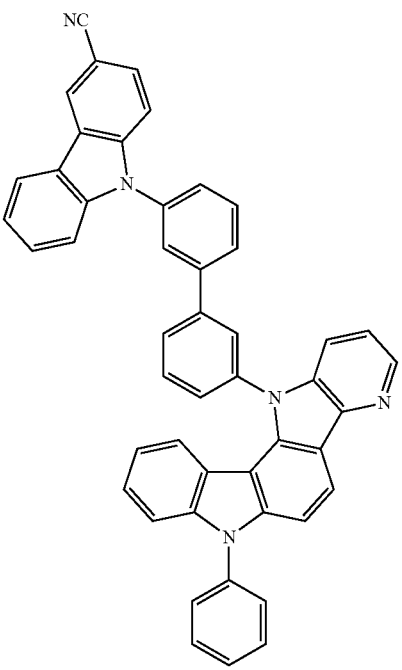
197
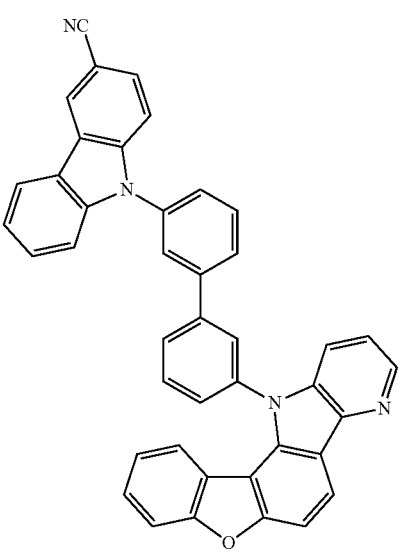

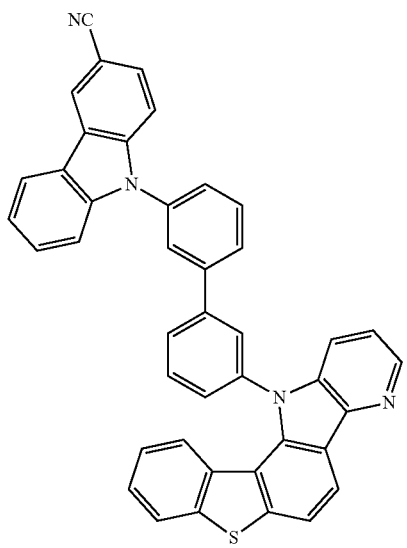
198
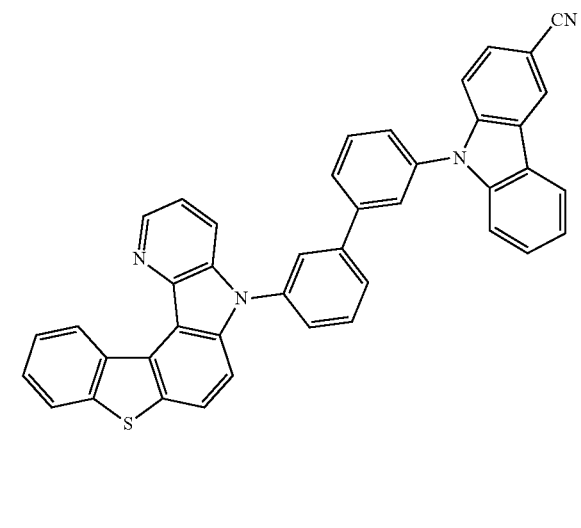
201
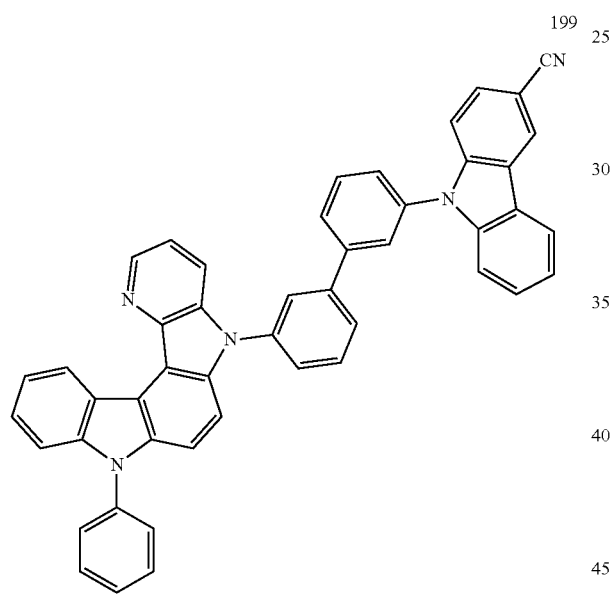
199
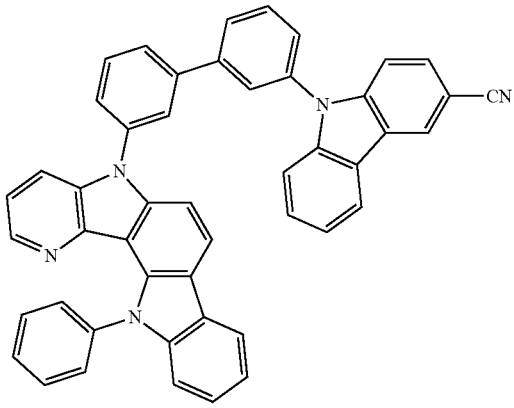
202
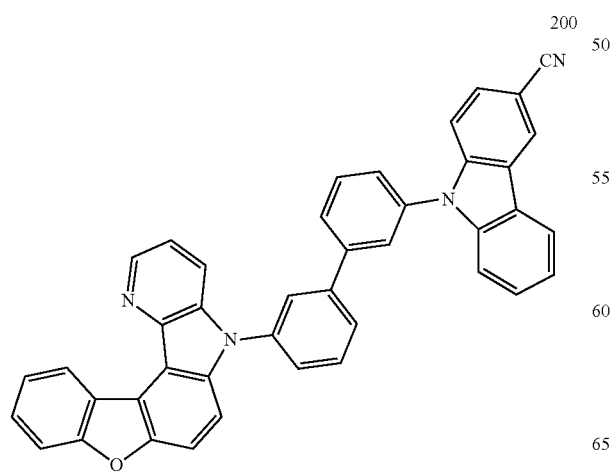
200
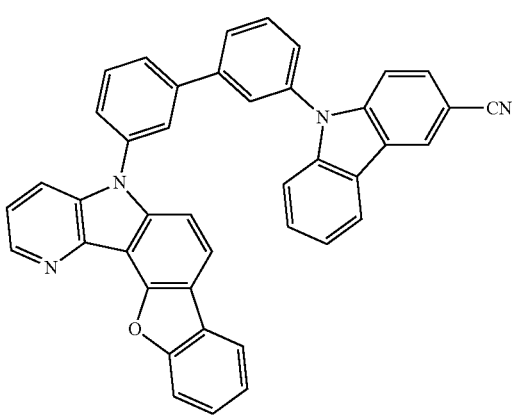
203

204
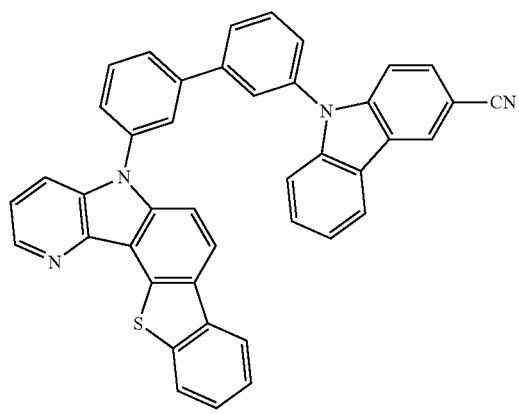
205
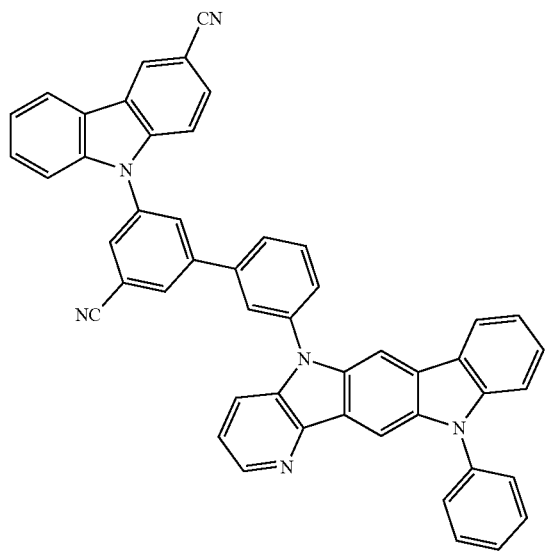
206
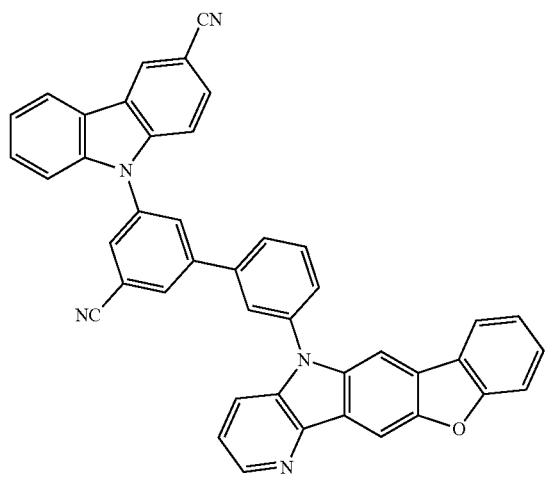
207
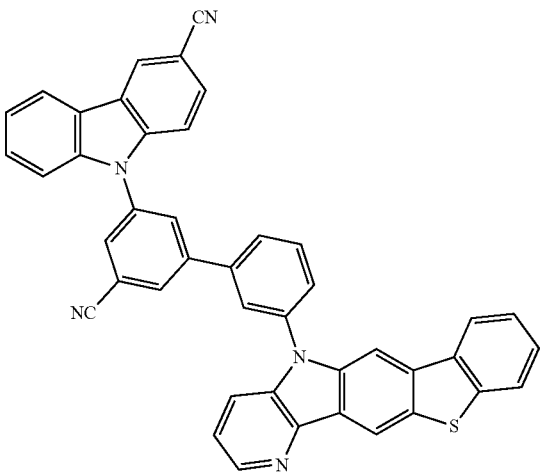
208
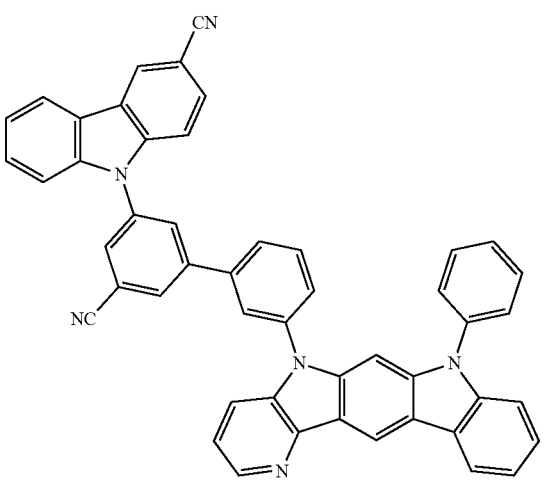
209
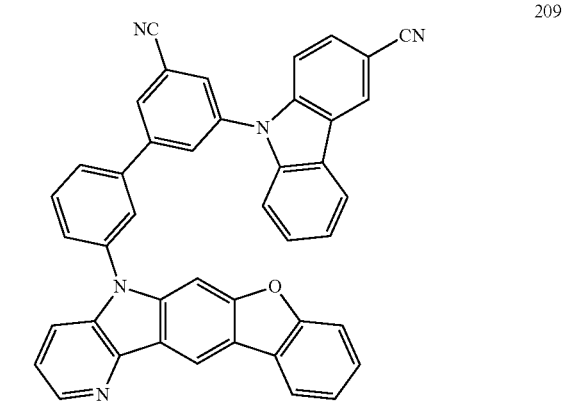

87
-continued
210
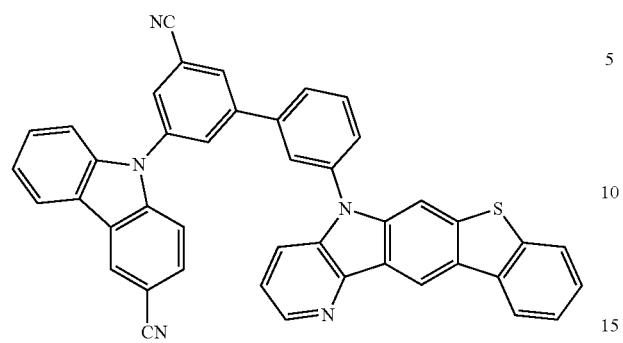
211
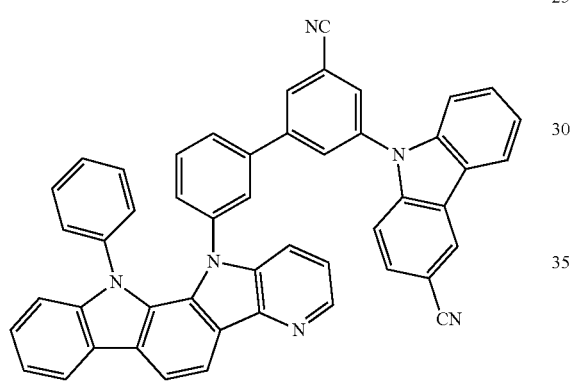
212
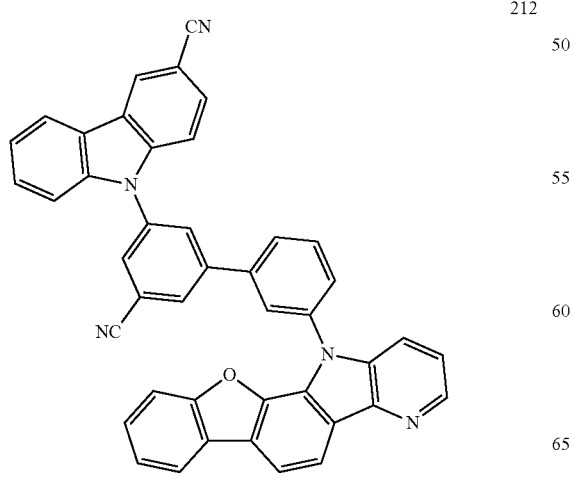
88
-continued
213
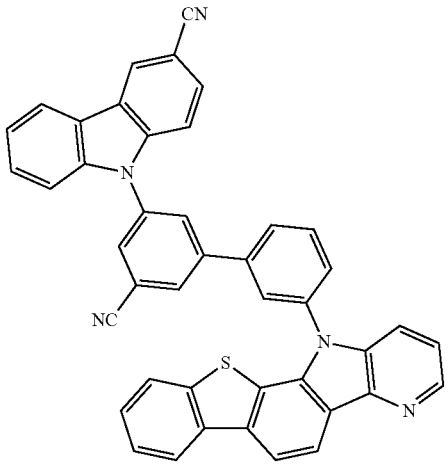
214
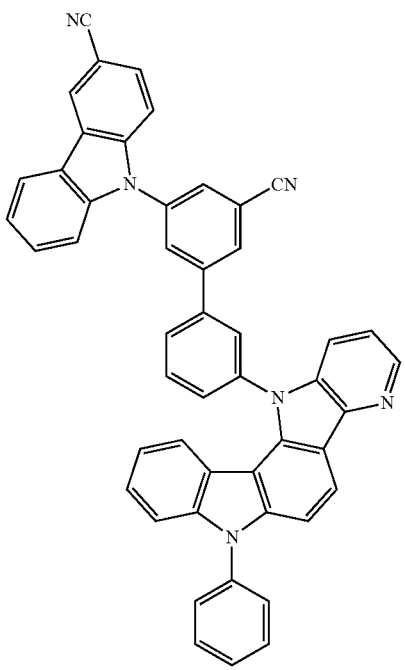
215
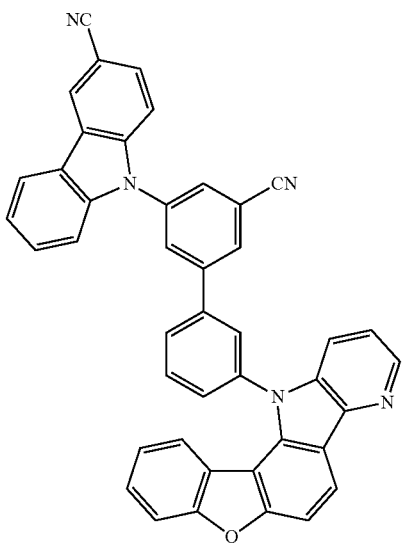

216
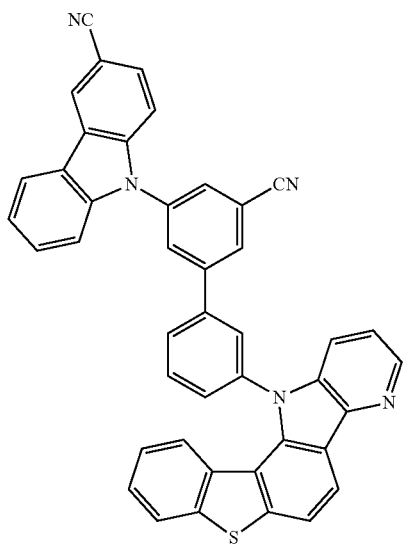
217
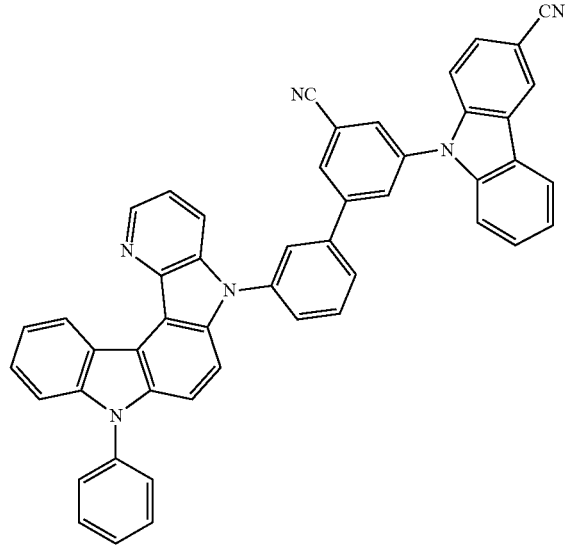
218
219
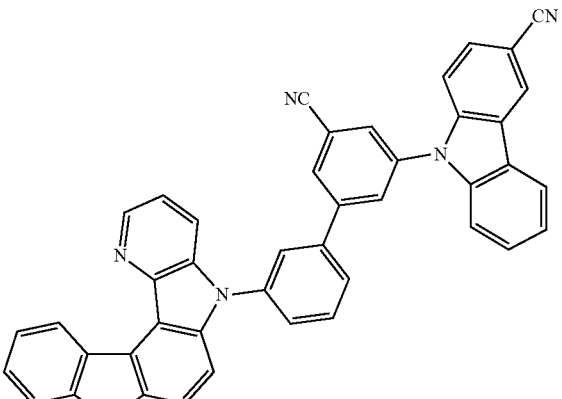
220
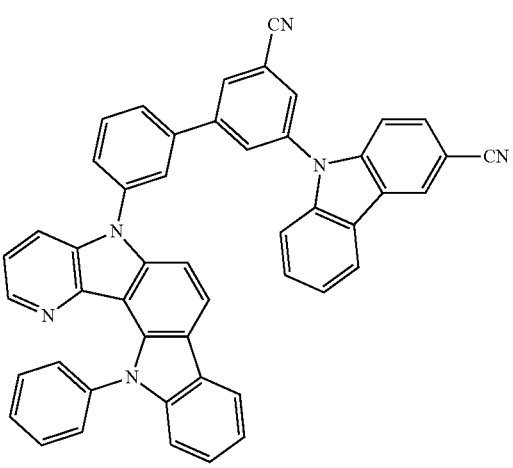
221
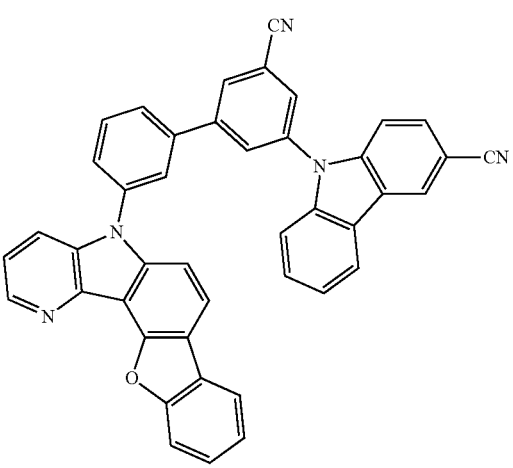

-continued

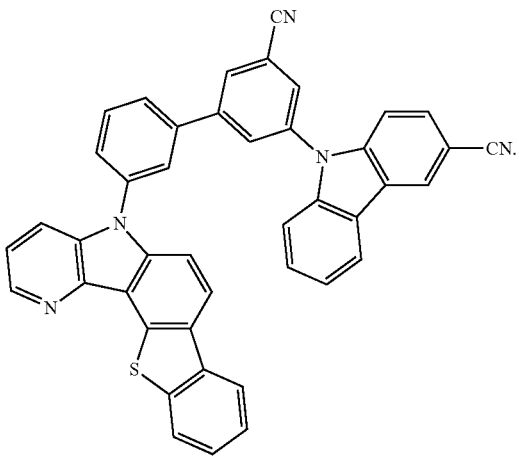

222

In addition, in Formula 1, as Ar₁ may be a group represented by Formula 2, and Ar₂ may be a group represented by Formula 3, the condensed cyclic compound represented by Formula 1 may have excellent thermal stability. Further, in Ar₂ represented by Formula 2, due to the molecular characteristics of at least one selected from $Z_1$ to $Z_3$ being N, the condensed cyclic compound represented by Formula 1 may have excellent thermal stability. Thus, when the condensed cyclic compound represented by Formula 1 is used in an organic light-emitting device, the condensed cyclic compound may have a high charge mobility. Accordingly, an electronic device, e.g., an organic light-emitting device, including the condensed cyclic compound represented by Formula 1 may have long lifespan and high efficiency.

Further, $L_1$ and $L_2$ in Formula 1 may be selected from a group represented by Formula 4 and a group represented by Formula 5. Accordingly, steric hindrance may be induced in the condensed cyclic compound represented by Formula 1, and thus, the condensed cyclic compound may have a high triplet energy and excellent charge transport characteristics. Accordingly, an electronic device, e.g., an organic light-emitting device, including the condensed cyclic compound represented by Formula 1 may have high efficiency and high luminance.

Furthermore, as the condensed cyclic compound represented by Formula 1 has a high $T_g$ value, an organic light-emitting device including the condensed cyclic compound represented by Formula 1 may have improved thermal stability.

The highest occupied molecular orbital (HOMO) energy level, the lowest unoccupied molecular orbital (LUMO) energy level, $T_1$ energy level, and $S_1$ energy level of some of the condensed cyclic compounds represented by Formula 1 were evaluated by using Gaussian 09 that performs molecular structure optimizations according to density functional theory (DFT) at a degree of B3LYP. The results thereof are shown in Table 1.

TABLE 1

|  | HOMO (electron volts, eV) | LUMO (eV) | $T_1$ (eV) | $S_1$ (eV) | $\Delta E_{ST}$ |
|---|---|---|---|---|---|
| Comparative Compound A | −5.719 | −1.956 | 3.021 | 3.109 | 0.088 |

TABLE 1-continued

|  | HOMO (electron volts, eV) | LUMO (eV) | $T_1$ (eV) | $S_1$ (eV) | $\Delta E_{ST}$ |
|---|---|---|---|---|---|
| Comparative Compound B | −5.635 | −2.058 | 3.026 | 3.144 | 0.118 |
| Comparative Compound C | −5.555 | −1.815 | 3.008 | 3.246 | 0.238 |
| Compound 1 | −5.938 | −1.992 | 3.056 | 3.483 | 0.427 |

Referring to Table 1, it was confirmed that Compound 1 has excellent electrical characteristics, e.g., a high $T_1$ energy level.

A method of synthesizing the condensed cyclic compound represented by Formula 1 may be understood by one of ordinary skill in the art by referring to Synthesis Examples described below.

An organic light-emitting device may include:
a first electrode;
a second electrode; and
an organic layer disposed between the first electrode and the second electrode, wherein the organic layer includes an emission layer and at least one condensed cyclic compound represented by Formula 1.

The condensed cyclic compound represented by Formula 1 may be used in an organic layer of the light-emitting device. For example, the condensed cyclic compound represented by Formula 1 may act as a host in an emission layer in the organic layer, but embodiments are not limited thereto.

As the organic light-emitting device includes an organic layer including the condensed cyclic compound represented by Formula 1, the organic light-emitting device may have a low driving voltage, high efficiency, high luminance, and long lifespan.

Therefore, the condensed cyclic compound represented by Formula 1 may be suitable for use in an organic layer of an organic light-emitting device, e.g., a hole transport layer material or an electron blocking layer in the organic layer and/or a host in an emission layer. Thus, according to another aspect of the present description, an organic light-emitting device may include a first electrode; a second electrode; and an organic layer disposed between the first electrode and the second electrode, wherein the organic layer includes an emission layer and at least one condensed cyclic compound represented by Formula 1.

As the organic light-emitting device has an organic layer including the condensed cyclic compound represented by Formula 1, the organic light-emitting device may have a low driving voltage, high efficiency, high luminance, high quantum efficiency, and long lifespan.

In some embodiments, the condensed cyclic compound represented by Formula 1 may be included in the emission layer.

In some embodiments, the condensed cyclic compound represented by Formula 1 may be included in the emission layer, and the condensed cyclic compound may be a delayed fluorescent material.

In an embodiment, the emission layer may include a host and a dopant (where a content of the host may be greater than that of the dopant), and the host may include the condensed cyclic compound represented by Formula 1. The condensed cyclic compound acting as a host may deliver energy to a dopant according to the delayed fluorescence mechanism. The dopant may include at least one selected from a fluorescent dopant and a phosphorescent dopant. The dopant may be any suitable dopant known in the art. The host may further include any suitable host known in the art.

In one or more embodiments, the emission layer may include a host and a dopant (where a content of the host may be greater than that of the dopant), and the dopant may include the condensed cyclic compound represented by Formula 1. The condensed cyclic compound acting as a dopant may emit to delayed fluorescence according to the delayed fluorescence mechanism. The host may be any suitable dopant known in the art.

The emission layer may emit red light, green light, or blue light.

In an embodiment, the emission layer may be a blue emission layer including a phosphorescent dopant, but embodiments are not limited thereto.

In some embodiments, the condensed cyclic compound represented by Formula 1 may be included in a hole transport region.

In some embodiments, a hole transport region of the organic light-emitting device may include at least one selected from a hole transport layer and an electron blocking layer, wherein at least one selected from the hole transport layer and the electron blocking layer may include the condensed cyclic compound represented by Formula 1.

In an embodiment, a hole transport region of the organic light-emitting device may include a hole transport layer, wherein the hole transport layer may include the condensed cyclic compound represented by Formula 1.

In an embodiment, a hole transport region of the organic light-emitting device may include an electron blocking layer, wherein the electron blocking layer may include the condensed cyclic compound represented by Formula 1. The electron blocking layer may be in a direct contact with the emission layer.

In some embodiments, the condensed cyclic compound represented by Formula 1 may be included in an electron transport region.

In an embodiment, an electron transport region of the organic light-emitting device may include an electron transport layer, wherein the electron transport layer may include the condensed cyclic compound represented by Formula 1.

In an embodiment, an electron transport region of the organic light-emitting device may include a hole blocking layer, wherein the hole blocking layer may include the condensed cyclic compound represented by Formula 1. The hole blocking layer may be in a direct contact with the emission layer.

In an embodiment, the emission layer may include the condensed cyclic compound. Here, a ratio of fluorescent emission components may be about 90% or greater, for example, 95% or greater (or for example, 98% or greater) of the whole emission components emitted from the emission layer. In addition, the emission layer may include the condensed cyclic compound represented by Formula 1, and may not include a phosphorescence-emitting compound (e.g., an organometallic compound including a heavy metal). Therefore, the emission layer may be clearly different from a phosphorescent emission layer, in which a ratio of phosphorescent emission components may be, for example, about 80% or greater of the whole emission components, by including a phosphorescent dopant.

In some embodiments, in which the condensed cyclic compound included in the emission layer is used as a fluorescent emitter, a ratio of emission components emitted from the condensed cyclic compound may be about 80% or greater, for example, 90% or greater of the whole emission components emitted from the emission layer. In some embodiments, a ratio of emission components emitted from the condensed cyclic compound may be 95% or greater of the whole emission components emitted from the emission layer. Here, the emission components of the condensed cyclic compound may be a total of prompt emission components of the condensed cyclic compound and delayed fluorescence components by reverse intersystem crossing of the condensed cyclic compound.

In some embodiments, the emission layer may include the condensed cyclic compound only; or the emission layer may further include a host (where the host may not be identical to the condensed cyclic compound).

When the emission layer further includes a host, in addition to the condensed cyclic compound, a content of the condensed cyclic compound may be 50 parts by weight or less, for example, 30 parts by weight or less, based on 100 parts by weight of the emission layer, and a content of the host may be 50 parts by weight or greater, for example, 70 parts by weight or greater, based on 100 parts by weight of the emission layer, but embodiments are not limited thereto.

In addition, in some embodiments, in which the condensed cyclic compound included in the emission layer is used as a fluorescent host, the emission layer may include a host and a fluorescent dopant, and the host may include the condensed cyclic compound, a ratio of emission components of the fluorescent dopant may be 80% or greater, for example, 90% or greater (or for example, 95% or greater), based on the whole emission components emitted from the emission layer.

Here, a content of the dopant may be 50 parts by weight or less, for example, 30 parts by weight or less, based on 100 parts by weight of the emission layer, and a content of the host may be 50 parts by weight or greater, for example, 70 parts by weight or greater, based on 100 parts by weight of the emission layer, but embodiments are not limited thereto.

When the condensed cyclic compound included in the emission layer is used as a fluorescent host, the fluorescent host may include the condensed cyclic compound only or include another host known in the art.

The term "organic layer" as used herein refers to a single and/or a plurality of layers between the first electrode and the second electrode in an organic light-emitting device. The "organic layer" may include not only organic compounds but also organometallic complexes including metals.

FIG. 1 illustrates a schematic cross-sectional view of an organic light-emitting device 10 according to an embodiment. Hereinafter, a structure of an organic light-emitting device according to one or more embodiments and a method of manufacturing the organic light-emitting device will be described with reference to FIG. 1. The organic light-emitting device 10 may include a first electrode 11, an organic layer 15, and a second electrode 19, which may be sequentially layered in this stated order.

A substrate may be additionally disposed under the first electrode 11 or on the second electrode 19. The substrate may be a conventional substrate used in organic light-emitting devices, e.g., a glass substrate or a transparent plastic substrate, each having excellent mechanical strength, thermal stability, transparency, surface smoothness, ease of handling, and water repellency.

The first electrode 11 may be formed by vacuum-depositing or sputtering, onto the substrate, a material for forming the first electrode 11. The first electrode 11 may be an anode. The material for forming the first electrode 11 may be selected from materials with a high work function for easy hole injection. The first electrode 11 may be a reflective electrode, a semi-transmissive electrode, or a transmissive electrode. The material for forming the first electrode 11 may be selected from indium tin oxide (ITO), indium zinc oxide (IZO), tin oxide (SnO$_2$), and zinc oxide (ZnO). In some embodiments, the material for forming the first electrode 11 may be a metal, such as magnesium (Mg), aluminum (Al), aluminum-lithium (Al—Li), calcium (Ca), magnesium-indium (Mg—In), or magnesium-silver (Mg—Ag).

The first electrode 11 may have a single-layered structure or a multi-layered structure including a plurality of layers. In some embodiments, the first electrode 11 may have a triple-layered structure of ITO/Ag/ITO, but embodiments are not limited thereto.

The organic layer 15 may be on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, a hole transport layer, an electron blocking layer, and a buffer layer.

The hole transport region may include a hole injection layer only or a hole transport layer only. In some embodiments, the hole transport region may include a hole injection layer and a hole transport layer which are sequentially stacked on the first electrode 11. In some embodiments, the hole transport region may include a hole injection layer, a hole transport layer, and an electron blocking layer, which are sequentially stacked on the first electrode 11.

When the hole transport region includes a hole injection layer, the hole injection layer may be formed on the first electrode 11 by using one or more suitable methods, such as vacuum deposition, spin coating, casting, and Langmuir-Blodgett (LB) deposition.

When a hole injection layer is formed by vacuum-deposition, for example, the vacuum deposition may be performed at a temperature in a range of about 100° C. to about 500° C., at a vacuum degree in a range of about $10^{-8}$ torr to about $10^{-3}$ torr, and at a rate in a range of about 0.01 Angstroms per second (Å/sec) to about 100 Å/sec, though the conditions may vary depending on a compound used as a hole injection material and a structure and thermal properties of a desired hole injection layer, but embodiments are not limited thereto.

When a hole injection layer is formed by spin coating, the spin coating may be performed at a rate in a range of about 2,000 revolutions per minute (rpm) to about 5,000 rpm and at a temperature in a range of about 80° C. to 200° C. to facilitate removal of a solvent after the spin coating, though the conditions may vary depending on a compound used as a hole injection material and a structure and thermal properties of a desired hole injection layer, but embodiments are not limited thereto.

The conditions for forming a hole transport layer and an electron blocking layer may be inferred from the conditions for forming the hole injection layer.

The hole transport region may include at least one selected from m-MTDATA, TDATA, 2-TNATA, NPB, 8-NPB, TPD, spiro-TPD, spiro-NPB, methylated-NPB, TAPC, HMTPD, 4,4',4"-tris(N-carbazolyl)triphenylamine (TCTA), polyaniline/dodecylbenzene sulfonic acid (PANI/DBSA), poly(3,4-ethylenedioxythiophene)/poly(4-styrene sulfonate) (PEDOT/PSS), polyaniline/camphor sulfonic acid (PANI/CSA), (polyaniline)/poly(4-styrene sulfonate) (PANI/PSS), a compound represented by Formula 201, and a compound represented by Formula 202:

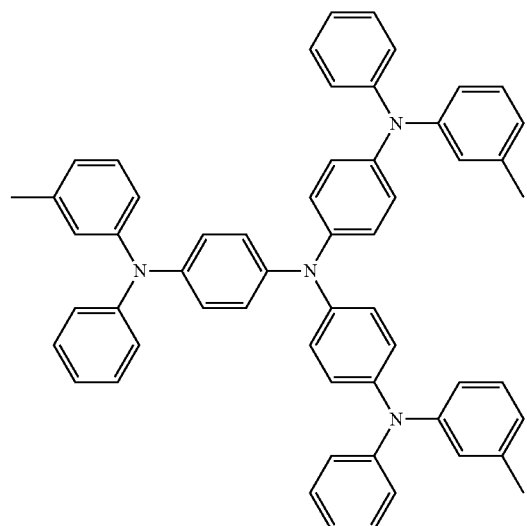

m-MTDATA

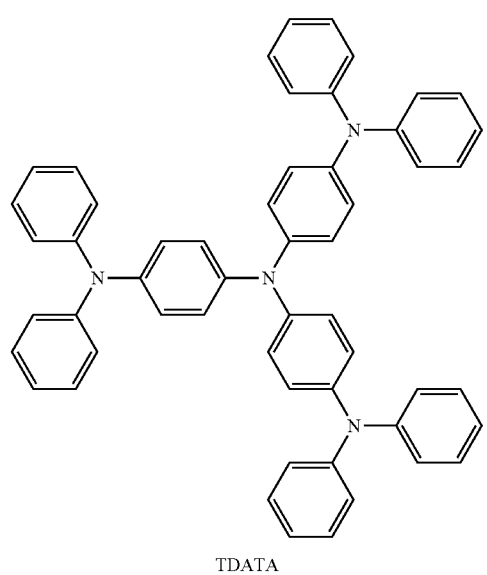

TDATA

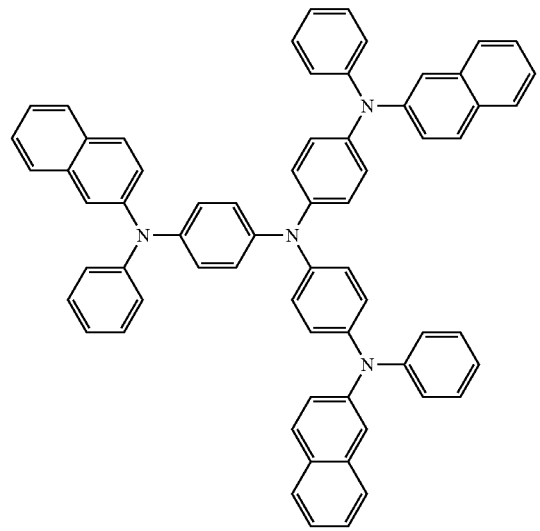

2-TNATA

-continued

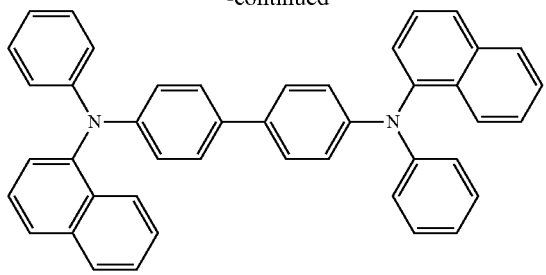

NPB

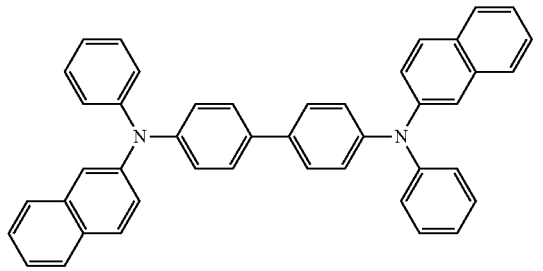

β-NPB

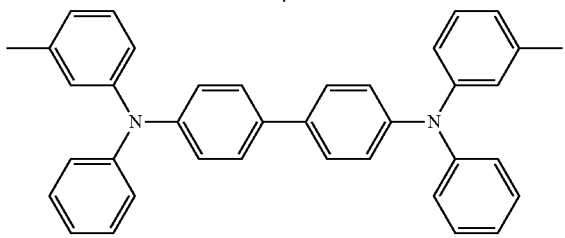

TPD

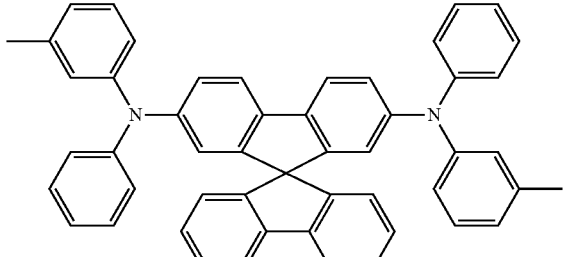

Spiro-TPD

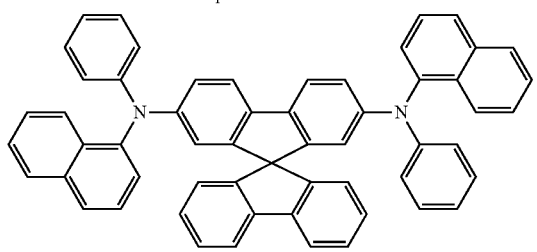

Spiro-NPB

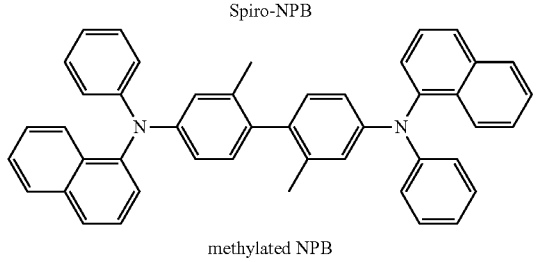

methylated NPB

-continued

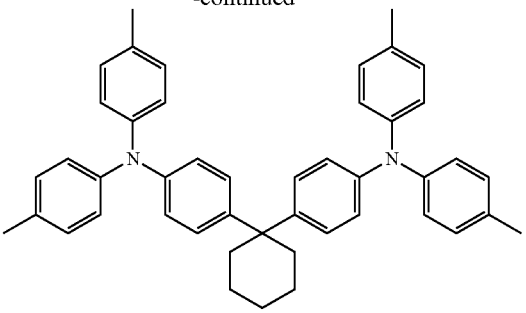

TAPC

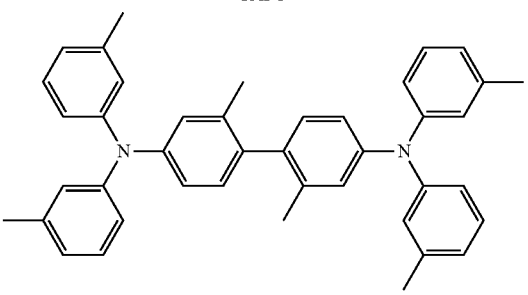

HMTPD

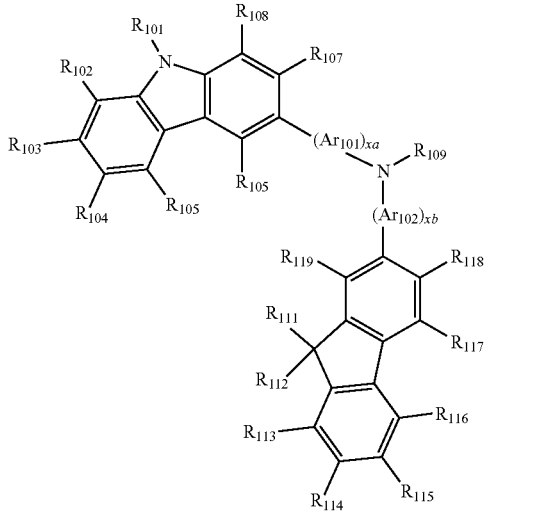

Formula 201

Formula 202

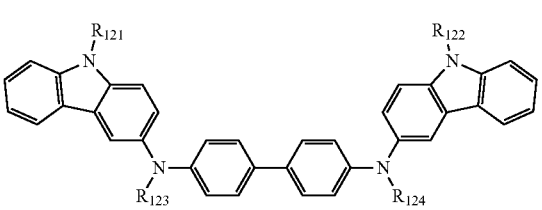

wherein, in Formula 201, $Ar_{101}$ and $Ar_{102}$ may each independently be selected from:

a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In Formula 201, xa and xb may each independently be an integer from 0 to 5. In some embodiments, xa and xb may each independently be an integer from 0, 1, and 2. In some embodiments, xa may be 1, and xb may be 0, but embodiments are not limited thereto.

In Formulae 201 and 202, $R_{101}$ to $R_{108}$, $R_{111}$ to $R_{119}$, and $R_{121}$ to $R_{124}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (e.g., a methyl group, an ethyl group, a propyl group, a butyl group, pentyl group, or a hexyl group), and a $C_1$-$C_{10}$ alkoxy group (e.g., a methoxy group, an ethoxy group, a propoxy group, a butoxy group, or a pentoxy group);

a $C_1$-$C_{10}$ alkyl group and a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but embodiments are not limited thereto.

In Formula 201, $R_{109}$ may be selected from:
a phenyl group, a naphthyl group, an anthracenyl group, and a pyridinyl group; and a phenyl group, a naphthyl group, an anthracenyl group, and a pyridinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

In some embodiments, the compound represented by Formula 201 may be represented by Formula 201A, but embodiments are not limited thereto:

Formula 201A

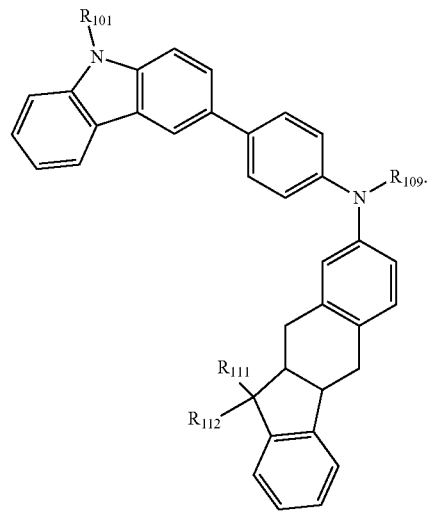

$R_{101}$, $R_{111}$, $R_{112}$, and $R_{109}$ in Formula 201A may respectively be understood by referring to the descriptions for those provided herein.

In some embodiments, the compounds represented by Formulae 201 and 202 may include Compounds HT1 to HT20, but embodiments are not limited thereto:

HT1

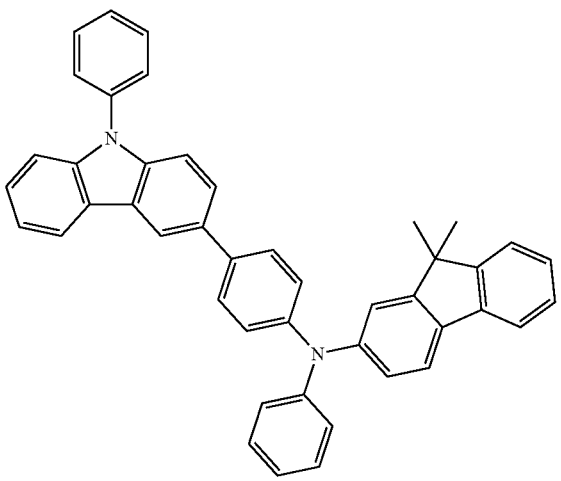

HT2
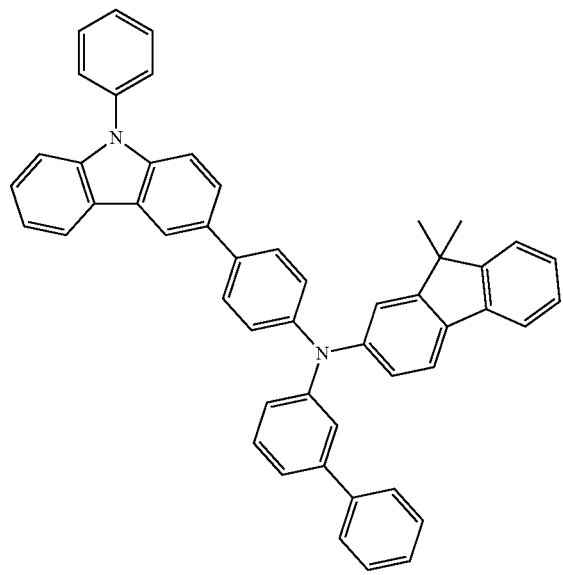
HT3
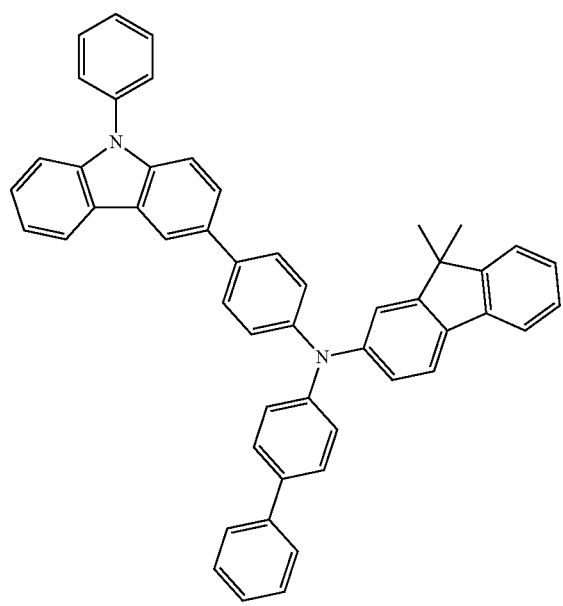
HT4
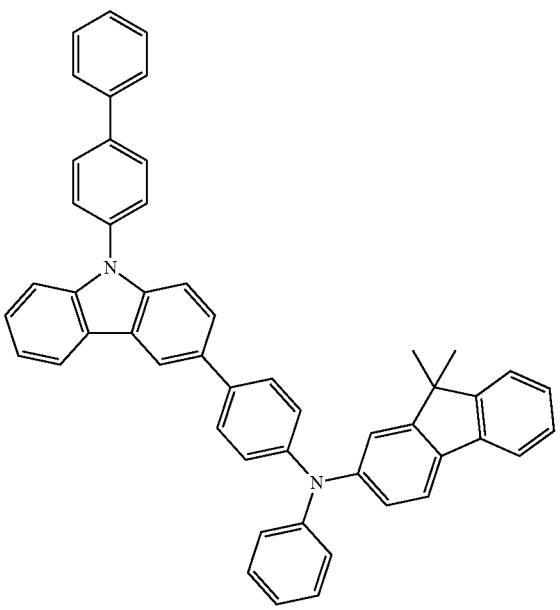
HT5
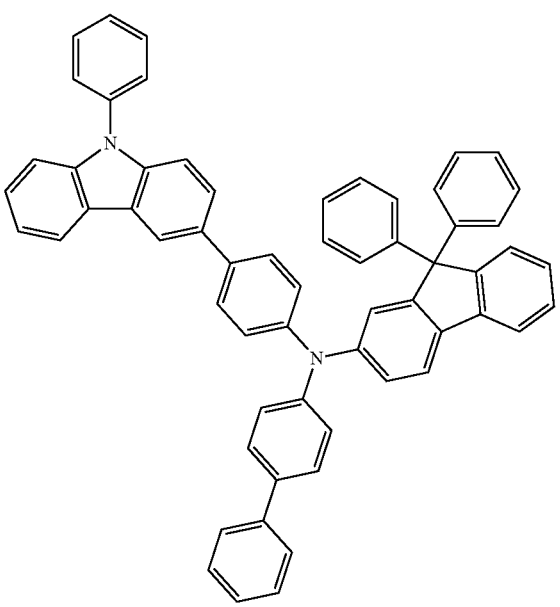

HT6
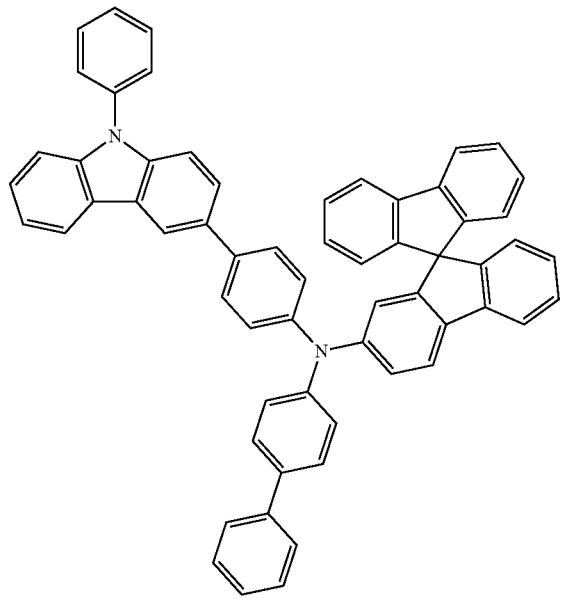
HT8
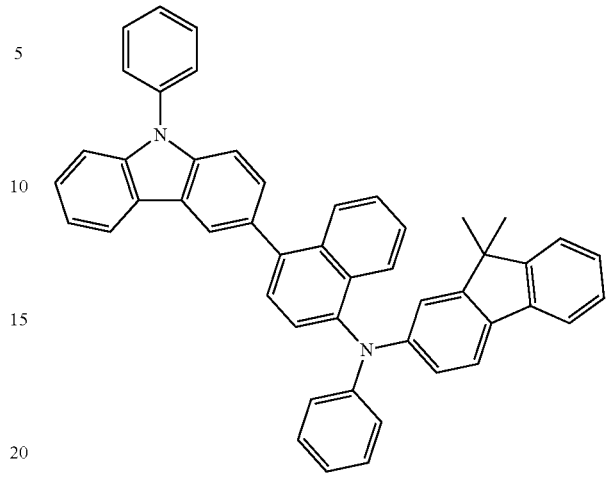
HT9
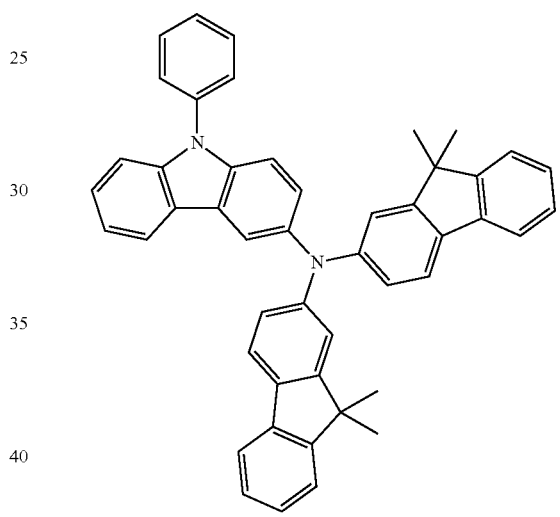
HT7
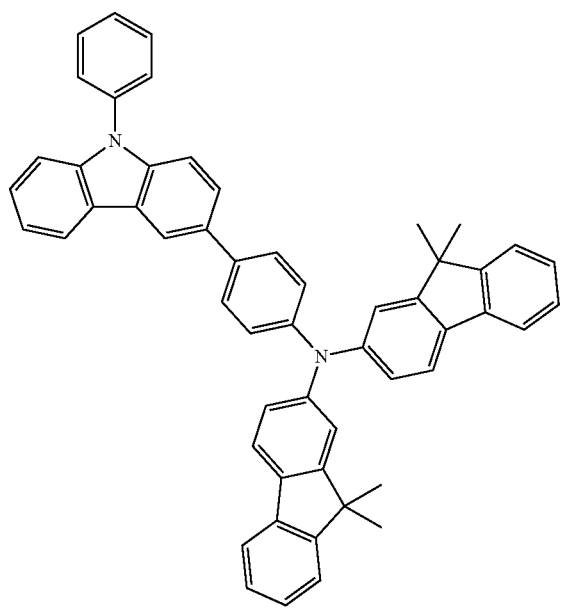
HT10
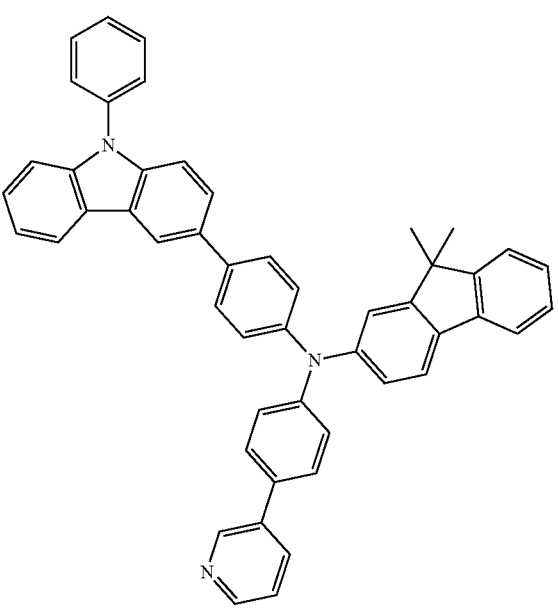

HT11
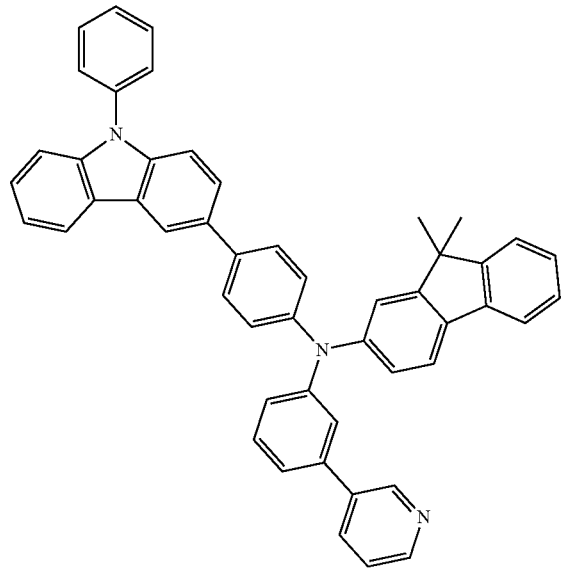
HT14
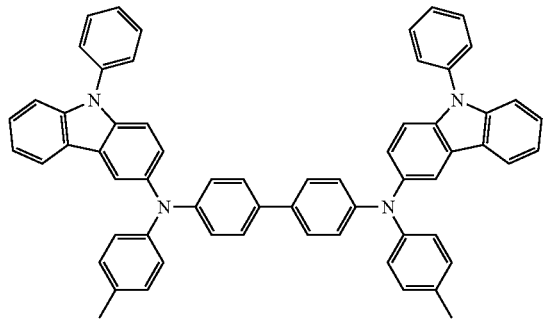
HT15
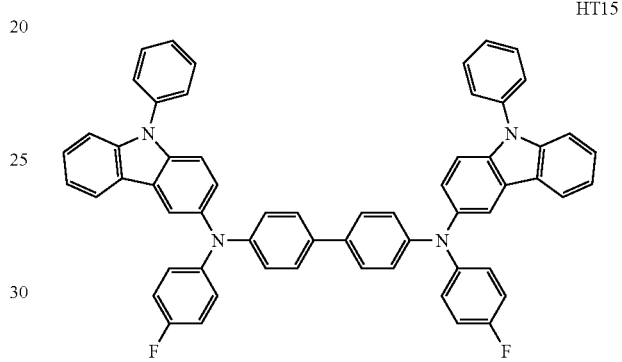
HT12
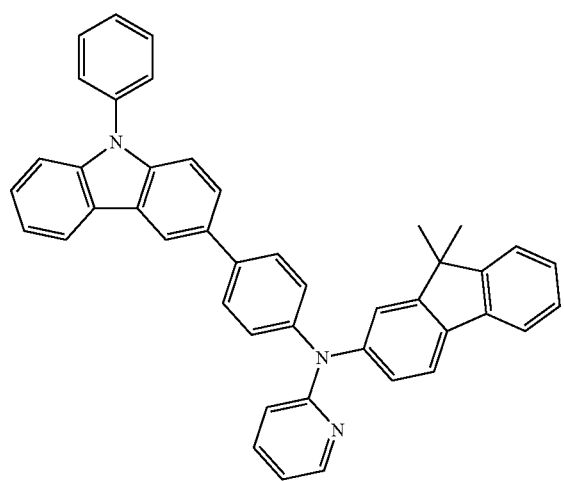
HT16
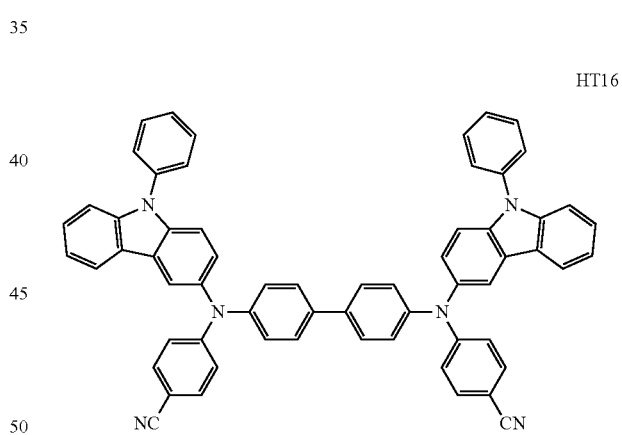
HT13
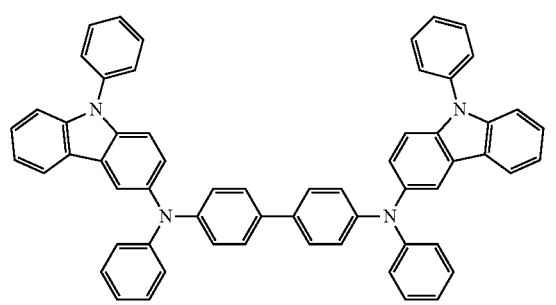
HT17
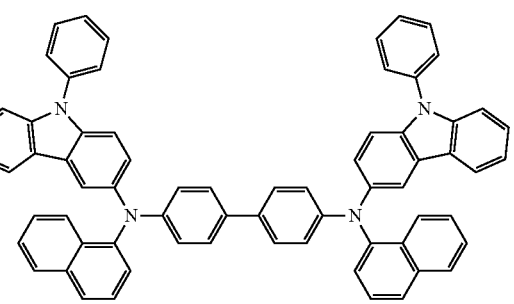

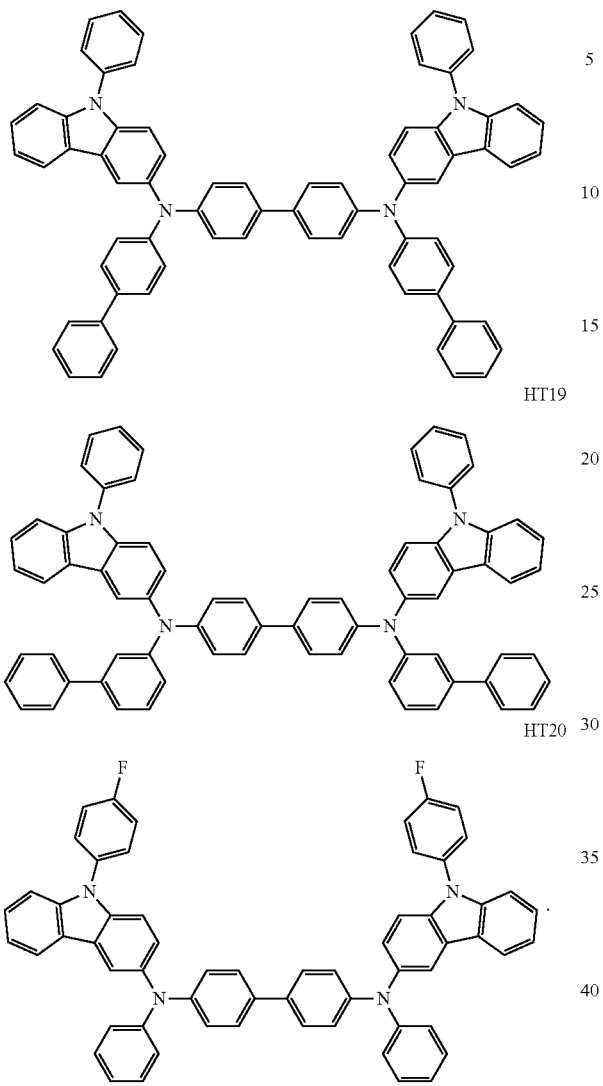

The hole transport layer may include the condensed cyclic compound represented by Formula 1.

The thickness of the hole transport region may be in a range of about 100 Angstroms (Å) to about 10,000 Å, for example, about 100 Å to about 1,000 Å. When the hole transport region includes at least one selected from a hole injection layer and a hole transport layer, the thickness of the hole injection layer may be in a range of about 100 Å to about 10,000 Å, for example, about 100 Å to about 1,000 Å, the thickness of the hole transport layer may be in a range of about 50 Å to about 2,000 Å, for example, about 100 Å to about 1,500 Å. While not wishing to be bound by theory, it is understood that when the thicknesses of the hole transport region, the hole injection layer, and the hole transport layer are within any of these ranges, excellent hole transport characteristics may be obtained without a substantial increase in driving voltage.

The hole transport region may include a charge generating material as well as the aforementioned materials, to improve conductive properties of the hole transport region. The charge generating material may be substantially homogeneously or non-homogeneously dispersed in the hole transport region.

The charge generating material may include, for example, a p-dopant. The p-dopant may include one of a quinone derivative, a metal oxide, and a compound containing a cyano group, but embodiments are not limited thereto. For example, non-limiting examples of the p-dopant include a quinone derivative, such as tetracyanoquinodimethane (TCNQ) or 2,3,5,6-tetrafluoro-tetracyano-1,4-benzoquinonedimethane (F4-TCNQ); a metal oxide, such as a tungsten oxide or a molybdenum oxide; and a compound containing a cyano group, such as Compound HT-D1 or Compound HP-1, but embodiments are not limited thereto:

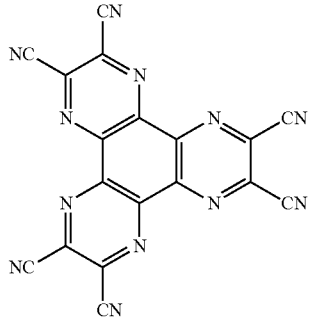

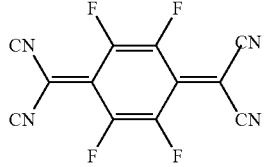

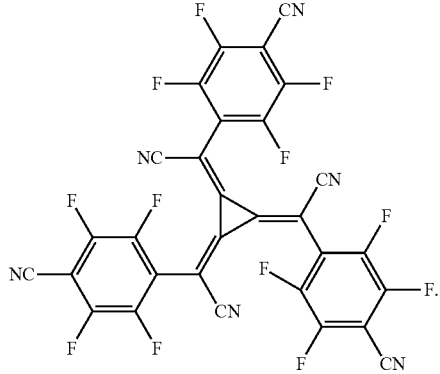

The hole transport region may further include a buffer layer.

The buffer layer may compensate for an optical resonance distance depending on a wavelength of light emitted from the emission layer to improve the efficiency of an organic light-emitting device.

An emission layer may be formed on the hole transport region by using one or more suitable methods, such as vacuum deposition, spin coating, casting, or LB deposition. When the emission layer is formed by vacuum deposition or spin coating, vacuum deposition and coating conditions for forming the emission layer may be generally similar to the those conditions for forming a hole injection layer, though the conditions may vary depending on a compound that is used.

The hole transport region may further include an electron blocking layer. The electron blocking layer may include any suitable known material, e.g., mCP, but embodiments are not limited thereto:

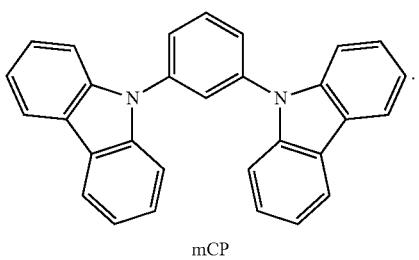 [SMILES: c1cc(-n2c3ccccc3c3ccccc32)cc(-n2c3ccccc3c3ccccc32)c1]

mCP

The hole transport region may include an electron blocking layer, wherein the electron blocking layer may include the condensed cyclic compound represented by Formula 1.

The thickness of the electron blocking layer may be in a range of about 50 Å to about 1,000 Å, and in some embodiments, about 70 Å to about 500 Å. While not wishing to be bound by theory, it is understood that when the thickness of the electron blocking layer is within any of these ranges, excellent electron blocking characteristics may be obtained without a substantial increase in driving voltage.

When the organic light-emitting device 10 is a full-color organic light-emitting device, the emission layer may be patterned into a red emission layer, a green emission layer, and a blue emission layer. In some embodiments, the emission layer may have a structure in which the red emission layer, the green emission layer, and/or the blue emission layer are layered to emit white light. In some embodiments, the structure of the emission layer may vary.

The emission layer may include the condensed cyclic compound represented by Formula 1. In some embodiments, the emission layer may include the condensed cyclic compound represented by Formula 1 only. In some embodiments, the emission layer may include a host and a dopant, and the host may include the condensed cyclic compound represented by Formula 1. In some embodiments, the emission layer may include a host and a dopant, and the dopant may include the condensed cyclic compound represented by Formula 1.

According to an embodiment, the dopant in the emission layer may be a phosphorescent dopant, and the phosphorescent dopant may include an organometallic compound represented by Formula 81:

Formula 81

$$\left[ \begin{array}{c} (R_{81})_{a81} \\ | \\ CY_{81} \\ Y_{81} \\ Y_{82} \\ | \\ Y_{83} \\ CY_{82} \\ Y_{84} \\ | \\ (R_{82})_{a82} \end{array} M-(L_{81})_{n81} \right]_{n82}$$

wherein, in Formula 81,

M may be selected from iridium (Ir), platinum (Pt), osmium (Os), titanium (Ti), zirconium (Zr), hafnium (Hf), europium (Eu), terbium (Tb), thulium (Tm), rhenium (Re), and rhodium (Rh), $Y_{81}$ to $Y_{84}$ may each independently be C or N, $Y_{81}$ and $Y_{82}$ may be bound via a single bond or a double bond, $Y_{83}$ and $Y_{84}$ may be bound via a single bond or a double bond, $CY_{81}$ and $CY_{82}$ may each independently be a benzene group, a naphthalene group, a fluorene group, a spirobifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, or a dibenzothiophene group, wherein $CY_{81}$ may optionally be bound to $CY_{82}$ via an organic linking group, $R_{81}$ and $R_{82}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —$SF_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, and —$B(Q_6)(Q_7)$, a81 and a82 may each independently be an integer from 1 to 5, n81 may be an integer from 0 to 4, n82 may be an integer from 1, 2, and 3, $L_{81}$ may be any suitable monovalent, divalent, or trivalent organic ligand, and $Q_1$ to $Q_7$ may each be understood by referring to the descriptions for $Q_1$ to $Q_3$ of —$Si(Q_1)(Q_2)(Q_3)$ in Formula 1 provided herein.

$R_{81}$ and $R_{82}$ may each be understood by referring to the descriptions for $R_{11}$ provided herein.

The phosphorescent dopant may include at least one selected from Compounds PD1 to PD78 and $FIr_6$, but embodiments are not limited thereto:

PD1

PD2 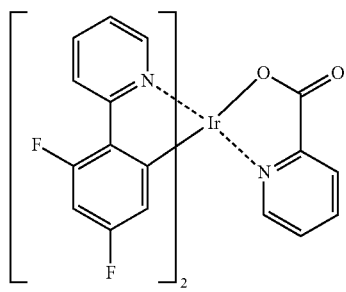
PD7 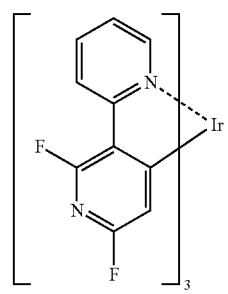
PD3 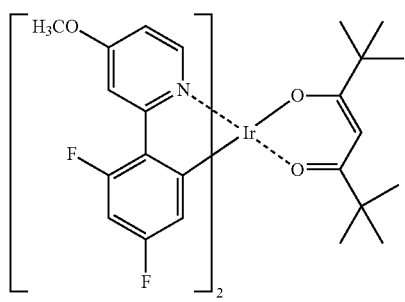
PD8 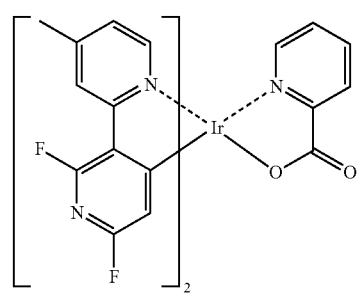
PD4 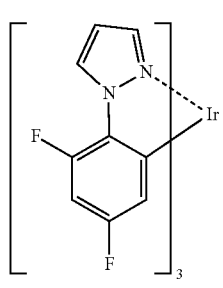
PD9 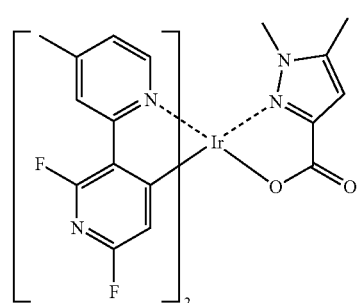
PD5 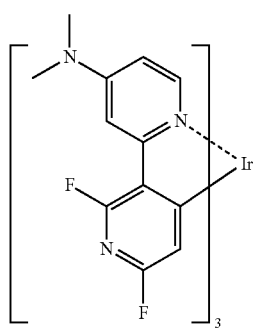
PD10 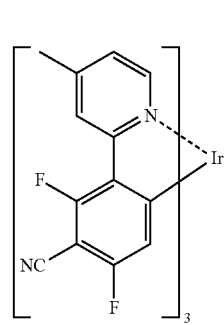
PD6 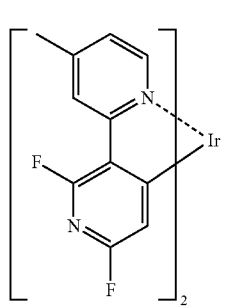
PD11 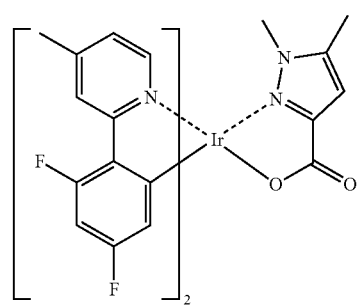

PD12 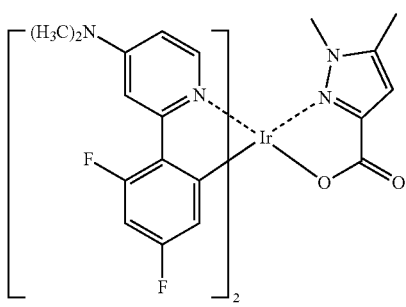
PD17 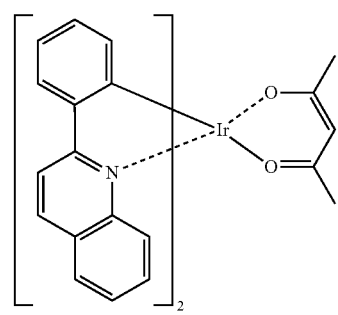
PD13 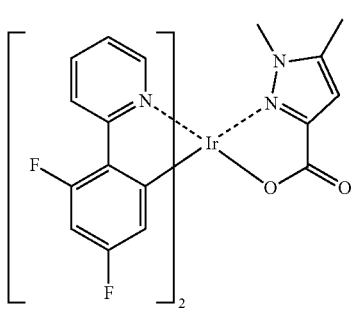
PD18 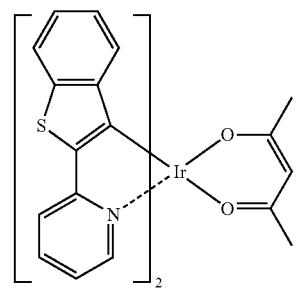
PD14 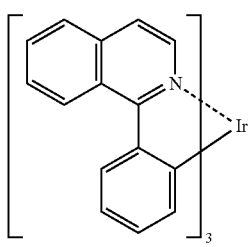
PD15 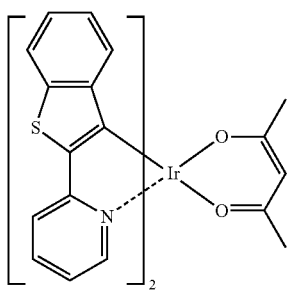
PD19 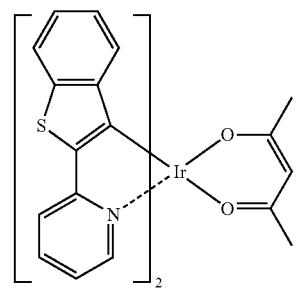
PD16 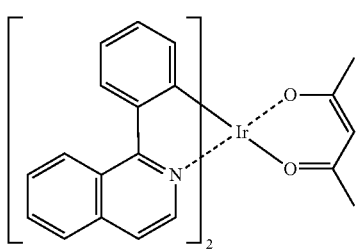
PD20 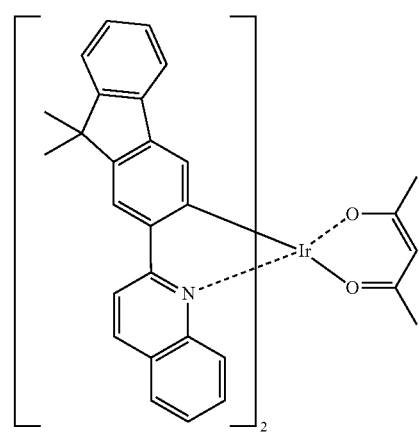

PD21
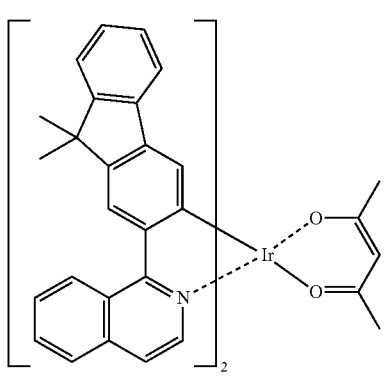
PD22
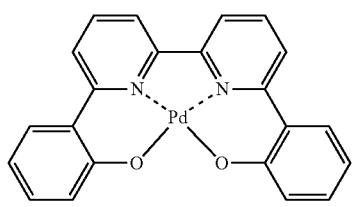
PD23
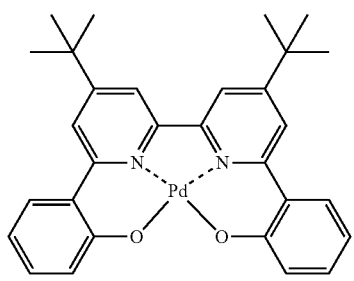
PD24
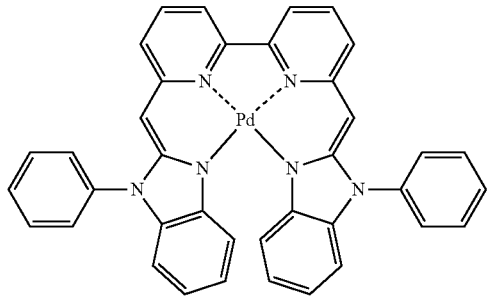
PD25
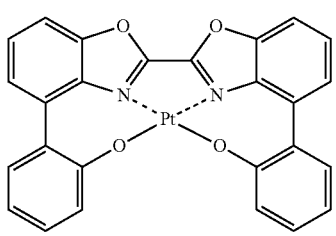
PD26
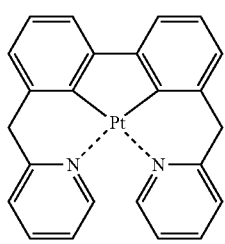
PD27
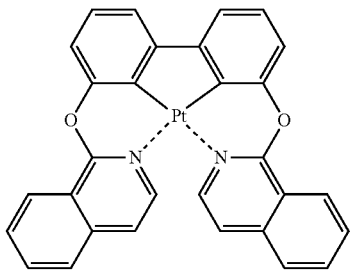
PD28
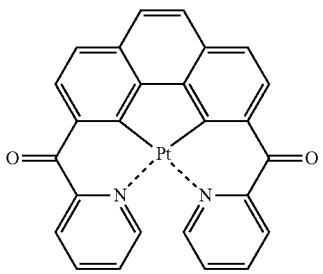
PD29
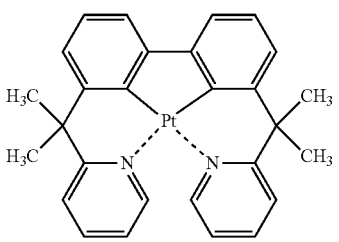
PD30
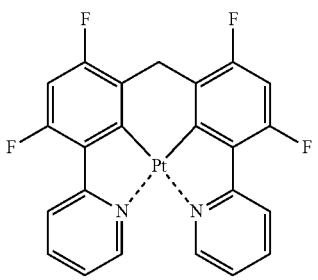
PD31
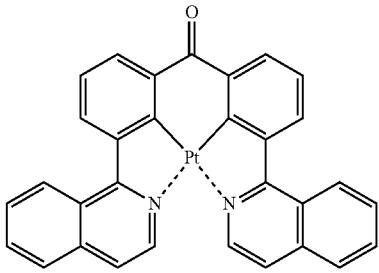
PD32
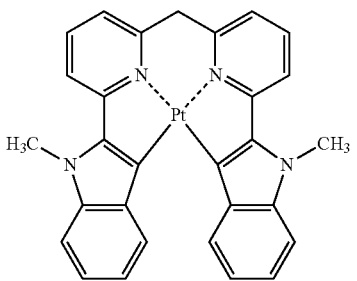

-continued
PD33
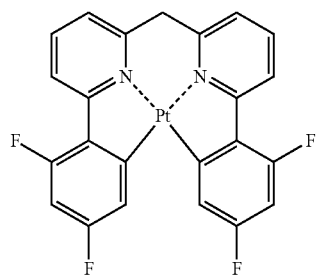
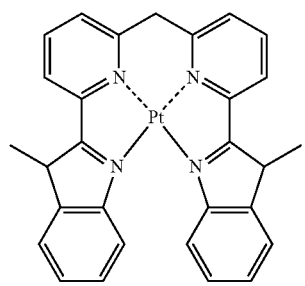
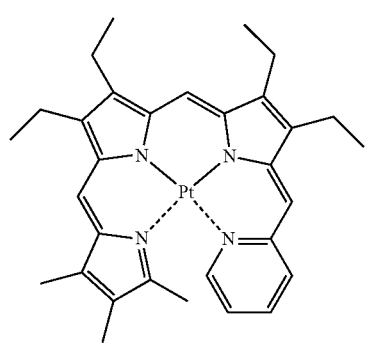
PD36
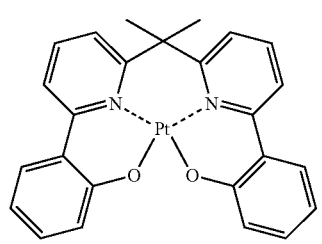
PD37
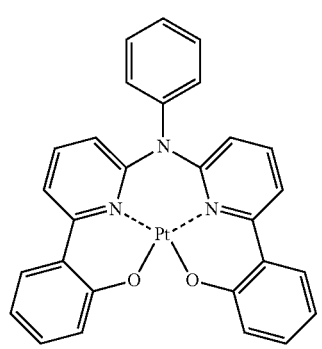
-continued
PD38
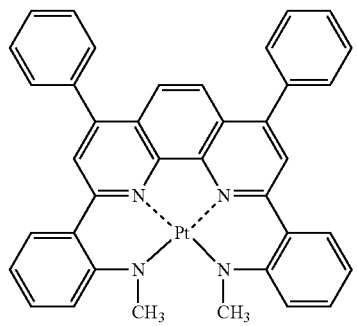
PD39
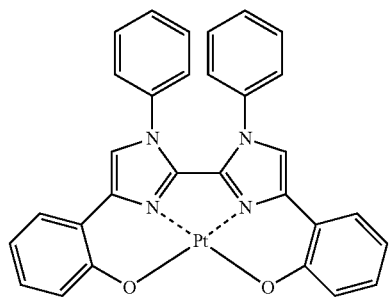
PD40
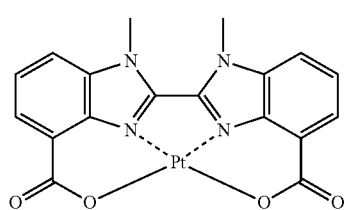
PD41
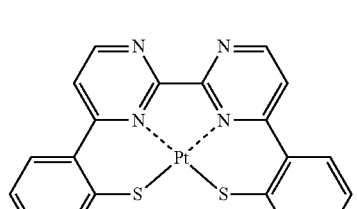
PD42
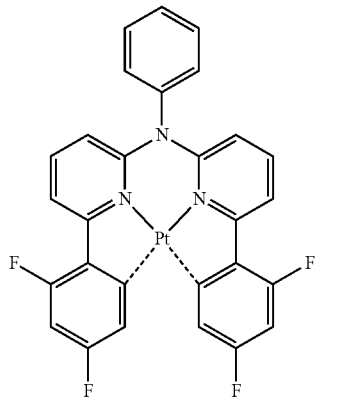

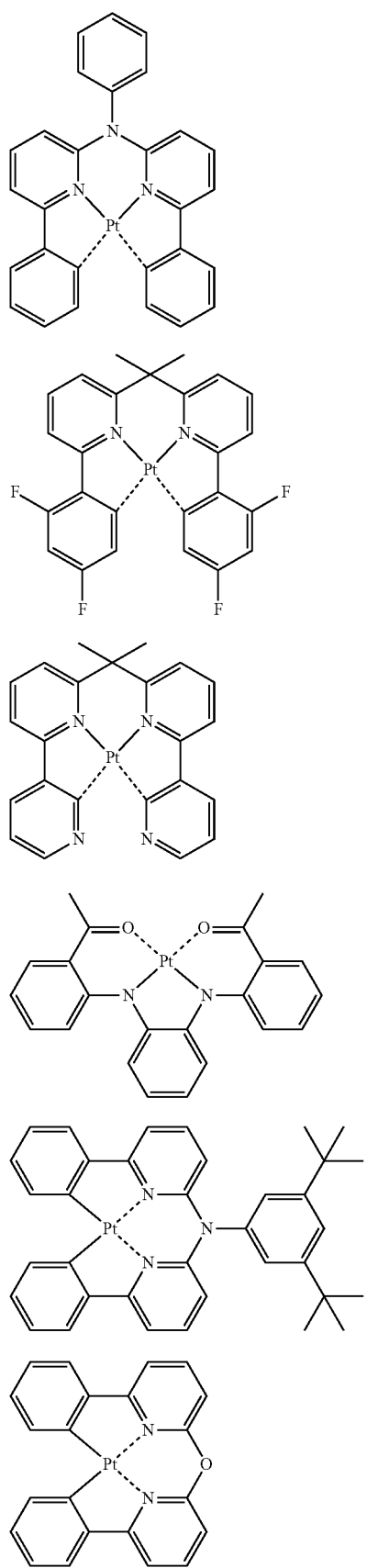
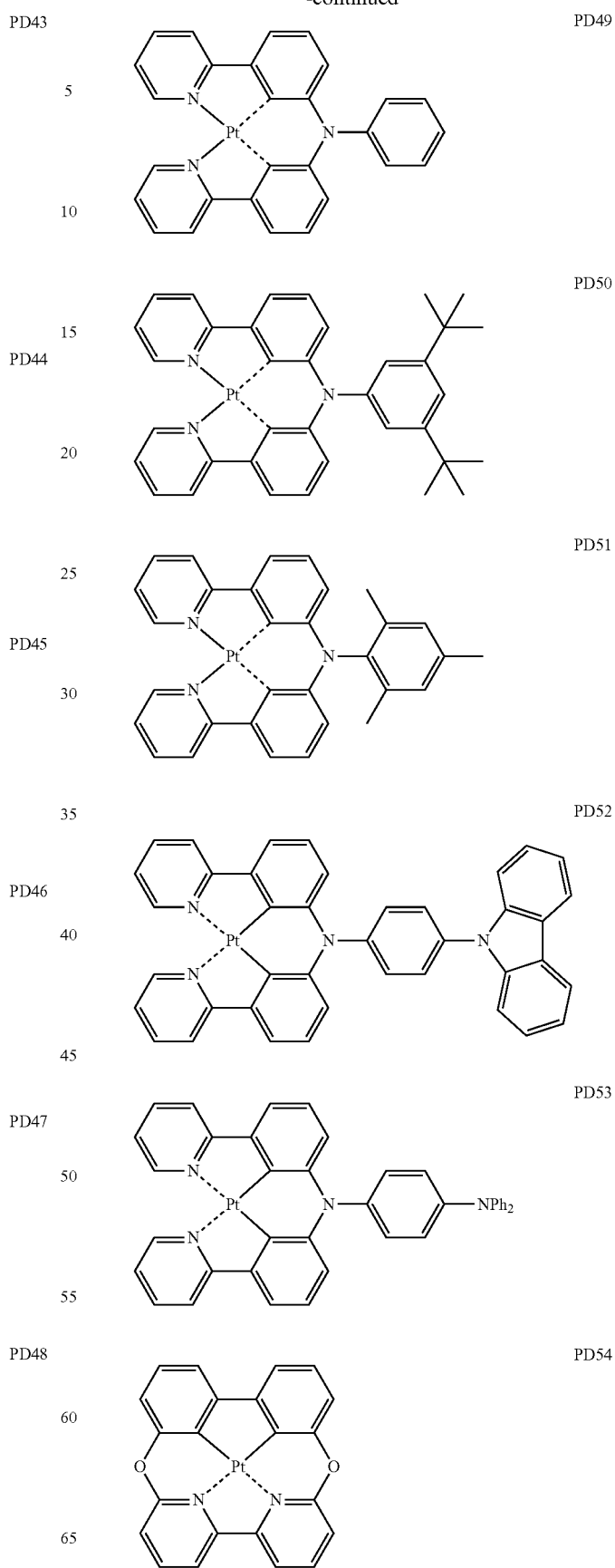

PD55
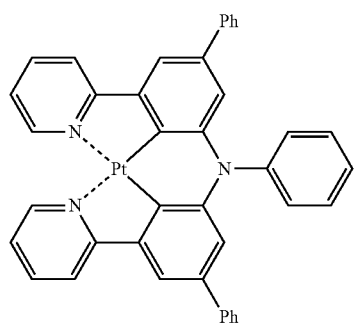
PD56
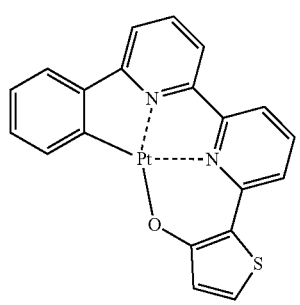
PD57
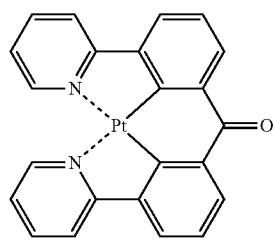
PD58
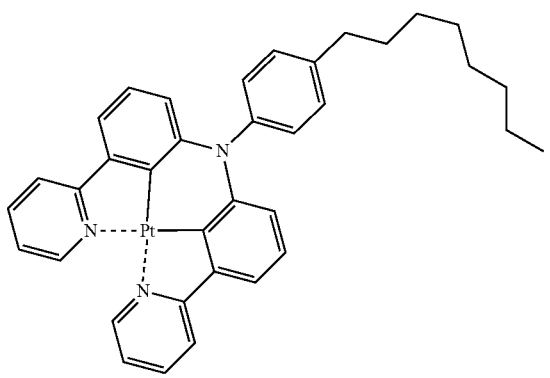
PD59
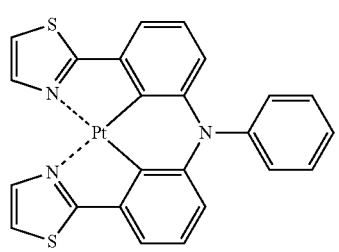
PD60
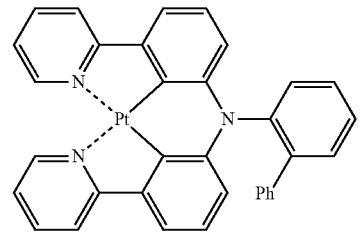
PD61
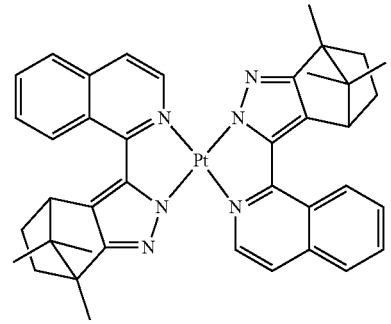
PD62
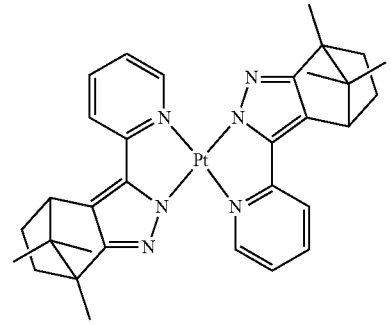
PD63
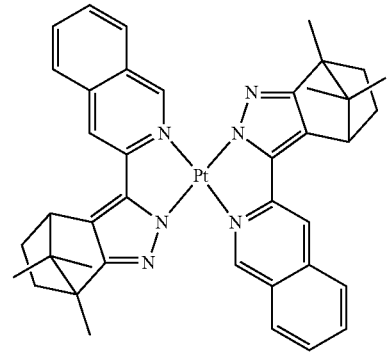
PD64
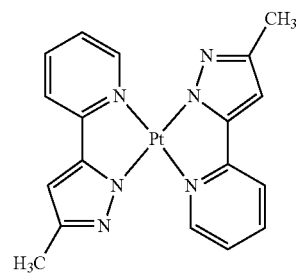

-continued
PD65 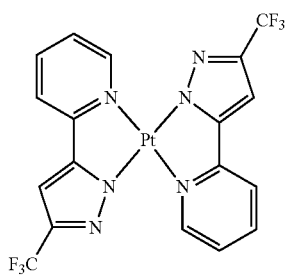
PD66 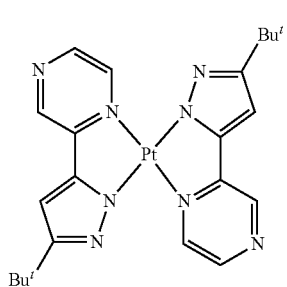
PD67 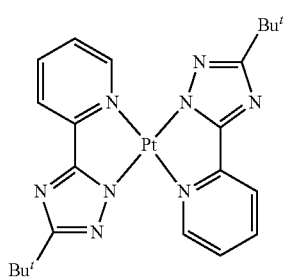
PD68 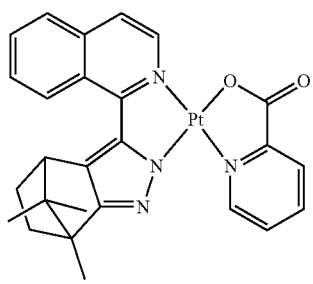
PD69 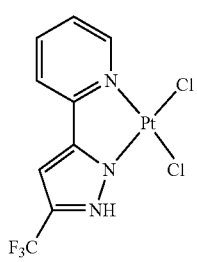
-continued
PD70 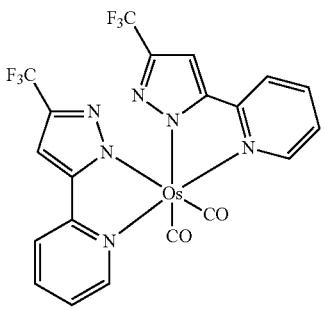
PD71 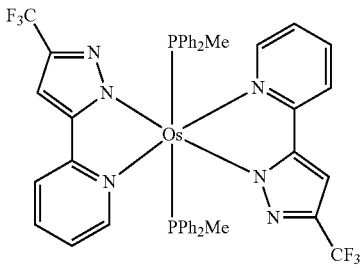
PD72 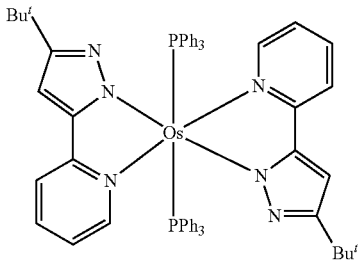
PD73 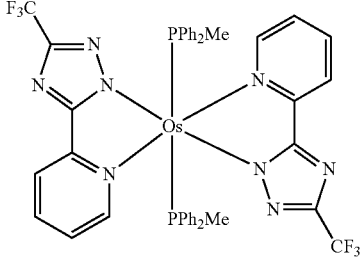
PD74 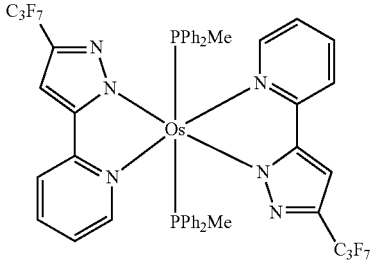
PD75 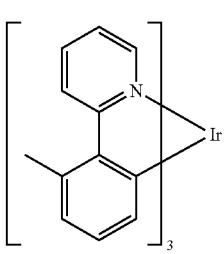

PD76
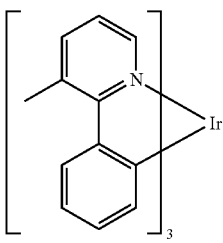

PD77
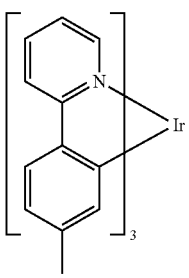

PD78
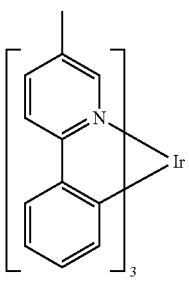

Fir6
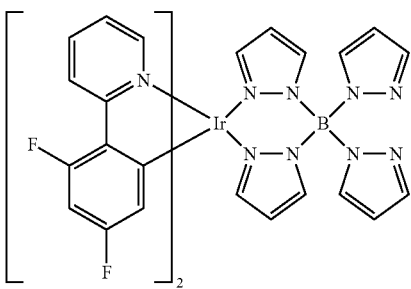

In some embodiments, the phosphorescent dopant may include PtOEP:

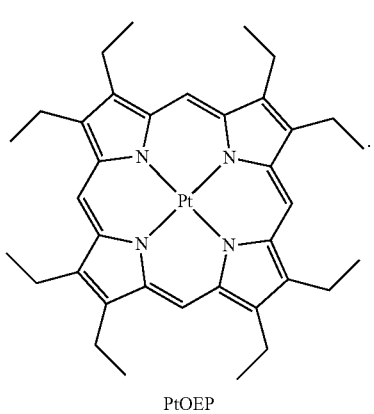

PtOEP

When the emission layer includes the host and the dopant, an amount of the dopant may be selected from a range of about 0.01 parts to about 20 parts by weight based on about 100 parts by weight of the host, but embodiments are not limited thereto.

The thickness of the emission layer may be in a range of about 100 Å to about 1,000 Å, and in some embodiments, about 200 Å to about 600 Å. While not wishing to be bound by theory, it is understood that when the thickness of the emission layer is within any of these ranges, improved luminescence characteristics may be obtained without a substantial increase in driving voltage.

Next, an electron transport region may be formed on the emission layer.

The electron transport region may include at least one selected from a hole blocking layer, an electron transport layer, and an electron injection layer.

In some embodiments, the electron transport region may have a hole blocking layer/an electron transport layer/an electron injection layer structure or an electron transport layer/an electron injection layer structure, but embodiments are not limited thereto. The electron transport layer may have a single-layered structure or a multi-layered structure including two or more different materials.

The conditions for forming a hole blocking layer, an electron transport layer, and an electron injection layer may be inferred based on the conditions for forming the hole injection layer.

When the electron transport region includes a hole blocking layer, the hole blocking layer, for example, may include at least one of BCP and Bphen, but embodiments are not limited thereto:

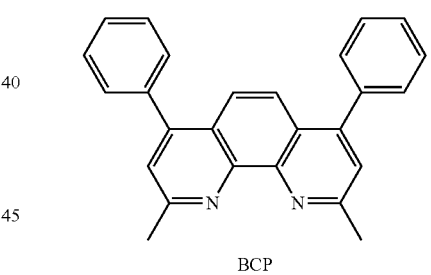

BCP

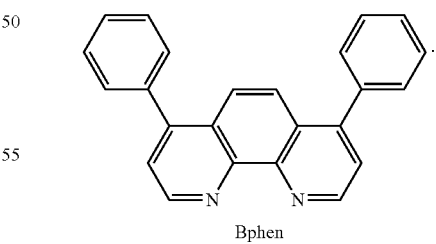

Bphen

The thickness of the hole blocking layer may be in a range of about 20 Å to about 1,000 Å, for example, about 30 Å to about 300 Å. While not wishing to be bound by theory, it is understood that when the thickness of the hole blocking layer is within any of these ranges, excellent hole blocking characteristics may be obtained without a substantial increase in driving voltage.

The electron transport layer may further include at least one selected from BCP, BPhen, Alq₃, BAlq, TAZ, and NTAZ:

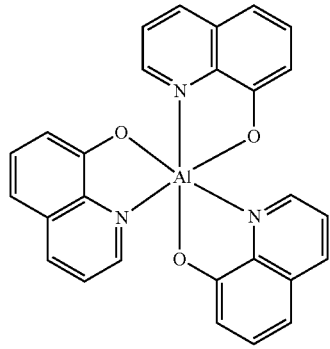

Alq₃

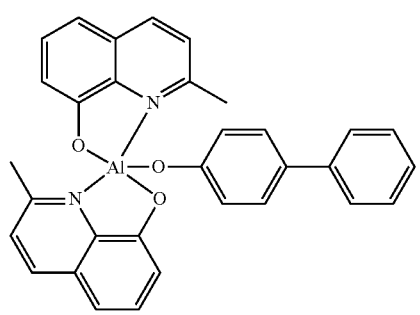

BAlq

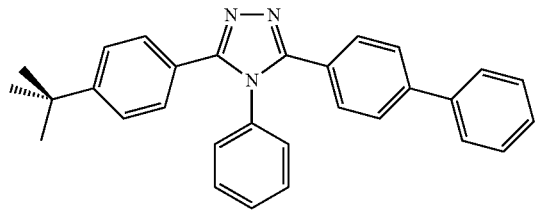

TAZ

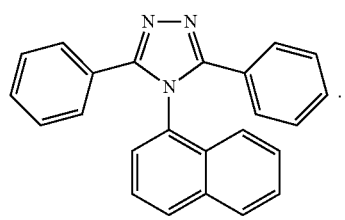

NTAZ

In some embodiments, the electron transport layer may include at least one selected from Compounds ET1, ET2, and ET3, but embodiments are not limited thereto:

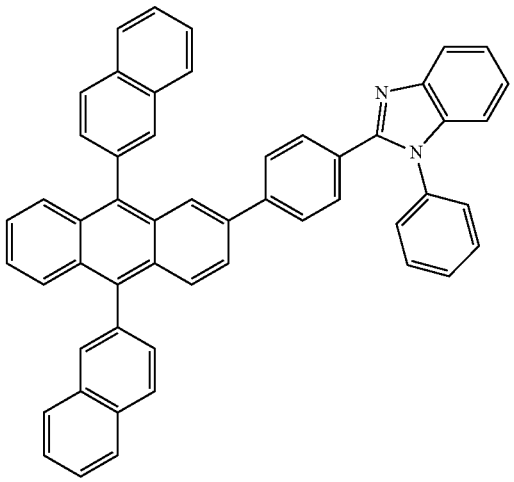

ET1

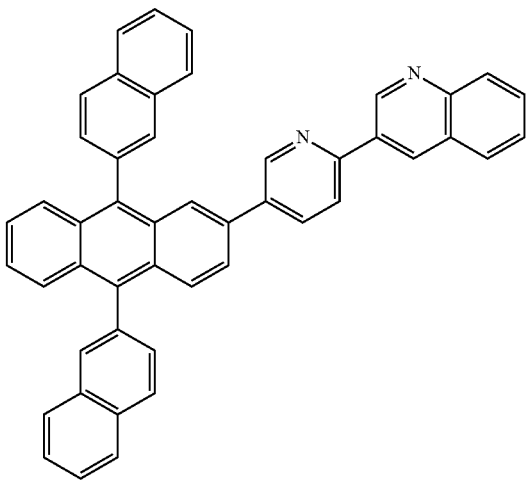

ET2

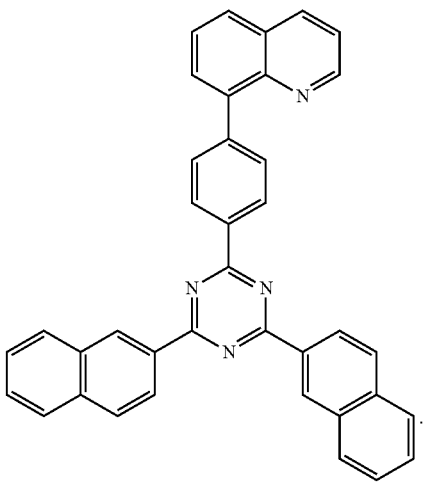

ET3

The thickness of the electron transport layer may be in a range of about 100 Å to about 1,000 Å, and in some embodiments, about 150 Å to about 500 Å. While not wishing to be bound by theory, it is understood that when the thickness of the electron transport layer is within any of these ranges, excellent electron transport characteristics may be obtained without a substantial increase in driving voltage.

The electron transport layer may further include a material containing metal, in addition to the materials described above.

The material containing metal may include a lithium (Li) complex. The Li complex may include, e.g., Compound ET-D1 (lithium 8-hydroxyquinolate, LiQ) or Compound ET-D2:

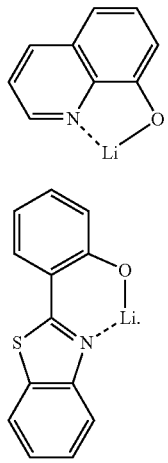

ET-D1

ET-D2

The electron transport region may include an electron injection layer that facilitates electron injection from the second electrode 19.

The electron injection layer may include at least one selected from LiQ, LiF, NaCl, CsF, $Li_2O$, and BaO.

The thickness of the electron injection layer may be in a range of about 1 Å to about 100 Å, and in some embodiments, about 3 Å to about 90 Å. While not wishing to be bound by theory, it is understood that when the thickness of the electron injection layer is within any of these ranges, excellent electron injection characteristics may be obtained without a substantial increase in driving voltage.

The second electrode 19 may be on the organic layer 15. The second electrode 19 may be a cathode. A material for forming the second electrode 19 may be a material with a relatively low work function, such as a metal, an alloy, an electrically conductive compound, and a mixture thereof. Examples of the material for forming the second electrode 19 may include lithium (Li), magnesium (Mg), aluminum (Al), aluminum-lithium (Al—Li), calcium (Ca), magnesium-indium (Mg—In), and magnesium-silver (Mg—Ag). In some embodiments, ITO or IZO may be used to form a transmissive second electrode 19 to manufacture a top emission light-emitting device. In some embodiments, the material for forming the second electrode 19 may vary.

In an embodiment, the organic layer 15 in the organic light-emitting device 10 may include a hole transport region and an emission layer, wherein the hole transport region and the emission layer may each include the condensed cyclic compound represented by Formula 1, provided that the condensed cyclic compound represented by Formula 1 included in the hole transport region may be identical to the condensed cyclic compound represented by Formula 1 included in the emission layer.

In an embodiment, the organic layer 15 in the organic light-emitting device 10 may include a hole transport region and an emission layer, wherein the hole transport region and the emission layer may each include the condensed cyclic compound represented by Formula 1, provided that the condensed cyclic compound represented by Formula 1 included in the hole transport region may be different from to the condensed cyclic compound represented by Formula 1 included in the emission layer.

Here, the hole transport region may include at least one of a hole transport layer and an electron blocking layer, wherein the condensed cyclic compound represented by Formula 1 may be included i) in the hole transport layer; ii) in the electron blocking layer; or iii) in both of the hole transport layer and the electron blocking layer. The electron blocking layer may be in a direct contact with the emission layer.

Hereinbefore the organic light-emitting device 10 has been described with reference to FIG. 1, but embodiments are not limited thereto.

The term "$C_1$-$C_{60}$ alkyl group" as used herein refers to a linear or branched saturated aliphatic hydrocarbon monovalent group having 1 to 60 carbon atoms. Examples thereof include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group" as used herein refers to a divalent group having substantially the same structure as the $C_1$-$C_{60}$ alkyl group.

The term "$C_1$-$C_{60}$ alkoxy group" as used herein refers to a monovalent group represented by —$OA_{101}$ (wherein $A_{101}$ is a $C_1$-$C_{60}$ alkyl group). Examples thereof include a methoxy group, an ethoxy group, and an iso-propyloxy group.

The term "$C_2$-$C_{60}$ alkenyl group" as used herein refers to a group formed by placing at least one carbon double bond in the middle or at the terminus of the $C_2$-$C_{60}$ alkyl group. Examples thereof include an ethenyl group, a propenyl group, and a butenyl group. The term "$C_2$-$C_{60}$ alkenylene group" as used herein refers to a divalent group having substantially the same structure as the $C_2$-$C_{60}$ alkenyl group.

The term "$C_2$-$C_{60}$ alkynyl group" as used herein refers to a group formed by placing at least one carbon triple bond in the middle or at the terminus of the $C_2$-$C_{60}$ alkyl group. Examples thereof include an ethenyl group and a propenyl group. The term "$C_2$-$C_{60}$ alkynylene group" as used herein refers to a divalent group having substantially the same structure as the $C_2$-$C_{60}$ alkynyl group.

The term "$C_3$-$C_{10}$ cycloalkyl group" as used herein refers to a monovalent monocyclic saturated hydrocarbon group including 3 to 10 carbon atoms. Examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having substantially the same structure as the $C_3$-$C_{10}$ cycloalkyl group.

The term "$C_1$-$C_{10}$ heterocycloalkyl group" as used herein refers to a monovalent monocyclic group including at least one heteroatom selected from N, O, P, Si, and S as a ring-forming atom and 1 to 10 carbon atoms. Examples thereof include a tetrahydrofuranyl group and a tetrahydrothiophenyl group. The term "$C_1$-$C_{10}$ heterocycloalkylene group" as used herein refers to a divalent group having substantially the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one double bond in its ring, and is not aromatic. Examples thereof include a cyclopentenyl group, a cyclohexenyl group, and a cycloheptenyl group. The term "$C_3$-$C_{10}$ cycloalkenylene group" as used herein refers to a divalent group having substantially the same structure as the $C_3$-$C_{10}$ cycloalkenyl group.

The term "$C_1$-$C_{10}$ heterocycloalkenyl group" as used herein refers to a monovalent monocyclic group including at least one heteroatom selected from N, O, P, Si, and S as a ring-forming atom, 1 to 10 carbon atoms, and at least one double bond in its ring. Examples of the $C_2$-$C_{10}$ heterocycloalkenyl group include a 2,3-hydrofuranyl group and a 2,3-hydrothiophenyl group. The term "$C_1$-$C_{10}$ heterocycloalkylene group" as used herein refers to a divalent group having substantially the same structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms. The term "$C_6$-$C_{60}$ arylene group" as used herein refers to a divalent group having a carbocyclic aromatic system having 6 to 60 carbon atoms. Examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and a $C_6$-$C_{60}$ arylene group each include at least two rings, the at least two rings may be fused.

The term "$C_1$-$C_{60}$ heteroaryl group" as used herein refers to a monovalent group having a carbocyclic aromatic system having at least one heteroatom selected from N, O, P, and S as a ring-forming atom and 1 to 60 carbon atoms. The term "$C_1$-$C_{60}$ heteroarylene group" as used herein refers to a divalent group having a carbocyclic aromatic system having at least one heteroatom selected from N, O, P, and S as a ring-forming atom and 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include at least two rings, the at least two rings may be fused.

The term "$C_6$-$C_{60}$ aryloxy group" as used herein refers to a group represented by —$OA_{102}$ (where $A_{102}$ is a $C_6$-$C_{60}$ aryl group). The term "$C_6$-$C_{60}$ arylthio group" as used herein refers to a group represented by —$SA_{103}$ (where $A_{103}$ is a $C_6$-$C_{60}$ aryl group).

The term "monovalent non-aromatic condensed polycyclic group" as used herein refers to a monovalent group having two or more rings condensed and only carbon atoms (for example, the number of carbon atoms may be in a range of 8 to 60) as ring-forming atoms, wherein the molecular structure as a whole is non-aromatic. Examples of the non-aromatic condensed polycyclic group include a fluorenyl group. The term "divalent non-aromatic condensed polycyclic group" as used herein refers to a divalent group having substantially the same structure as the monovalent non-aromatic condensed polycyclic group.

The term "monovalent non-aromatic condensed heteropolycyclic group" as used herein refers to a monovalent group having at least two rings condensed and a heteroatom selected from N, O, P, Si, and S as well as carbon atoms (for example, the number of carbon atoms may be in a range of 1 to 60) as ring-forming atoms, wherein the molecular structure as a whole is non-aromatic. Examples of the monovalent non-aromatic condensed heteropolycyclic group include a carbazolyl group. The term "divalent non-aromatic condensed heteropolycyclic group" as used herein refers to a divalent group having substantially the same structure as the monovalent non-aromatic condensed heteropolycyclic group.

In Formula 1 of the present specification, at least one substituent of the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —$CD_3$, —$CD_2H$, —$CDH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_{60}$ alkoxy group, each substituted with at least one selected from deuterium, —$CD_3$, —$CD_2H$, —$CDH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{14})(Q_{15})$, and —$B(Q_{16})(Q_{17})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group and a monovalent non-aromatic condensed heteropolycyclic group, each substituted with at least one selected from deuterium, —$CD_3$, —$CD_2H$, —$CDH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$N(Q_{24})(Q_{25})$, and —$B(Q_{26})(Q_{27})$; and —$Si(Q_{31})(Q_{32})(Q_{33})$, —$N(Q_{34})(Q_{35})$, and —$B(Q_{36})(Q_{37})$, wherein $Q_1$ to $Q_7$, $Q_{11}$ to $Q_{17}$, $Q_{21}$ to $Q_{27}$, and $Q_{31}$ to $Q_{37}$ may each independently be selected from hydrogen, deuterium, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

The term "biphenyl group" as used herein refers to a monovalent group in which two phenyl groups are bound to each other via a single bond.

The term "terphenyl group" as used herein refers to a monovalent group in which three phenyl groups are bound to each other via a single bond.

Hereinafter, a compound and an organic light-emitting device according to an embodiment will be described in detail with reference to Synthesis Examples and Examples, however, the present disclosure is not limited thereto. The wording "B was used instead of A" used in describing Synthesis Examples means that an identical molar equivalent of B was used in place of A.

EXAMPLES

Synthesis Example 1: Synthesis of Compound 1

1) Synthesis of Intermediate 1-A

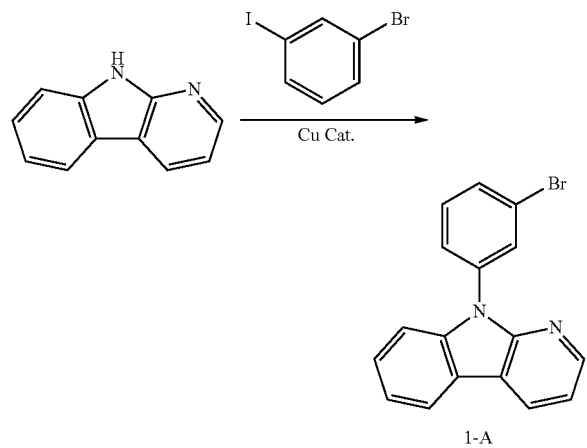

15 grams (g) (89.18 mmol) of α-carboline, 75.7 g (267.54 mmol) of 3-bromoiodobenzene, 5.1 g (26.75 mmol) of CuI, 37.9 g (178.36 mmol) of $K_3PO_4$, and 3.1 g (26.75 mmol) of trans-1,2-diaminocyclohexane were added to a 1 liter (L) flask. Then, 450 milliliters (mL) of dioxane was added thereto, followed by stirring under reflux at a temperature of 110° C. for 36 hours. Once the reaction was complete, the temperature was lowered, and ethyl acetate was added thereto to extract an organic layer, followed by removal of the solution. The resulting product was purified through column chromatography to thereby obtain Intermediate 1-A. (yield: 36%)

2) Synthesis of Compound 1

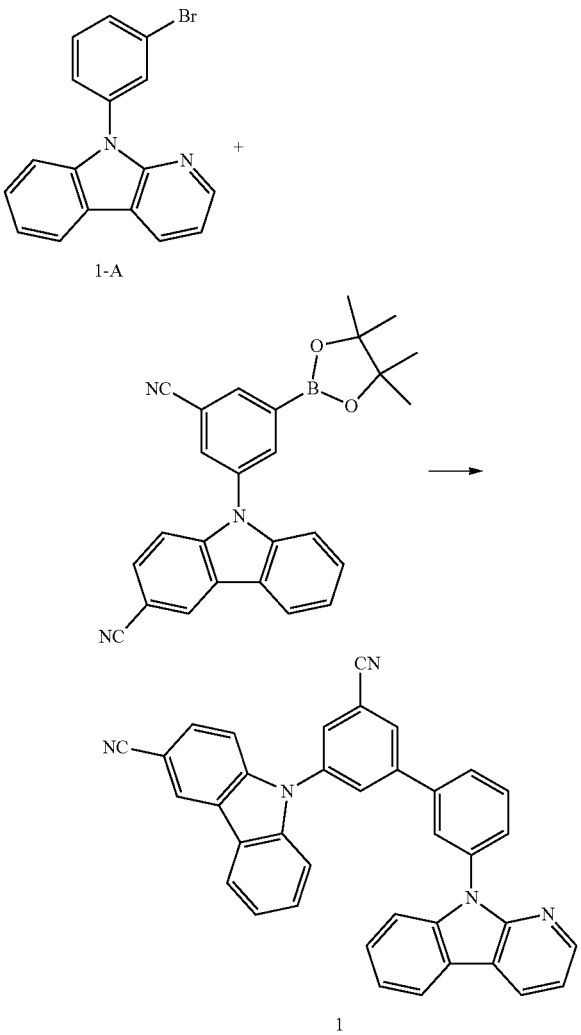

7 g (21.66 mmol) of Intermediate 1-A, 10.9 g (25.99 mmol) of 9-(3-cyano-5-(4,4,5,5-tetramethyl-1,3,2-dioxaborolan-2-yl)phenyl)-9H-carbazole-3-carbonitrile, 0.05 molar (M) of palladium catalyst, and 8.9 g (64.98 mmol) of potassium carbonate were added to a 1 L flask. Then, 100 mL of a mixture of tetrahydrofuran and water at a ratio of 1:1 was added thereto. The reaction continued at a temperature of 80° C. for 6 hours. Once the temperature was lowered, methanol was added thereto to precipitate a solid. The solid was then filtered. The resulting filtered solid was recrystallized using dimethyl formamide to thereby obtain Compound 1. (yield: 30%)

MALDI-MS Calcd: (535.18), Found: (535.2).

Evaluation Example 1: Evaluation of HOMO, LUMO, and Triplets ($T_1$) Energy Levels The HOMO, LUMO, and $T_1$ energy levels of Compound 1 and Comparative Compounds A to F were evaluated according to the method described in Table 2. The results thereof are shown in Table 3.

TABLE 2

| | |
|---|---|
| HOMO energy level evaluation method | A potential (Volts, V)-current (Amperes, A) graph of each compound was obtained by using cyclic voltammetry (CV) (electrolyte: 0.1M Bu$_4$NClO$_4$/solvent: CH$_2$Cl$_2$/electrode: 3 electrode system (working electrode: GC, reference electrode: Ag/AgCl, auxiliary electrode: Pt)). Then, from reduction onset of the graph, a HOMO energy level of a compound was calculated. |
| LUMO energy level evaluation method | Each compound was diluted at a concentration of 1 × 10$^{-5}$M in CHCl$_3$, and a UV absorption spectrum thereof was measured at room temperature by using a Shimadzu UV-350 spectrometer. Then a LUMO energy level thereof was calculated by using an optical band gap ($E_g$) from an edge of the absorption spectrum. |
| $T_1$ energy level evaluation method | A mixture (each compound was dissolved in an amount of 1 milligram (mg) in 3 cubic centimeters (cc) of toluene) of toluene and each compound was loaded into a quartz cell. Subsequently, the resultant quartz cell was loaded into liquid nitrogen (77 Kelvins (K)), a photoluminescence spectrum thereof was measured by using a device for measuring photoluminescence. The obtained spectrum was compared with a photoluminescence spectrum measured at room temperature, and peaks observed only at a low temperature were analyzed to calculate $T_1$ energy levels. |

TABLE 3

| Compound No. | HOMO (eV) (measured) | LUMO (eV) (measured) | $T_1$ energy level (eV) |
|---|---|---|---|
| Compound 1 | −5.97 | −2.46 | 2.92 |
| Comparative Compound A | −5.68 | −2.12 | 2.81 |
| Comparative Compound B | −5.77 | −2.18 | 3.01 |
| Comparative Compound C | −5.68 | −2.11 | 2.81 |
| Comparative Compound D | −5.61 | −1.7 | 2.75 |
| Comparative Compound E | −5.42 | −1.64 | 3.01 |
| Comparative Compound F | −5.43 | −1.82 | 2.78 |

Comparative Compound A

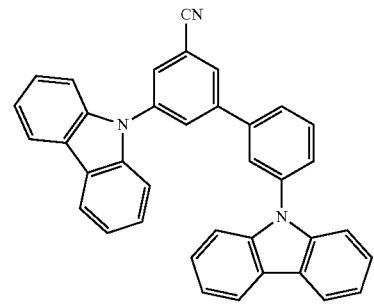 [SMILES: N#Cc1cc(-c2cccc(-n3c4ccccc4c4ccccc43)c2)cc(-n2c3ccccc3c3ccccc32)c1]

Comparative Compound B

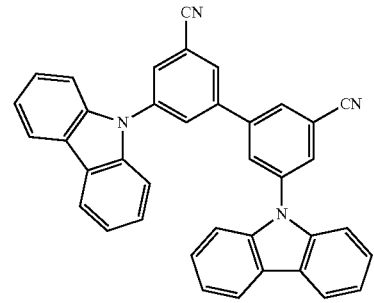 [SMILES: N#Cc1cc(-c2cc(C#N)cc(-n3c4ccccc4c4ccccc43)c2)cc(-n2c3ccccc3c3ccccc32)c1]

Comparative Compound C

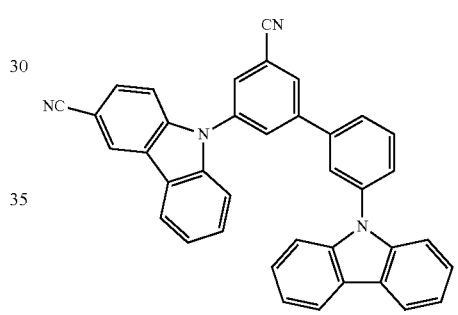

Comparative Compound D

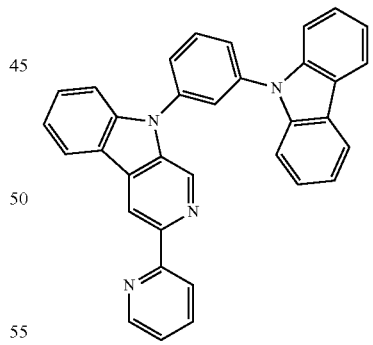

Comparative Compound E

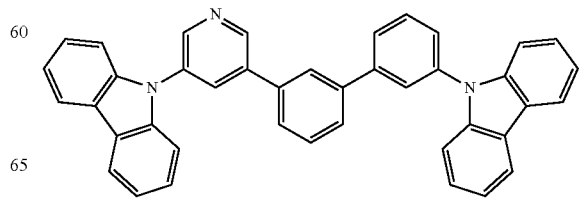

TABLE 3-continued

| Compound No. | HOMO (eV) (measured) | LUMO (eV) (measured) | T₁ energy level (eV) |
|---|---|---|---|
| Comparative Compound F | | | |

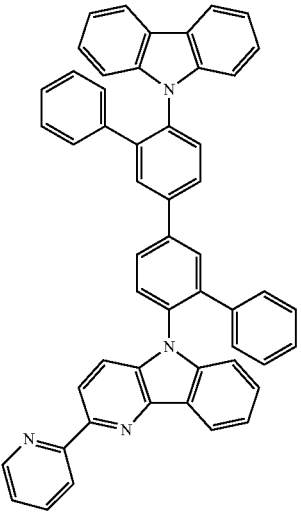 [SMILES: c1ccc(-c2cc(-c3ccc(-n4c5ccccc5c5nc(-c6ccccn6)ccc54)c(-c4ccccc4)c3)ccc2-n2c3ccccc3c3ccccc32)cc1]

Referring to Table 3, it was found that the compounds according to one or more embodiments have electrical characteristics that are suitable for use as a material for forming an organic light-emitting device.

Evaluation Example 2: Thermal Characteristics Evaluation

Thermal analysis ($N_2$ atmosphere, temperature range: from room temperature to about 800° C. (10° C./min)-thermo gravimetric analysis (TGA), from room temperature to 400° C.-differential scanning calorimetry (DSC), Pan Type: Pt Pan in disposable Al Pan (TGA) and disposable Al pan (DSC)) was performed on Compounds 1 and Comparative Compounds A to F by using TGA and DSC. The evaluation results are shown in Table 4. As shown in Table 4, it was found that the compounds one or more embodiments have excellent thermal stability.

TABLE 4

| Compound No. | $T_g$(° C.) |
|---|---|
| Compound 1 | 373 |
| Comparative Compound A | 347 |
| Comparative Compound B | 316 |
| Comparative Compound C | 341 |
| Comparative Compound D | 280 |
| Comparative Compound E | 285 |
| Comparative Compound F | 332 |

Example 1

A glass substrate having 1,500 Å of indium tin oxide (ITO) electrode (first electrode, anode) deposited thereon was washed with distilled water in the presence of ultrasound waves. Once the washing with distilled water was complete, ultrasound wave washing was performed on the substrate using a solvent, such as iso-propyl alcohol, acetone, or methanol. Subsequently, the substrate was dried, transferred to a plasma washer, washed for 5 minutes using oxygen plasma, and mounted in a vacuum depositor.

Compound HT3 was vacuum-deposited on the ITO electrode of the glass substrate to form a hole injection layer having a thickness of 100 Å, and Compound HT13 was deposited on the hole injection layer to form a hole transport layer having a thickness of 1,300 Å, thereby forming a hole transport region.

Subsequently, Compound 1 (host) and Compound FIr₆ (dopant, 10 weight %) were co-deposited on the hole transport region to form an emission layer having a thickness of 300 Å.

Compound ET3 and Liq were vacuum-deposited on the emission layer to form an electron transport layer having a thickness of 250 Å, Liq was deposited on the electron transport layer to form an electron injection layer having a thickness of 5 Å, and an Al second electrode (a cathode) was formed on the electron injection layer to have a thickness of 1,000 Å, thereby completing the manufacture of an organic light-emitting device.

HT3

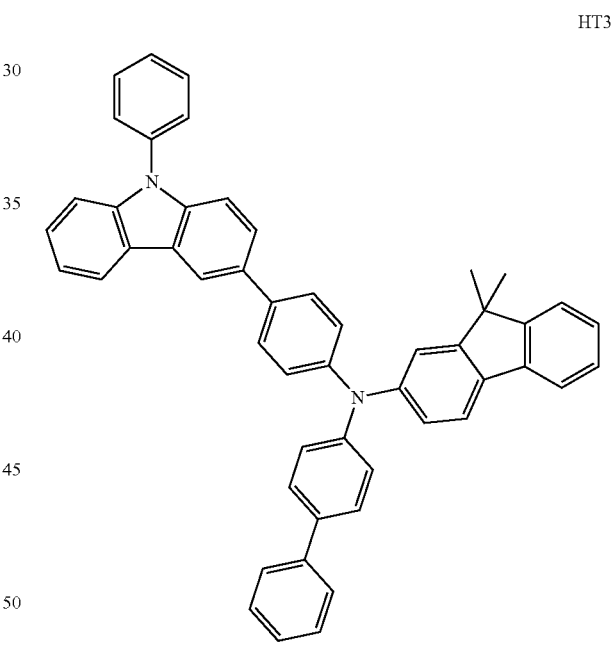

HT13

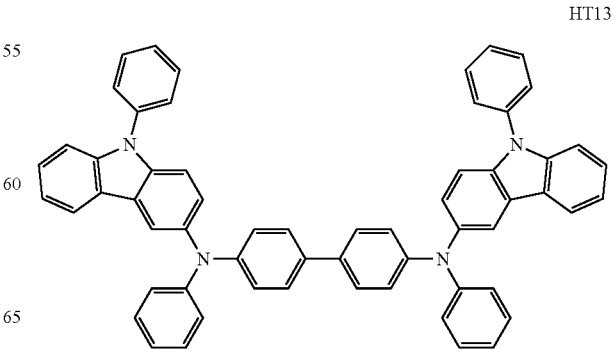

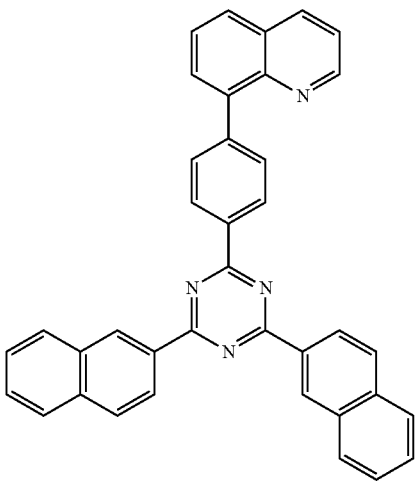

ET3

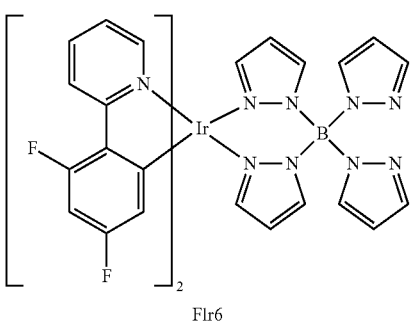

FIr6

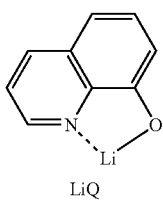

LiQ

Comparative Examples 1 to 6

Organic light-emitting devices were manufactured in substantially the same manner as in Example 1, except that the compounds shown in Table 5 were used instead of Compound 6 as a host in the formation of an emission layer.

Evaluation Example 3: Evaluation of Characteristics of Organic Light-Emitting Device The driving voltage, current density, efficiency, power efficiency, quantum efficiency, and lifespan of the organic light-emitting devices manufactured in Example 1 and Comparative Examples 1 to 6 were measured by using a current voltmeter (Keithley 2400) and a luminance meter (Minolta Cs-1000A). The evaluation results calculated relative to the values of Comparative Example 1 are shown in Table 5.

In Table 5, $T_{95}$ is lifespan data evaluating a period taken for the luminance (at 500 candelas per square meter ($cd/m_2$)) to reach 95% with respect to 100% of the initial luminance.

TABLE 5

| | Host | Driving voltage (%) | Current efficiency (%) | Quantum efficiency (%) | Lifespan (%) |
|---|---|---|---|---|---|
| Example 1 | Compound 1 | 100.5 | 156.6 | 145 | 318.7 |
| Comparative Example 1 | Comparative Compound A | 100 | 100 | 100 | 100 |
| Comparative Example 2 | Comparative Compound B | 128.8 | 139 | 128.9 | 183 |
| Comparative Example 3 | Comparative Compound C | 94 | 117.8 | 101.1 | 240 |
| Comparative Example 4 | Comparative Compound D | 95.1 | 100 | 86.1 | 65.7 |
| Comparative Example 5 | Comparative Compound E | 152.2 | 100 | 95.6 | 51.3 |
| Comparative Example 6 | Comparative Compound F | 105.9 | 100 | 84.4 | 99.6 |

Referring to Table 5, it was found that the current efficiency and quantum efficiency of the organic light-emitting device of Example 1 was improved, as compared with those of the organic light-emitting devices of Comparative Examples 1 to 6. Also, the organic light-emitting device of Example 1 was found to have excellent lifespan characteristics, as compared with those of the organic light-emitting device of Comparative Examples 1 to 6.

As apparent from the foregoing description, the condensed cyclic compound according to one or more embodiments has excellent electrical characteristics and thermal stability. Accordingly, an organic light-emitting device including the condensed cyclic compound may have a low driving voltage, high efficiency, high luminance, long lifespan, and high color purity characteristics.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present description as defined by the following claims.

What is claimed is:

1. An organic light-emitting device comprising:
   a first electrode;
   a second electrode; and
   an organic layer disposed between the first electrode and the second electrode, wherein the organic layer comprises an emission layer and at least one condensed cyclic compound represented by Formulae 1-1 to 1-4,
   wherein the emission layer comprises a host and a fluorescent dopant, the host comprises the at least one condensed cyclic compound represented by Formulae 1-1 to 1-4, a content of the host is greater than a content of the fluorescent dopant and a ratio of emission components of the fluorescent dopant is 80% or greater of the whole emission components emitted from the emission layer 1-1
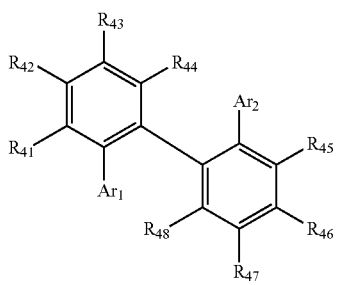
1-2
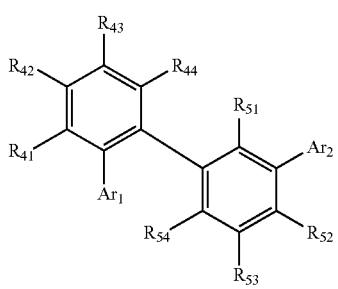
1-3
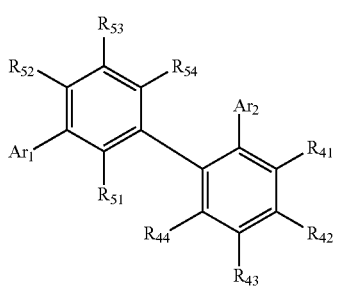
1-4
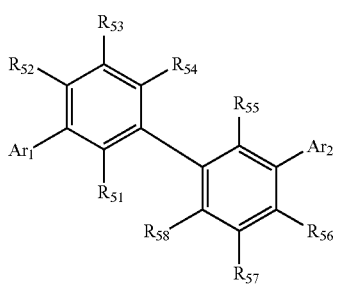
wherein, in Formulae 1-1 to 1-4,
Ar$_1$ is a group represented by one of Formulae 2-1 to 2-7, and Ar$_2$ is a group represented by one of Formulae 3-1 to 3-14:
2-1
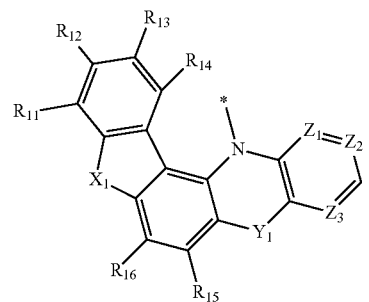
2-2
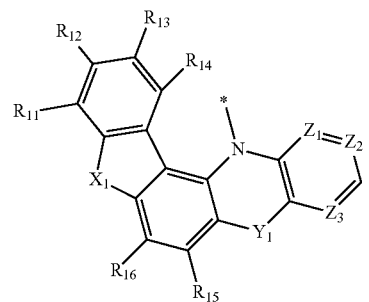
2-3
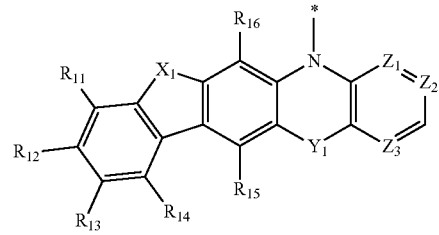
2-4
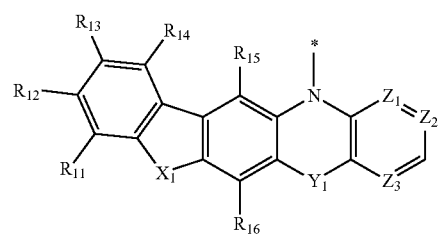
2-5
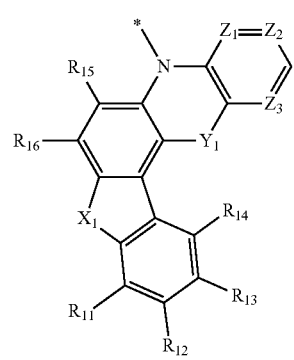
2-6
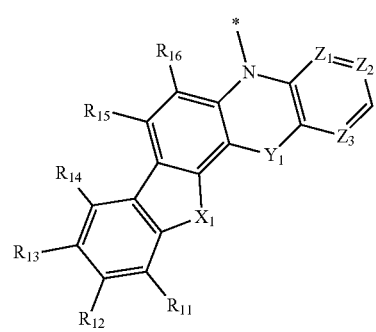

2-7
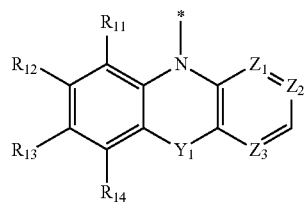
3-1
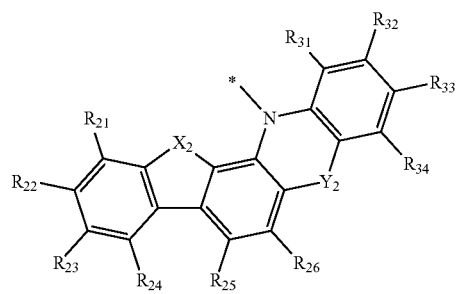
3-2
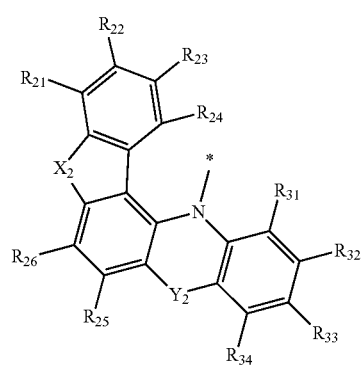
3-3
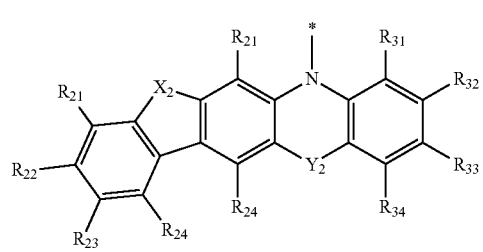
3-4
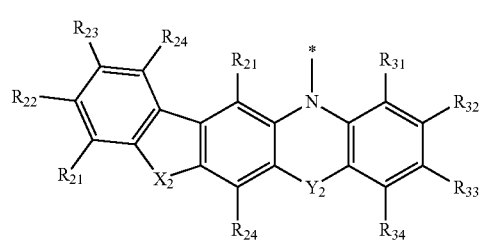
3-5
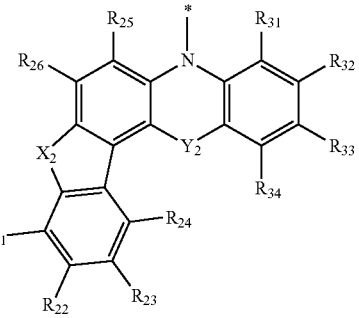
3-6
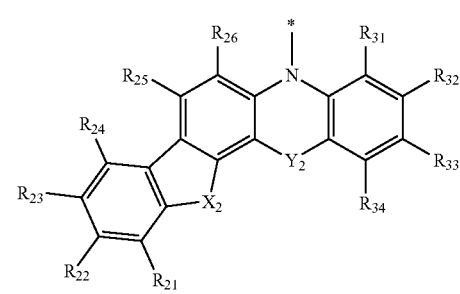
3-7
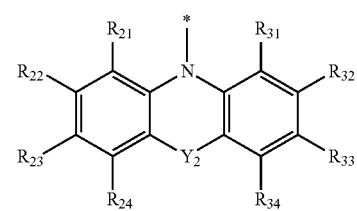
3-8
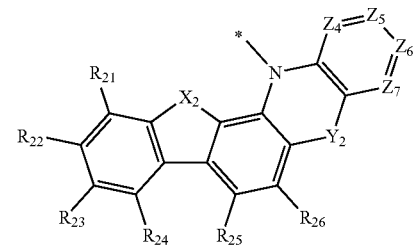
3-9
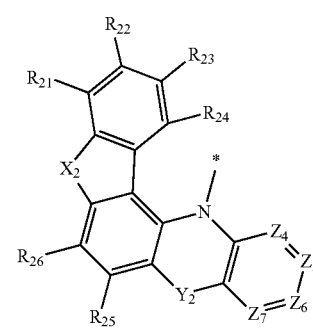

-continued

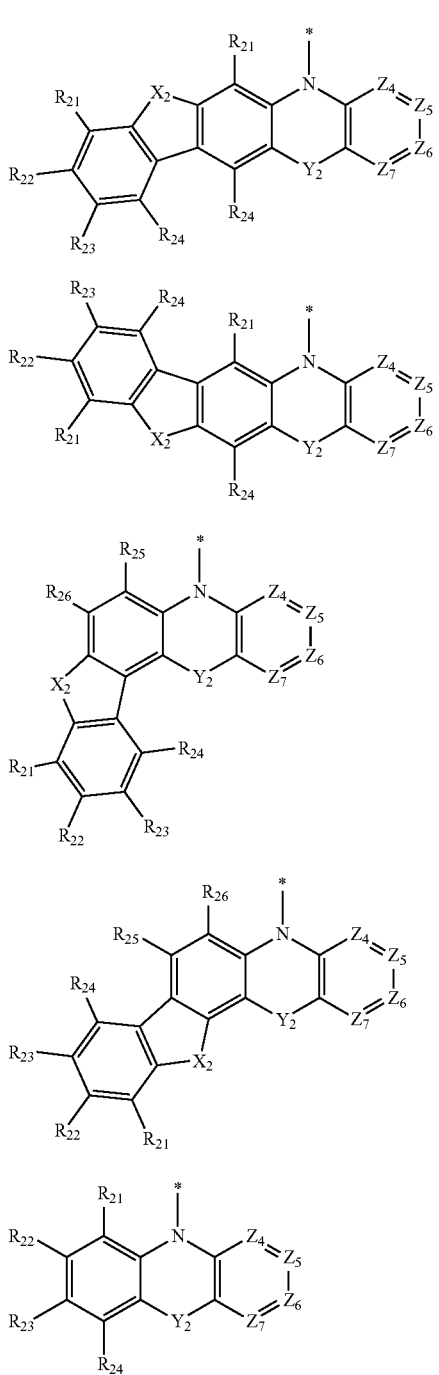

wherein:
$X_1$ is $C(R_{17})(R_{18})$, $N(R_{19})$, O, or S,
$X_2$ is $C(R_{27})(R_{28})$, $N(R_{29})$, O, or S,
$Z_1$ is N or $C(R_1)$, $Z_2$ is N or $C(R_2)$, $Z_3$ is N or $C(R_3)$, at least one selected from $Z_1$ to $Z_3$ is N,
$Y_1$ is a single bond, $C(R_4)(R_5)$, $N(R_4)$, O, or S,
$Y_2$ is a single bond, $C(R_6)(R_7)$, $N(R_6)$, O, or S,
$Z_4$ is N or $C(R_{31})$, $Z_5$ is N or $C(R_{32})$, $Z_6$ is N or $C(R_{33})$, $Z_7$ is N or $C(R_{34})$, at least one selected from $Z_4$ to $Z_7$ is N, and
provided that when the condensed cyclic compound is represented by Formula 1-4, $Ar_1$ is a group represented by Formula 2-7, $Ar_2$ is a group represented by Formulae 3-7, $Z_1$ is N, $Z_2$ is $C(R_2)$, $Z_3$ is $C(R_3)$, $Y_1$ and $Y_2$ are each a single bond, $R_2$, $R_3$, $R_{11}$ to $R_{14}$, $R_{21}$ to $R_{24}$, and $R_{31}$ to $R_{34}$, $R_{51}$ to $R_{56}$ and $R_{58}$ are each hydrogen, then $R_{57}$ is not a $C_6$-$C_{60}$ aryl group substituted with a $C_1$-$C_{60}$ heteroaryl group, or provided that when the condensed cyclic compound is represented by Formula 1-4, $Ar_1$ is a group represented by Formula 2-7, $Ar_2$ is a group represented by Formulae 3-7, $Z_3$ is N, $Y_1$ and $Y_2$ are each a single bond, and $R_{11}$ to $R_{14}$, $R_{21}$ to $R_{24}$, and $R_{31}$ to $R_{34}$, $R_{51}$ to $R_{56}$ and $R_{58}$ are each hydrogen, then at least one of $Z_1$ and $Z_2$ is N, and $R_1$ to $R_7$, $R_{11}$ to $R_{19}$, $R_{21}$ to $R_{29}$, and $R_{31}$ to $R_{34}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si$(Q_1)(Q_2)(Q_3)$, —N$(Q_4)(Q_5)$, and —B$(Q_6)(Q_7)$, $R_{41}$ to $R_{48}$ and $R_{51}$ to $R_{58}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si$(Q_1)(Q_2)(Q_3)$, —N$(Q_4)(Q_5)$, and —B$(Q_6)(Q_7)$,

* and *' each indicate a binding site to an adjacent atom, and at least one substituent of the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si$(Q_{11})(Q_{12})(Q_{13})$, —N$(Q_{14})(Q_{15})$, and —B$(Q_{16})(Q_{17})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group and a monovalent non-aromatic condensed heteropolycyclic group, each substituted with at least one selected from deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si$(Q_{21})(Q_{22})(Q_{23})$, —N$(Q_{24})(Q_{25})$, and —B$(Q_{26})(Q_{27})$; and —Si$(Q_{31})(Q_{32})(Q_{33})$, —N$(Q_{34})(Q_{35})$, and —B$(Q_{36})(Q_{37})$, wherein $Q_1$ to $Q_7$, $Q_{11}$ to $Q_{17}$, $Q_{21}$ to $Q_{27}$, and $Q_{31}$ to $Q_{37}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

2. The organic light-emitting device of claim 1, wherein wherein, in Formulae 2-1 to 2-7 and 3-1 to 3-14, $R_1$ to $R_7$, $R_{11}$ to $R_{19}$, $R_{21}$ to $R_{29}$, and $R_{31}$ to $R_{34}$ are each independently selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof a sulfonic acid group or a salt thereof, a phosphoric acid group or a salt thereof, a phenyl group, a biphenyl group, a terphenyl group, and a naphthyl group;

a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptenyl group, an indacenyl group, an acenaphthyl group, a fluorenyl group, a spiro-bifluorenyl group, a phenalenyl group, a phenanthrenyl group, anthracenyl group, a fluoranthenyl group, a triphenylenyl group, a pyranyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, a indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, a acridinyl group, a phenathrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, an imidazopyridinyl group, a pyridoindolyl group, a benzofuropyridinyl group, a benzothienopyridinyl group, a pyridoindolyl group, a benzofuropyrimidinyl group, a benzothienopyrimidinyl group, a phenoxazinyl group, a pyridobenzoxazinyl group, ad a pyridobenzobiazinyl group;

a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexaacetyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, a isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, an imidazopyridinyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzoxazinyl group, and a pyridobenzothiazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a biphenyl group, a terphenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, —Si($Q_{31}$)($Q_{32}$)($Q_{33}$), —N($Q_{34}$)($Q_{35}$), and —B($Q_{36}$)($Q_{37}$); and —Si($Q_1$)($Q_2$)($Q_3$), —N($Q_4$)($Q_5$), and —B($Q_6$)($Q_7$), wherein $Q_1$ to $Q_7$ and $Q_{31}$ to $Q_{37}$ are each independently selected from hydrogen, a $C_1$-$C_{20}$ alkyl group, a $C_1$-$C_{20}$ alkoxy group, a phenyl group, a biphenyl group, a terphenyl group, a naphthyl group, a fluorenyl group, a carbazolyl group, a dibenzofuranyl group, and a dibenzothiophenyl group, and

* indicates a binding site to an adjacent atom.

3. The organic light-emitting device of claim 2, wherein $R_1$ to $R_7$, $R_{11}$ to $R_{19}$, $R_{21}$ to $R_{29}$, and $R_{31}$ to $R_{34}$ are each independently selected from:

hydrogen, deuterium, —F, —Cl, —Br, —I, a cyano group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a cyano group, a phenyl group, a biphenyl group, a terphenyl group, and a naphthyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group, each substituted with at least one selected from deuterium, a cyano group, a $C_1$-$C_{20}$ alkyl group, a $C_1$-$C_{20}$ alkoxy group, a phenyl group, a biphenyl group, a terphenyl group, a naphthyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ are each independently selected from hydrogen, a $C_1$-$C_{20}$ alkyl group, a $C_1$-$C_{20}$ alkoxy group, a phenyl group, a biphenyl group, a terphenyl group, and a naphthyl group.

4. The organic light-emitting device of claim 1, wherein the condensed cyclic compound is represented by Formula 1-4.

5. The organic light-emitting device of claim 1, wherein $R_{41}$ to $R_{48}$ and $R_{51}$ to $R_{58}$ are each independently selected from:

hydrogen, deuterium, —F, —Cl, —Br, —I, a cyano group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, a phenyl group, a biphenyl group, a terphenyl group, and a naphthyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group, each substituted with at least one selected from deuterium, a $C_1$-$C_{20}$ alkyl group, a $C_1$-$C_{20}$ alkoxy group, a phenyl group, a biphenyl group, a terphenyl group, a naphthyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ are each independently selected from hydrogen, a $C_1$-$C_{20}$ alkyl group, a $C_1$-$C_{20}$ alkoxy group, a phenyl group, a biphenyl group, a terphenyl group, and a naphthyl group.
6. The organic light-emitting device of claim 1, wherein Ar₁ is a group represented by one of Formulae 2-1 to 2-7, and Ar₂ is a group represented by one of Formulae 3-1 to 3-14:
2-1
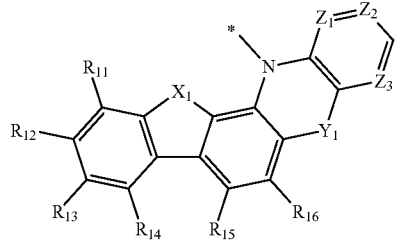
2-2
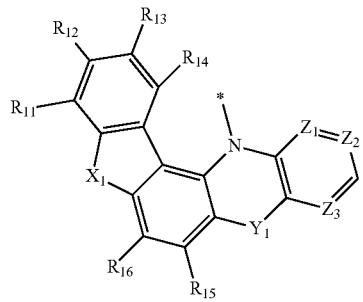
2-3
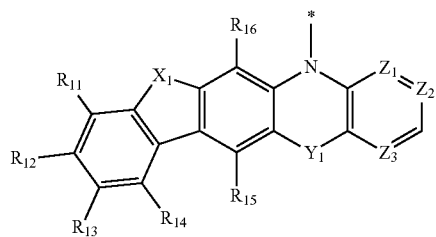
2-4
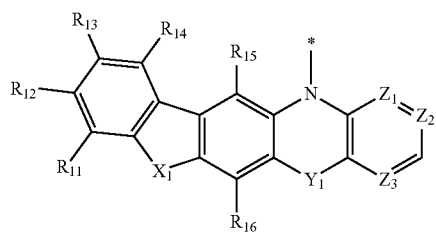
2-5
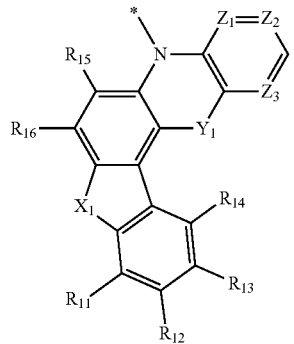
2-6
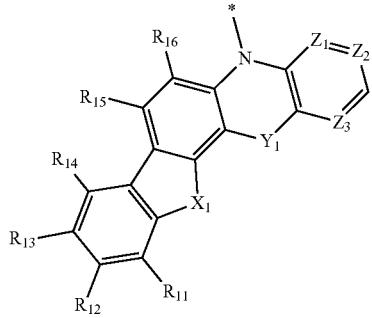
2-7
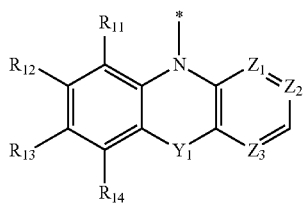
3-1
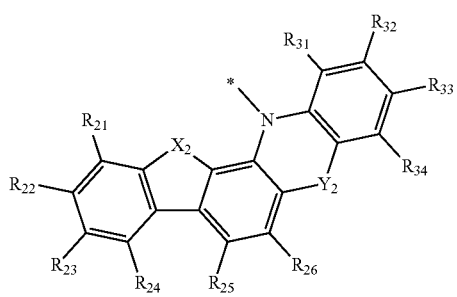
3-2
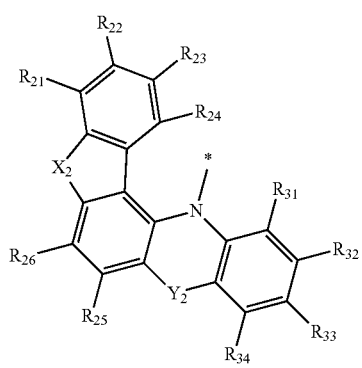
3-3
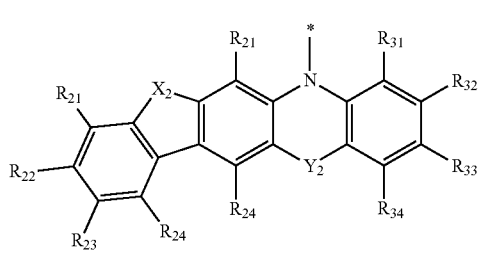

153
-continued
3-4
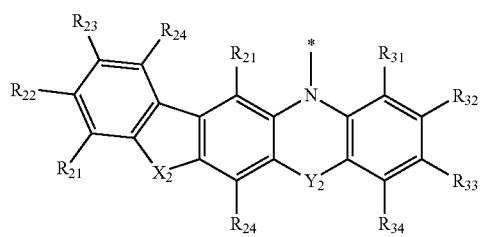
3-5
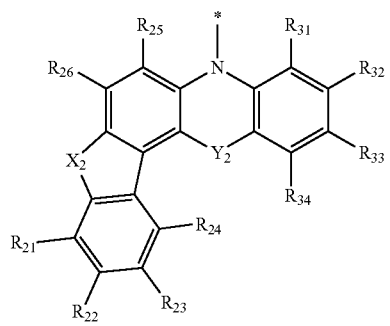
3-6
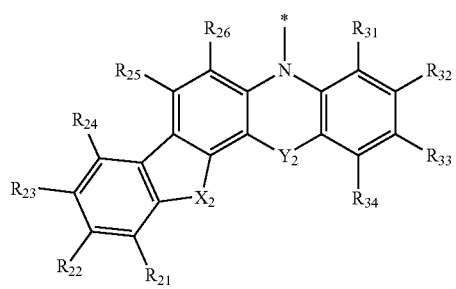
3-7
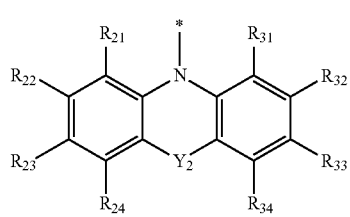
3-8
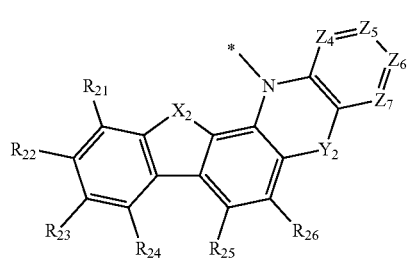
154
-continued
3-9
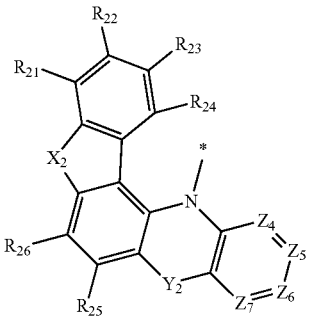
3-10
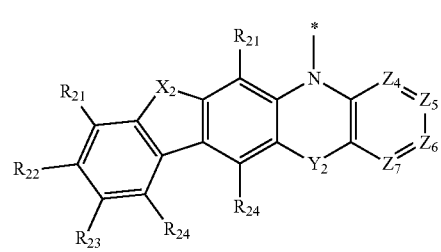
3-11
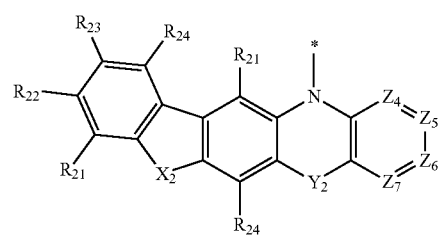
3-12
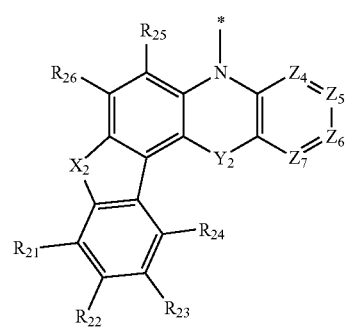
3-13
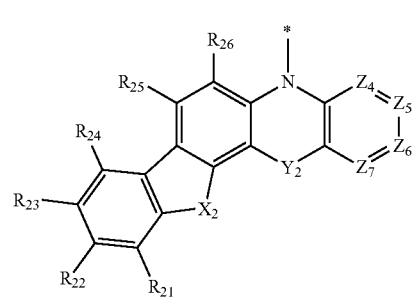

-continued 3-14

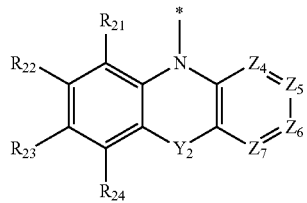

wherein, in Formulae 2-1 to 2-7 and 3-1 to 3-14, $X_1$ is $C(R_{17})(R_{18})$, $N(R_{19})$, O, or S, $X_2$ is $C(R_{27})(R_{28})$, $N(R_{29})$, O, or S, $Z_1$ to $Z_3$, $Y_1$, and $Y_2$ are defined the same as those in claim 1, $Z_4$ is N or $C(R_{31})$, $Z_5$ is N or $C(R_{32})$, $Z_6$ is N or $C(R_{33})$, $Z_7$ is N or $C(R_{34})$, at least one selected from $Z_4$ to $Z_7$ is N, and $R_1$ to $R_7$, $R_{11}$ to $R_{19}$, $R_{21}$ to $R_{29}$, and $R_{31}$ to $R_{34}$ are each independently selected from:

hydrogen, deuterium, a cyano group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, a cyano group, a phenyl group, a biphenyl group, a terphenyl group, and a naphthyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group, each substituted with at least one selected from deuterium, a cyano group, a $C_1$-$C_{20}$ alkyl group, a $C_1$-$C_{20}$ alkoxy group, a phenyl group, a biphenyl group, a terphenyl group, a naphthyl group, and —$Si(Q_{31})(Q_{32})(Q_{33})$; and —$Si(Q_1)(Q_2)(Q_3)$, wherein $Q_1$ to $Q_3$ and $Q_{31}$ to $Q_{33}$ are each independently selected from hydrogen, a $C_1$-$C_{20}$ alkyl group, a $C_1$-$C_{20}$ alkoxy group, a phenyl group, a biphenyl group, a terphenyl group, and a naphthyl group.

7. The organic light-emitting device of claim 6, wherein at least one selected from $R_{11}$ to $R_{19}$, $R_{21}$ to $R_{29}$, $R_{31}$ to $R_{34}$, $R_{41}$ to $R_{48}$, and $R_{51}$ to $R_{58}$ is a cyano group.

8. The organic light-emitting device of claim 1, wherein the first electrode is an anode, and the second electrode is a cathode, and wherein the organic layer comprises a hole transport region disposed between the first electrode and the emission layer and an electron transport region disposed between the emission layer and the second electrode, the hole transport region comprises at least one selected from a hole injection layer, a hole transport layer, and an electron blocking layer, and the electron transport region comprises at least one selected from a hole blocking layer, an electron transport layer, and an electron injection layer.

9. An organic light-emitting device comprising:

a first electrode;

a second electrode; and an organic layer disposed between the first electrode and the second electrode, wherein the organic layer comprises an emission layer and at least one condensed cyclic compound represented by Formulae 1-1 to 1-4, wherein the emission layer comprises the condensed cyclic compound represented by Formulae 1-1 to 1-4, wherein the condensed cyclic compound comprised in the emission layer is a fluorescent emitter, and a ratio of emission components emitted from the condensed cyclic compound is 80% or greater of the whole emission components emitted from the emission layer, wherein in Formulae 1-1 to 1-4, $Ar_1$ is a group represented by one of Formulae 2-1 to 2-7, and $Ar_2$ is a group represented by one of Formulae 3-1 to 3-14:

2-1

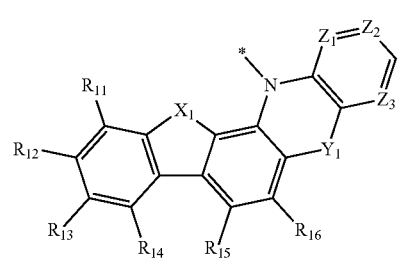

2-2

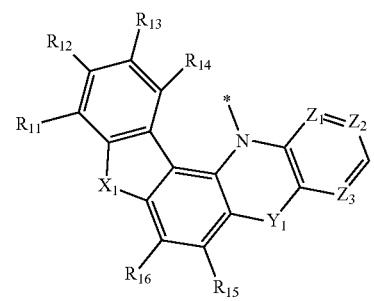

2-3

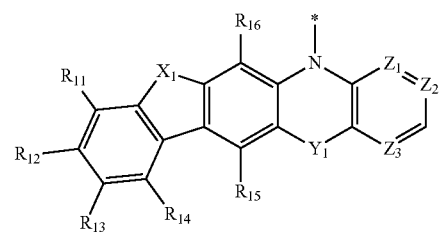

2-4

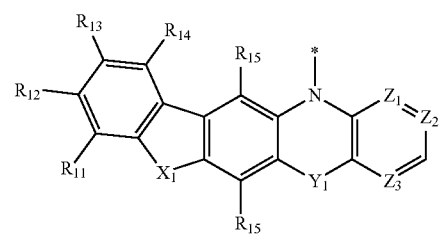

157
-continued
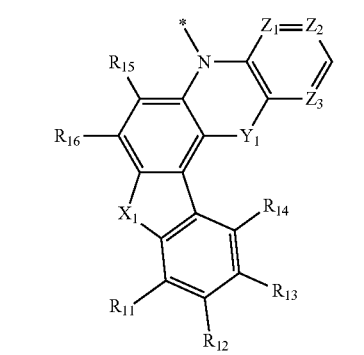
2-5
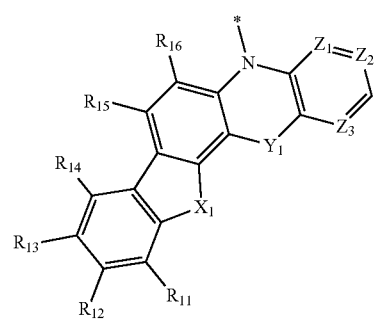
2-6
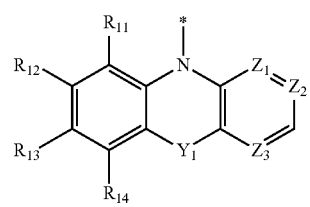
2-7
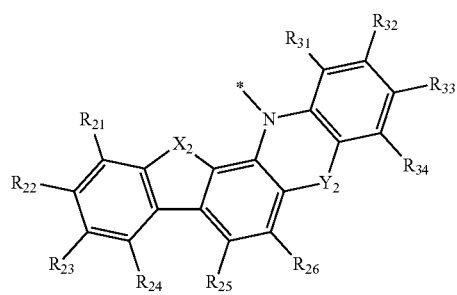
3-1
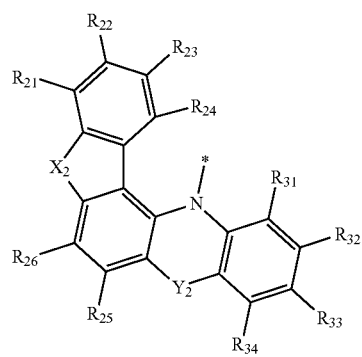
3-2
158
-continued
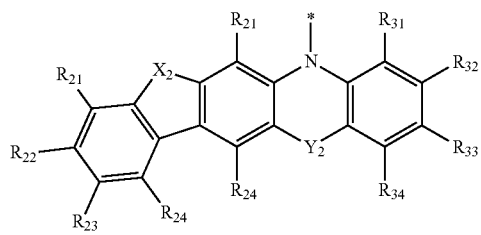
3-3
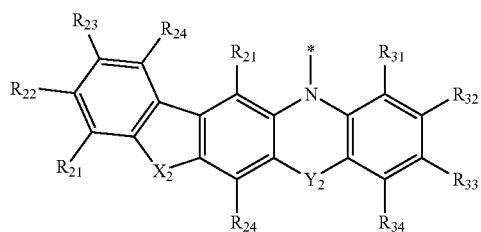
3-4
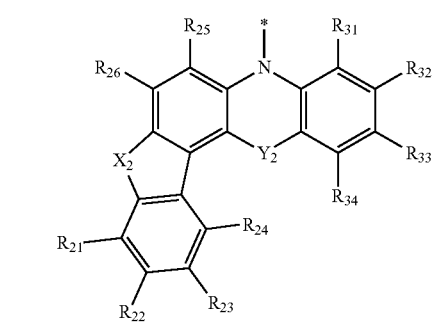
3-5
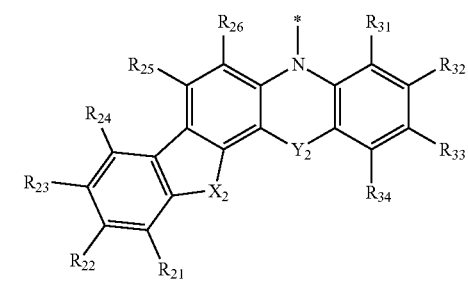
3-6
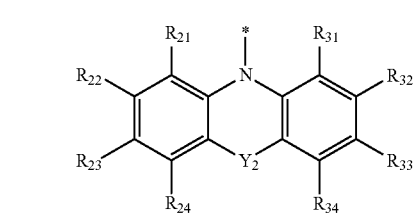
3-7
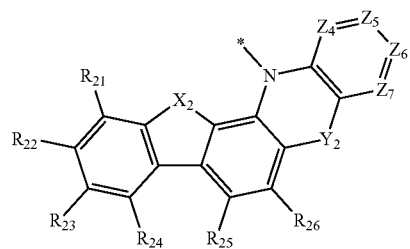
3-8 wherein:
X₁ is $C(R_{17})(R_{18})$, $N(R_{19})$, O, or S,
X₂ is $C(R_{27})(R_{28})$, $N(R_{29})$, O, or S,
$Z_1$ is N or $C(R_1)$, $Z_2$ is N or $C(R_2)$, $Z_3$ is N or $C(R_3)$, at least one selected from $Z_1$ to $Z_3$ is N,
$Y_1$ is a single bond, $C(R_4)(R_5)$, $N(R_4)$, O, or S,
$Y_2$ is a single bond, $C(R_6)(R_7)$, $N(R_6)$, O, or S,
$Z_4$ is N or $C(R_{31})$, $Z_5$ is N or $C(R_{32})$, $Z_6$ is N or $C(R_{33})$, $Z_7$ is N or $C(R_{34})$, at least one selected from $Z_4$ to $Z_7$ is N, and
provided that when the condensed cyclic compound is represented by Formula 1-4, Ar₁ is a group represented by Formula 2-7, Ar₂ is a group represented by Formulae 3-7, $Z_3$ is N, $Z_2$ is $C(R_2)$, $Z_3$ is $C(R_3)$, $Y_1$ and $Y_2$ are each a single bond, $R_2$, $R_3$, $R_{11}$ to $R_{14}$, $R_{21}$ to $R_{24}$, and $R_{31}$ to $R_{34}$, $R_{51}$ to $R_{56}$ and $R_{58}$ are each hydrogen, then $R_{57}$ is not a $C_6$-$C_{60}$ aryl group substituted with a $C_1$-$C_{60}$ heteroaryl group, or
provided that when the condensed cyclic compound is represented by Formula 1-4, Ar₁ is a group represented by Formula 2-7, Ar₂ is a group represented by Formulae 3-7, $Z_3$ is N, $Y_1$ and $Y_2$ are each a single bond, and $R_{11}$ to $R_{14}$, $R_{21}$ to $R_{24}$, and $R_{31}$ to $R_{34}$, $R_{51}$ to $R_{56}$ and $R_{58}$ are each hydrogen, then at least one of $Z_1$ and $Z_2$ is N, and
$R_1$ to $R_7$, $R_{11}$ to $R_{19}$, $R_{21}$ to $R_{29}$, and $R_{31}$ to $R_{34}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si(Q₁)(Q₂)(Q₃), —N(Q₄)(Q₅), and —B(Q₆)(Q₇),
$R_{41}$ to $R_{48}$ and $R_{51}$ to $R_{58}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_6$)($Q_7$),

* and *' each indicate a binding site to an adjacent atom, and at least one substituent of the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group and a monovalent non-aromatic condensed heteropolycyclic group, each substituted with at least one selected from deuterium, —$CD_3$, —$CD_2H$, —$CDH_2$, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$), and —B($Q_{26}$)($Q_{27}$); and —Si($Q_{31}$)($Q_{32}$)($Q_{33}$), —N($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

* * * * *